(12) United States Patent
Yu et al.

(10) Patent No.: US 9,889,180 B2
(45) Date of Patent: Feb. 13, 2018

(54) METHOD OF TREATING CANCER

(71) Applicant: Agency for Science, Technology and Research, Singapore (SG)

(72) Inventors: Qiang Yu, Singapore (SG); Zhen Ning Wee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 62 days.

(21) Appl. No.: 14/443,602

(22) PCT Filed: Nov. 19, 2013

(86) PCT No.: PCT/SG2013/000490
§ 371 (c)(1),
(2) Date: May 18, 2015

(87) PCT Pub. No.: WO2014/077784
PCT Pub. Date: May 22, 2014

(65) Prior Publication Data
US 2015/0258175 A1 Sep. 17, 2015

(30) Foreign Application Priority Data

Nov. 19, 2012 (SG) .............................. 201208522-1

(51) Int. Cl.

| | | |
|---|---|---|
| *A61K 31/713* | (2006.01) | |
| *A61K 31/706* | (2006.01) | |
| *A61K 31/437* | (2006.01) | |
| *A61K 38/21* | (2006.01) | |
| *G01N 33/574* | (2006.01) | |
| *C07K 16/40* | (2006.01) | |
| *C07K 14/57* | (2006.01) | |
| *C12Q 1/68* | (2018.01) | |
| *C12N 15/113* | (2010.01) | |

(52) U.S. Cl.
CPC .......... *A61K 38/217* (2013.01); *A61K 31/437* (2013.01); *A61K 31/706* (2013.01); *A61K 31/713* (2013.01); *C07K 16/40* (2013.01); *C12Q 1/6886* (2013.01); *G01N 33/57492* (2013.01); *G01N 33/57496* (2013.01); *C07K 2317/76* (2013.01); *C12N 15/1137* (2013.01); *C12N 2310/14* (2013.01); *C12Y 201/01043* (2013.01); *G01N 2800/52* (2013.01)

(58) Field of Classification Search
CPC .. A61K 31/713; A61K 31/706; A61K 38/217; A61K 31/437; A61K 2300/00; G01N 33/574921; G01N 33/57496; C07K 16/40
See application file for complete search history.

(56) References Cited

U.S. PATENT DOCUMENTS

| | | |
|---|---|---|
| 2001/0038832 A1 | 11/2001 | Bonavida |
| 2005/0002900 A1* | 1/2005 | Wong ................... A61K 38/217 424/85.5 |
| 2005/0059682 A1 | 3/2005 | Rubinfeld |
| 2009/0012031 A1* | 1/2009 | Chinnaiyan ............ A61K 31/35 514/44 R |
| 2010/0297657 A1 | 11/2010 | Chinnaiyan |

FOREIGN PATENT DOCUMENTS

| | | |
|---|---|---|
| WO | WO-2009105513 A2 | 8/2009 |
| WO | WO-2009143603 A1 | 12/2009 |
| WO | WO-2010132867 A1 | 11/2010 |
| WO | WO-2011103016 A2 | 8/2011 |
| WO | WO-2012034132 A2 | 3/2012 |
| WO | WO-2012051492 A2 | 4/2012 |

OTHER PUBLICATIONS

Kaplan, E. H. et al. Phase II study of recombinant human interferon gamma for treatment of cutaneous T-cell lymphoma. Journal of the National Cancer Institute, 1990, vol. 82, p. 208-212.*
Knutson, S.K. et a. A selective inhibitor of EZH2 blocks H3K27 methylation and kills mutant lymphoma cells. Nature Chemical Biology, 2012, vol. 8, p. 890-896.*
International Application No. PCT/SG2013/000490, International Search Report dated Feb. 7, 2014, 7 pgs.
"European Application Serial No. 13855314.4, Extended European Search Report dated Nov. 14, 2016", (Nov. 14, 2016), 17 pgs.
Alimova, Irina, et al., "Targeting the enhancer of zeste homologue 2 in medulloblastoma.", International journal of cancer 131.8, (2012), 1800-1809.
Dunn, Gavin P., et al., "Interferons, immunity and cancer immunoediting.", Nature Reviews Immunology 6.11, (2006), 836-848.
Hastie, Claire, "Interferon ?, a Possible Therapeutic Approach for Late-stage Prostate Cancer?", Anticancer research 28.5B, (2008), 2843-2849.
Wee, Zhen Nig, et al., "EZH2-mediated inactivation of IFN-?-JAK-STAT1 signaling is an effective therapeutic target in MYC-driven prostate cancer.", Cell reports 8.1, (2014), 204-216.

* cited by examiner

*Primary Examiner* — Robert Landsman
*Assistant Examiner* — Bruce D Hissong
(74) *Attorney, Agent, or Firm* — Schwegman Lundberg & Woessner, P.A.

(57) ABSTRACT

The present invention relates to a pharmaceutical composition comprising a histone-lysine N-methyltransferase EZH2 (enhancer of zeste homolog 2) inhibitor and an enhancer of interferon-gamma receptor activity. The invention also relates to method of treating a patient having cancer, comprising administration of the pharmaceutical composition.

17 Claims, 34 Drawing Sheets

| Analysis Type by Cancer | EZH2 Cancer vs. Normal | | IFNGR1 Cancer vs. Normal | |
|---|---|---|---|---|
| Bladder Cancer | 6 | | | |
| Brain and CNS Cancer | 11 | 1 | 8 | 2 |
| Breast Cancer | 11 | 2 | 1 | 7 |
| Cervical Cancer | 4 | | 3 | |
| Colorectal Cancer | 20 | | | 7 |
| Esophageal Cancer | 2 | 1 | | |
| Gastric Cancer | 3 | | 12 | |
| Head and Neck Cancer | 4 | 1 | 9 | |
| Kidney Cancer | 6 | 1 | 5 | 1 |
| Leukemia | 5 | 6 | 2 | 14 |
| Liver Cancer | 4 | | 2 | |
| Lung Cancer | 16 | | 1 | 11 |
| Lymphoma | 4 | | 2 | 1 |
| Melanoma | | | | |
| Myeloma | 1 | | 1 | 1 |
| Other Cancer | 8 | 7 | 3 | |
| Ovarian Cancer | 6 | | | 5 |
| Pancreatic Cancer | 2 | | 4 | |
| Prostate Cancer | 6 | | | 1 |
| Sarcoma | 11 | | 3 | 4 |
| Significant Unique Analyses | 128 | 19 | 49 | 54 |
| Total Unique Analyses | 393 | | 407 | |

P-value < 0.001,
Threshold 1.5 folds

US 9,889,180 B2

METHOD OF TREATING CANCER

CROSS-REFERENCE TO RELATED APPLICATIONS

This application is a U.S. National Stage Filing under 35 U.S.C. 371 from International Application No. PCT/SG2013/000490, entitled "METHOD OF TREATING CANCER," filed on month Nov. 19, 2013, and published as WO 2014/077784 A1 on May 22, 2014, which claims the benefit of priority of Singapore provisional patent application No. 201208522-1, filed Nov. 19, 2012, the contents of each of which being hereby incorporated by reference in their entirety for all purposes.

FIELD OF THE INVENTION

The present invention relates to pharmaceutical compositions and methods for treating cancer. The present invention further relates to compositions and methods for cancer diagnostics, including but not limited to, cancer markers and also provides novel markers useful for the diagnosis, characterization, and treatment of cancers.

BACKGROUND OF THE INVENTION

While hormonal therapy has been largely successful in the management of cancer patients in their early stages, the disease often progresses to metastatic disease which is hormone refractory and resistant to existing treatments. There is currently no optimal treatment that can slow down the disease progression in patients with metastatic disease.

For example, in patient with advanced prostate tumours, the current treatment include surgical treatments such as radical prostatectomy (RP), in which the prostate is completely removed (with or without nerve sparing techniques) and radiation or chemotherapy. Hormone therapy such as anti-androgen therapy is also used, alone or in conjunction with surgery or radiation. IFN-γ is an example of anti-tumour agent that has been used to treat cancers, including prostate and breast cancer but with limited success. Hence, while hormonal and surgical treatments are often effective for localized prostate cancer, advanced disease is often refractory to such treatments and thus, incurable.

Treatment of cancer can be more efficient if some early genetic markers are identified that allow adapted treatments that would allow the use of smaller amounts of chemotherapeutic agents and restoration of normal cell function. In addition, much effort has been expended to identify genetic determinants in patient outcomes, so as to improve clinical treatment decisions and for the design of therapeutic agents. To date, no known genetic markers have been reported, that could help determine the dose and clinical outcomes in patients receiving anti-cancer treatments.

Recent introduction of targeted therapy and increasing numbers of available chemotherapeutic regimens, such as platinum and derivatives, taxanes and gemcitabine, do not effectively cure cancer patients, with varied response towards treatment and occurrence of drug toxicity. In addition, prognosis remains dismal in advanced cancer patients albeit careful evaluation of clinico-pathological factors that determine patient response to therapy, such as tumor, nodes and metastasis (TNM) staging, performance status, gender and weight loss.

Accordingly, there is a need for developing new therapeutic targets and pharmaceutical compositions for the treatment of cancer patients.

SUMMARY OF THE INVENTION

In a first aspect, the present invention provides a pharmaceutical composition comprising a histone-lysine N-methyltransferase EZH2 (enhancer of zeste homolog 2) inhibitor and an enhancer of interferon-gamma receptor activity.

In a second aspect, the present invention provides a method of treating a patient having cancer comprising administration of the pharmaceutical composition as defined herein.

In a third aspect, the present invention provides a method for determining susceptibility of a patient suffering from cancer to a treatment with a pharmaceutical composition as defined herein, wherein the method comprises, comparing a first level of EZH2 comprising but not limited to EZH2 mRNA level in a tumor sample, EZH2 cDNA level made from mRNA from said tumor sample, and EZH2 protein level from said tumor sample, with a second level of EZH2 comprising but not limited to EZH2 mRNA level from a non-tumor sample from said patient, EZH2 cDNA level made from mRNA from said non-tumor sample, and EZH2 protein level from said non-tumor sample; comparing a first level of IFNGR1 comprising but not limited to IFNGR1 mRNA level from said tumor sample, IFNGR1 cDNA level made from mRNA from said tumor sample, and IFNGR1 protein level from said tumor sample with the level of IFNGR1 comprising but not limited to IFNGR1 mRNA level from a non-tumor sample from said patient, IFNGR1 cDNA level made from mRNA from said non-tumor sample, and IFNGR1 protein level from said non-tumor sample; and wherein a patient characterized by an increased level of EZH2 in said tumor sample and a decreased level of IFNGR1 in said tumor sample is susceptible to a treatment with said pharmaceutical composition.

In a fourth aspect, the present invention provides a method for treating cancer in a patient with a difference in the level of EZH2 mRNA, and/or EZH2 cDNA, and/or EZH2 protein and IFNGR1 mRNA, and/or IFNGR1 cDNA, and/or IFNGR1 protein in a tumor sample, and the level of EZH2 mRNA, and/or EZH2 cDNA, and/or EZH2 protein and IFNGR1 mRNA, and/or IFNGR1 cDNA, and/or IFNGR1 protein from a non-tumor sample, wherein the level of EZH2 mRNA, and/or EZH2 cDNA, and/or EZH2 protein are at least 2-fold higher in the tumor sample and the IFNGR1 mRNA, and/or IFNGR1 cDNA, and/or IFNGR1 protein level is at least 2-fold lower in the tumor sample, wherein the method comprises administration of a pharmaceutical composition as defined herein to the patient.

In a fifth aspect, disclosed herein is a method for determining susceptibility of a patient suffering from advanced prostate cancer to a treatment with a pharmaceutical composition as defined herein, wherein the method comprises comparing a first level of IFNGR1 comprising but not limited to IFNGR1 mRNA level in a tumor sample, IFNGR1 cDNA level made from mRNA from said tumor sample, and IFNGR1 protein level from said tumor sample with the level of IFNGR1 comprising but not limited to IFNGR1 mRNA level from a non-tumor sample from said patient, IFNGR1 cDNA level made from mRNA from said non-tumor sample; and IFNGR1 protein level from said non-tumor sample; and wherein a patient characterized by a decreased level of IFNGR1 in said tumor sample is susceptible to a treatment with said pharmaceutical composition.

In a sixth aspect, disclosed herein is a method for determining susceptibility of a patient suffering from breast cancer to a treatment with a pharmaceutical composition as defined herein, wherein the method comprises comparing a first level of IFNGR1 comprising but not limited to IFNGR1 mRNA level in a tumor sample, IFNGR1 cDNA level made from mRNA from said tumor sample, and IFNGR1 protein level from said tumor sample with the level of IFNGR1 selected from the group consisting of IFNGR1 mRNA level from a non-tumor sample from said patient, IFNGR1 cDNA level made from mRNA from said non-tumor sample, and IFNGR1 protein level from said non-tumor sample wherein a patient suffering from basal breast cancer is characterized by an increased level of INFGR1 in said tumor sample is not susceptible to a treatment with said pharmaceutical composition and wherein a patient suffering from luminal breast cancer is characterized by a decreased level of INFGR1 in said tumor sample is susceptible to a treatment with said pharmaceutical composition.

In a seventh aspect, disclosed herein is a method for making a prognosis with respect to the clinical outcome of a patient suffering from cancer comprising comparing a first level of EZH2 comprising but not limited to EZH2 mRNA level in a tumor sample, EZH2 cDNA level made from mRNA from said tumor sample, and EZH2 protein level from said tumor sample, with a second level of EZH2 comprising but not limited to EZH2 mRNA level from a non-tumor sample from said patient, EZH2 cDNA level made from mRNA from said non-tumor sample, and EZH2 protein level from said non-tumor sample, comparing a first level of IFNGR1 comprising but not limited to IFNGR1 mRNA level from said tumor sample, IFNGR1 cDNA level made from mRNA from said tumor sample, and IFNGR1 protein level from said tumor sample with the level of IFNGR1 comprising but not limited to IFNGR1 mRNA level from a non-tumor sample from said patient, IFNGR1 cDNA level made from mRNA from said non-tumor sample, and IFNGR1 protein level from said non-tumor sample and making a prognosis with respect to the clinical outcome of a patient suffering from cancer.

BRIEF DESCRIPTION OF THE DRAWINGS

The invention will be better understood with reference to the detailed description when considered in conjunction with the non-limiting examples and the accompanying drawings, in which:

FIG. 1(A) is an unsupervised hierarchical clustering showing 610 genes that were differentially regulated in either RWPE1-MYC and RWPE1-PI3K cells compared to RWPE1-vector control cells (2-fold cutoff, P<0.01) The colored scale bar represents the absolute fold change.

FIG. 1(B) is a table summarizing an Ingenuity Pathway Analysis (IPA) that shows interferon signaling pathway as the top gene network enriched in downregulated genes in transformed RWPE1 cells.

FIG. 1(C) is a Venn diagram (not drawn to scale) showing the overlapping of genes downregulated in RWPE1-MYC and RWPE1-PI3K cells with known IFN genes in the INTERFEROME database.

FIG. 1(D) is a graphical depiction of representative IFN genes in the IFN-JAK-pathway. Shadowed molecules represent the genes that were downregulated in RWPE1-MYC and RWPE1-PI3K cells.

FIG. 1(E) is a bar graph plotting the values of an ELISA assay. FIG. 1E shows JAK2 phosphorylation and activation in RWPE cells treated with or without IFN-γ treatment. The Y1007/1008 phosphorylation level of JAK2 was normalized and expressed fold change against the total JAK2 level. Sensitivity to IFN-γ was determined by comparing the phosphorylation status of JAK2 between IFN-γ treated and untreated control cells.

FIG. 1(F) is a graph summarizing the STAT1-driven luciferase reporter activity of indicated RWPE1 cell lines treated with or without IFN-γ.

FIG. 1(G) is a series of western blots showing the IFNGR1 and STAT1 phosphorylation in RWPE1 cell lines treated with or without 25 ng/mL of IFN-γ.

FIGS. 1(H) and 1(I) are a pair of graphs depicting qRT-PCR analysis of IFNGR1 and multiple IFN genes in RWPE1-MYC and RWPE1-PI3K cells as well as (I) prostate cancer cell lines normalized to RWPE1 control counterparts. All the data in the graph bars represent mean+Standard error of the mean (or measurement; (SEM)), n=3.  p<0.01, *p<0.001, n.s=not significant.

FIG. 2(A) is a graph showing qRT-PCR analysis of IFNGR1 and other IFN genes upon ectopic EZH2 expression in RWPE1 cells.

FIG. 2(B) is a pair of bar graphs showing a qRT-PCR analysis demonstrating the restoration of IFNGR1 expression, but not IFNAR1, following EZH2 knockdown in RWPE1-MYC cells but not in RWPE1-PI3K cells.

FIG. 2 (C) is a western blot validating the overexpression of c-MYC, constitutive active mutant of PI3K and phosphorylation status of AKT and EZH2 in RWPE1 cell lines treated with or without 25 ng/mL of IFN-γ.

FIG. 2 (D) is a schematic drawing showing the ChIP primer locations with respect to the transcriptional start site (TSS) of the IFNGR1 promoter.

FIG. 2 (E) is a series of histogram plots of ChIP analysis showing the enrichment of EZH2 at the promoter of IFNGR1 in transformed cell lines as indicated. The fold enrichments over IgG control further normalized to the actin promoter are shown. EZH2 known target CNR promoter was used as a positive control.

FIG. 2(F) is a series, of graphs of ChIP analysis showing EZH2 enrichment at the promoter of IFNGR1 in indicated prostate cancer cell lines.

FIG. 2(G) is a pair of bar graphs of ChIP analysis showing the enrichment of EZH2 and H3K27me3 in the IFNGR1 promoter in DU145 and LNCaP cells before and after MYC knockdown. All the data in the graph bars represent mean+SEM, n=3. *p<0.05,  p<0.01, *p<0.001, n.s=not significant.

FIG. 3(A) is a series of scatter plots showing the mRNA expression (Log 2) of EZH2, MYC, IFNGR1 and IFN-γ responsive genes (MX1, IRF1 and IFI16) to compare between Metastatic (n=35) and localized Prostate tumors (n=59) with normal prostate tissue (n=28) from the Grasso Prostate dataset (p<0.01, *p<0.001).

FIG. 3(B) is a series of scatter plots showing the mRNA expression (Log 2) of IFNGR1 (left) and EZH2 (right) after stratifying all prostate cancer tumors in the Grasso Prostate dataset according to their MYC expression. Prostate tumors with MYC expression higher than its median level were categorized as the "Hi-MYC" group (n=59) and vice versa for the "Low-MYC" group (n=61). This analysis excludes the normal prostate tissue. (*p<0.05, ***p<0.001).

FIG. 3(C) is a series of representative images of the prostate cancer TMA-IHC staining showing the downregulation of IFNGR1 in metastatic and advanced prostate cancer tumors with high levels of EZH2 and MYC. Scale bars=100 μm.

FIG. 4(A) is a series of graphs of qRT-PCR analysis of three IFN responsive genes, MX1, IRF1 and IFI16 in DU145, PC3, LNCaP and 22RV1 cells. The indicated cells lines where treated with siRNA to knockdown EZH2 expression and treated with the indicated amount of IFN-γ afterwards.

FIG. 4(B) is a series of western blot analysis of IFNGR1 expression and IFN-γ signaling upon EZH2 knockdown in the presence of IFN-γ at the doses indicated (0, 5 and 25 ng/ml).

FIG. 4(C) is a bar graph of an ELISA assay showing JAK2 phosphorylation and activation in DU145 cells treated with siEZH2, IFN-γ (25 ng/mL) or both. The Y1007/1008 phosphorylation level of JAK2 was normalized and expressed as fold change against the total JAK2 level.

FIG. 4(D) is a series of western blot analysis of IFNGR1 expression and IFN-γ signaling upon MYC knockdown in the presence of IFN-γ at indicted doses.

FIG. 4(E) is a series of scatter plots of cell proliferation assay in DU145 and LNCaP cells treated with either siRNA against MYC (siMYC) or EZH2 (siEZH2) in combination with IFN-γ. The proliferation of the cells are represented as fold change after normalizing to the baseline Cell Titer Glow (CTG) signal on Day 0 ($T_0$).

FIG. 4(F) is a pair of histogram plots of sub-G1 (apoptosis) by FACS analysis. Left, Sub-G1 DNA assessment by FACS in DU145 cells treated with siEZH2 or siMYC together with IFN-γ, in the presence or absence of CD119 a neutralizing antibody that blocks the binding of the activating ligand, IFN-γ to its receptor, IFNGR1. This prevents the activation of the IFN-γ signaling pathway. Hence, FIG. 4(F) shows that inhibition of EZH2 specifically enhances IFN-γ mediated cell death. Right, Sub-G1 DNA analysis by FACS in LNCaP cells treated with siMYC or siEZH2 in combination with IFN-γ.

FIG. 4(G) is a series of histogram plots and microscopy images of prostatospheres formation assays. Left, Prostatosphere formation assay after treating DU145, PC3, LNCaP and 22RV1 with either IFN-γ, siEZH2 or both for 7 days. Right, representative phase contrast microscopy images of the prostatospheres taken at 10× magnification after treatment with siEZH2 and IFN-γ (25 ng/mL).

All the data in the graph bars represent mean+SEM, n=3. *p<0.05,  p<0.01, *p<0.001, n.s=not significant.

Figure 5:
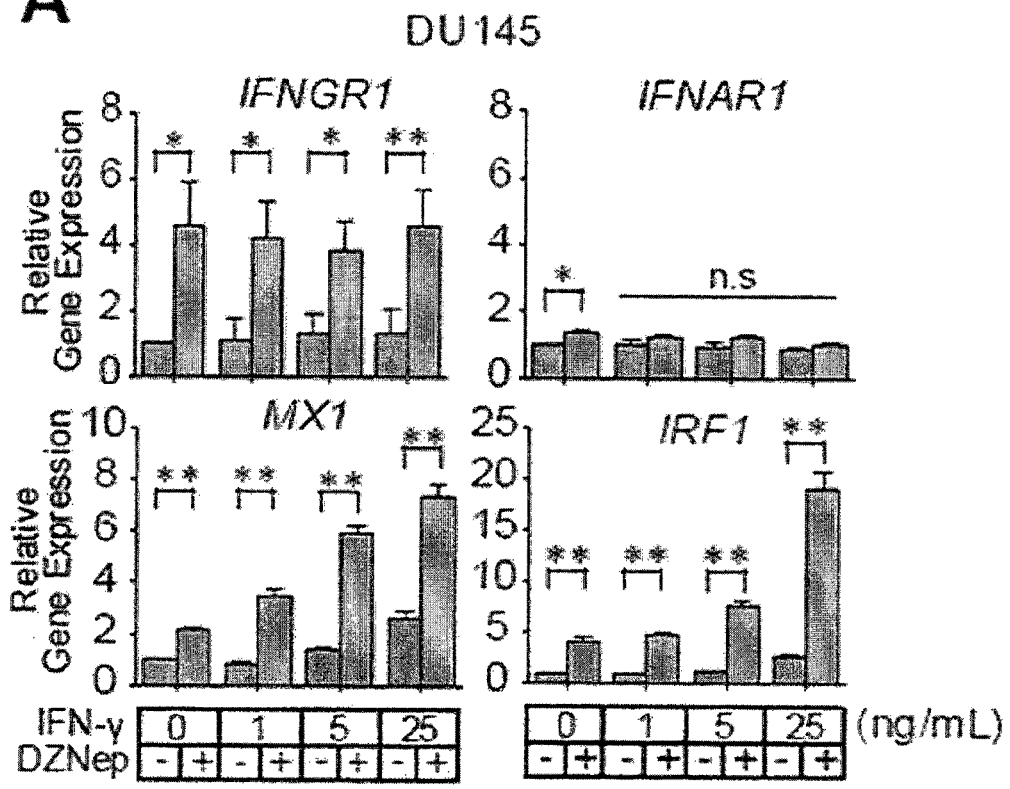
Figure 5:
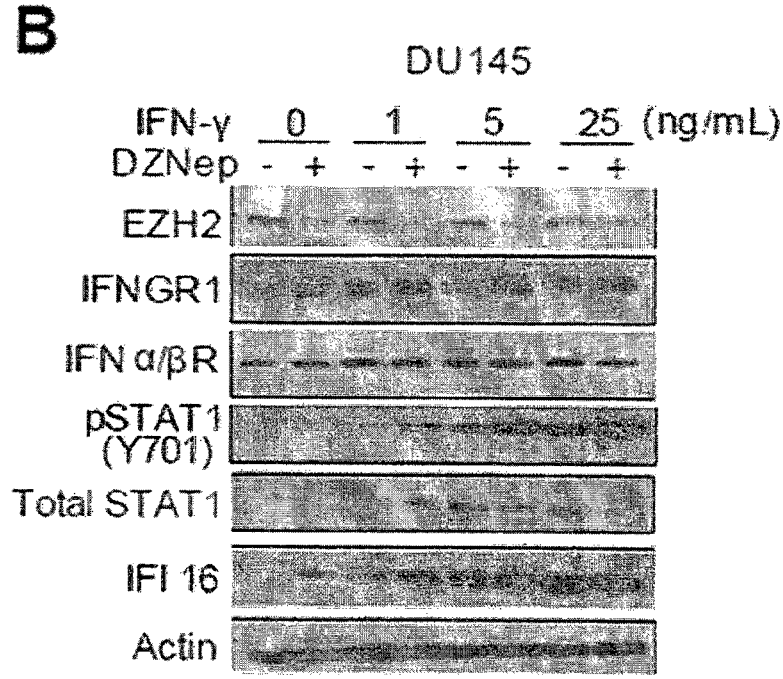
Figure 5:
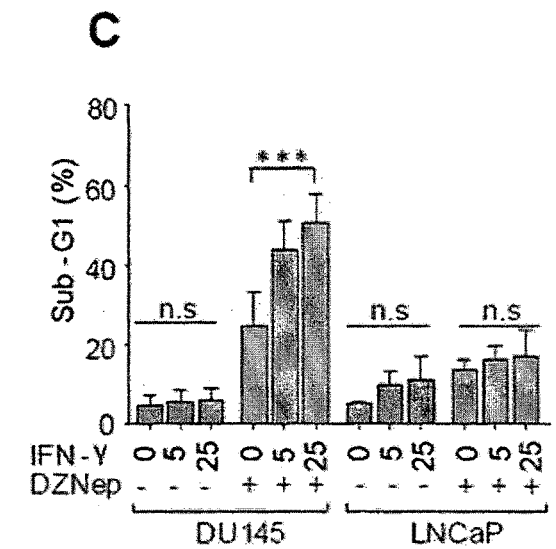
Figure 5:
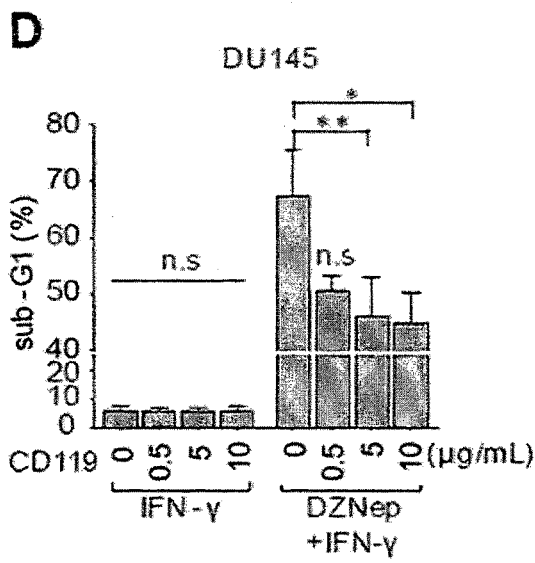
Figure 5:
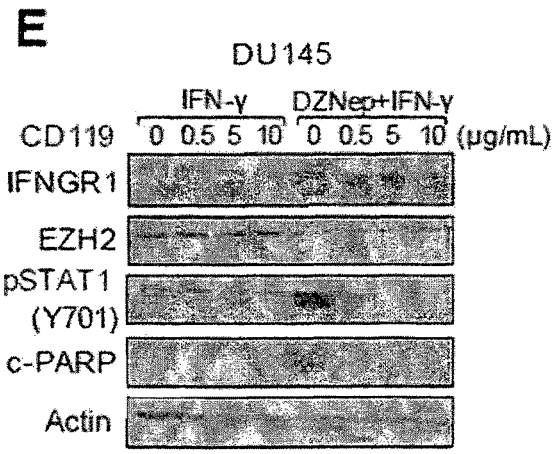
Figure 5:
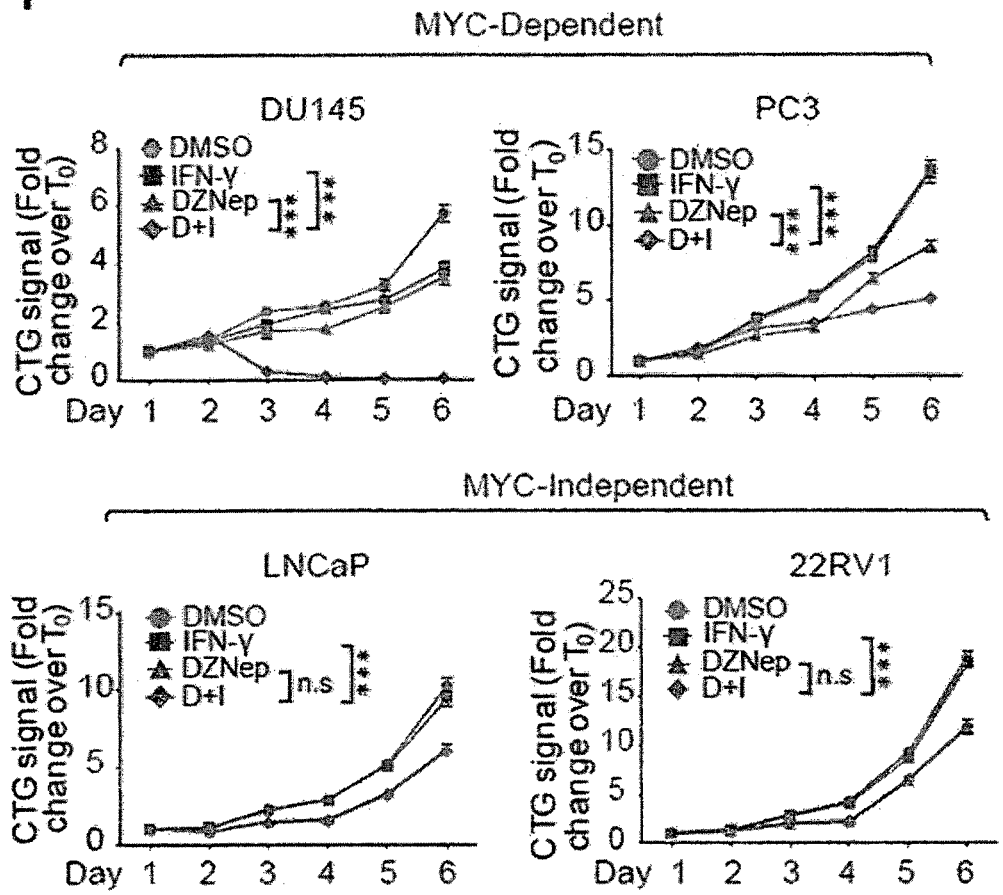
Figure 5:
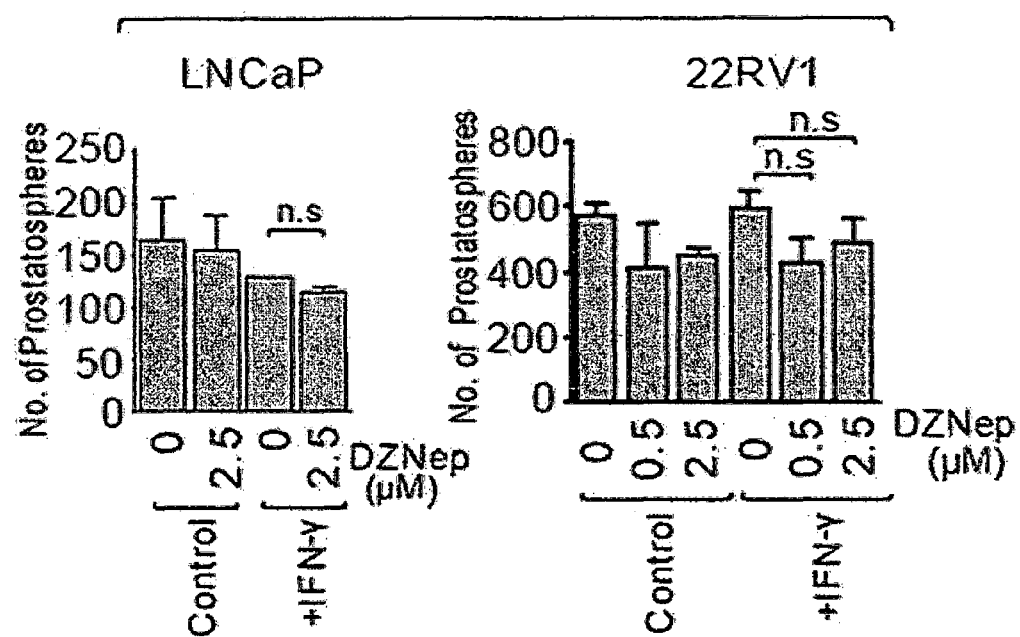
Figure 5:
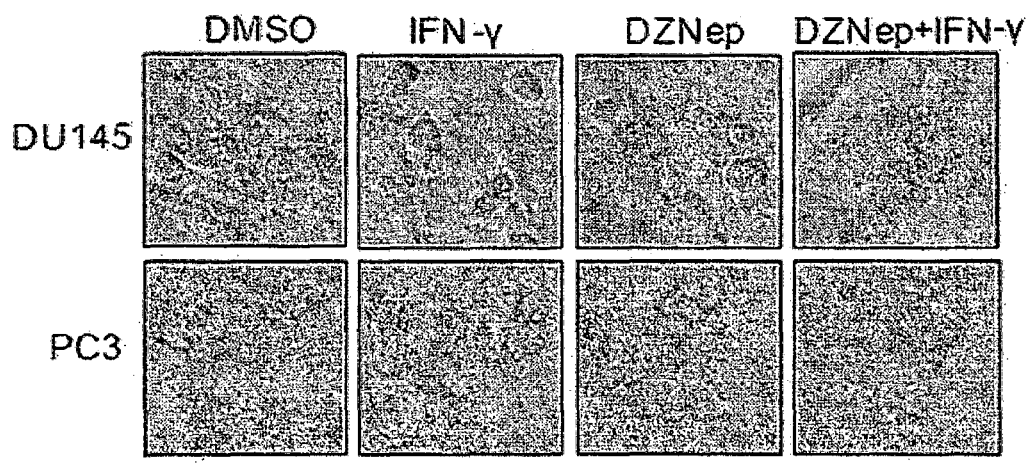

FIG. 5 is a series of graphs and western blots demonstrating that DZNep mimics EZH2 knockdown and is capable of restoring IFN-γ response to induce growth inhibition and apoptosis.

FIG. 5(A) is a series of histogram plots of quantitative PCR showing the increase in gene expression of IFNGR1 and various IFN responsive genes but not IFNAR1 after 72 hr of DZNep treatment (2.5 μM) as well as IFNγ treatment at indicated doses.

FIG. 5(B) is a series of western blot analysis of IFNGR1 expression and IFN-γ signaling in DU145 cells treated with DZNep (2.5 μM), IFN-γ at the indicated concentration or both for 3 days.

FIG. 5(C) is a histogram plot of a FACS sub-G1 DNA analysis in DU145 and LNCaP cells treated as (B).

FIG. 5(D) is a histogram plot of a FACS sub-G1 DNA analysis in DU145 cells treated with DZNep/IFN-γ as above in the presence or absence of IFNGR1 neutralizing antibody CD119 at indicated concentrations.

FIG. 5(E) is a series of western blot analysis of EZH2, IFN signaling and PARP cleavage in DU145 cells treated with DZNep/IFN-γ with similar conditions as (D).

FIG. 5(F) is a series of scatter plots showing cell proliferation assay of MYC-dependent cell lines (DU145 and PC3) and MYC-independent cell lines (LNCaP and 22RV1) after treatment with either IFN-γ, DZNep or both for days as indicated. The proliferation of the cells are represented as fold change after normalizing to the baseline Cell Titer Glow (CTG) signal on Day 0 (T0).

FIG. 5(G) is a pair of histogram plots and representative phase contrast microscopy images of the prostatospheres formation assays. Left, prostatosphere formation assay showing the effectiveness of combining low doses of DZNep with IFNγ to inhibit the formation of prostatospheres in indicated cell lines. Right, representative phase contrast microscopy images of the prostatospheres of DU145 and PC3 taken at 10× magnification after treatment with DZNep (0.504) and IFN-γ (25 ng/mL).

All the data in the graph bars represent mean+SEM, n=3. *p<0.05,  p<0.01, *p<0.001, n.s=not significant is a series of micrographs and a pair of bar graphs showing that the DZNep and IFN-γ combination significantly reduces the quantity and size of prostatospheres. The quantification of the prostatospheres was done with the Gelcount colony counter. The minimum size for prostatospheres derived from DU145 to be considered positive was set at 120 μM. (The cut-off varies from cell line to cell line and it is largely dependent on the proliferation rate of the cell lines as well as the length of the experiment.

Figure 6:
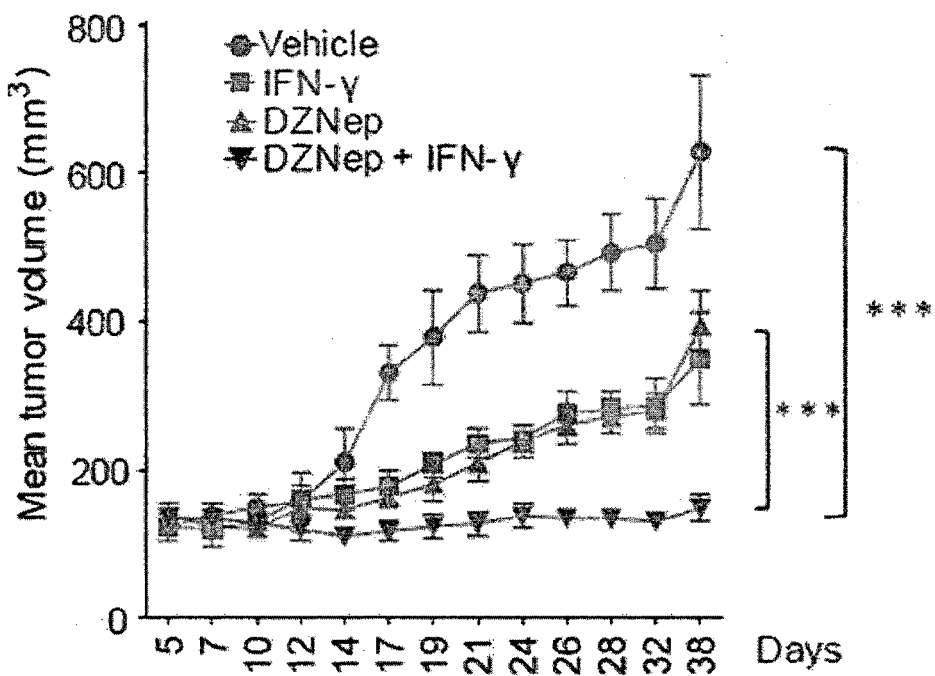
Figure 6:
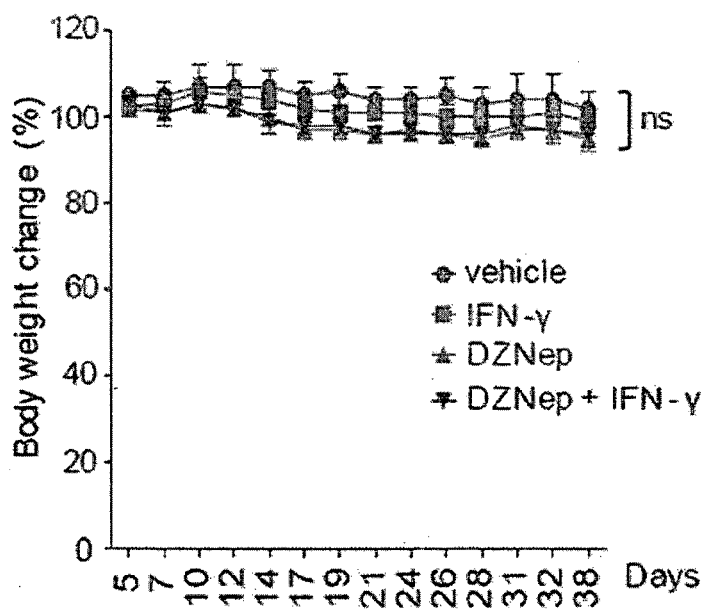
Figure 6:
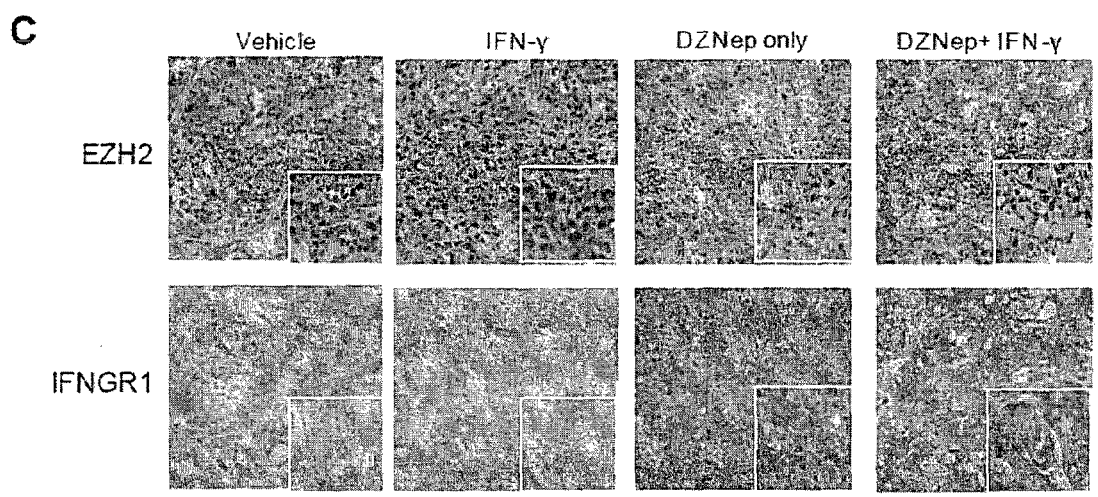

FIG. 6 is a pair of scatter plots and immunohistochemistry staining images showing combinatorial anti-tumour effect of DZNep and IFN-γ in vivo.

FIG. 6(A) is a scatter plot showing DU145 xenograft tumor growth in male athymic nude mice treated with vehicle (n=5), IFN-γ ($1 \times 10^7$ IU/kg, intraperitoneally (i.p.) n=6), DZNep (1 mg/kg, subcutaneously (s.c.) n=7) or both (n=8). Thus FIG. 6(A) is a graph establishing that a composition comprising DZNep and IFN-γ shows a synergistic effect in vivo in its ability to shrink or stabilize the volume of a tumour resulting from the xenograft of DU145 in mice. Mean tumor volume±s.e.m. is shown ***p<0.001.

FIG. 6(B) is a scatter plot showing the body weight change s.e.m) of the mice during the drug treatment as indicated above.

FIG. 6(C) is as series of images of immunohistochemistry analysis of EZH2 and IFNGR1 expression in tissue sections taken from DU145 xenograft tumors after the treatment as described in FIG. 6(A).

Figure 7:
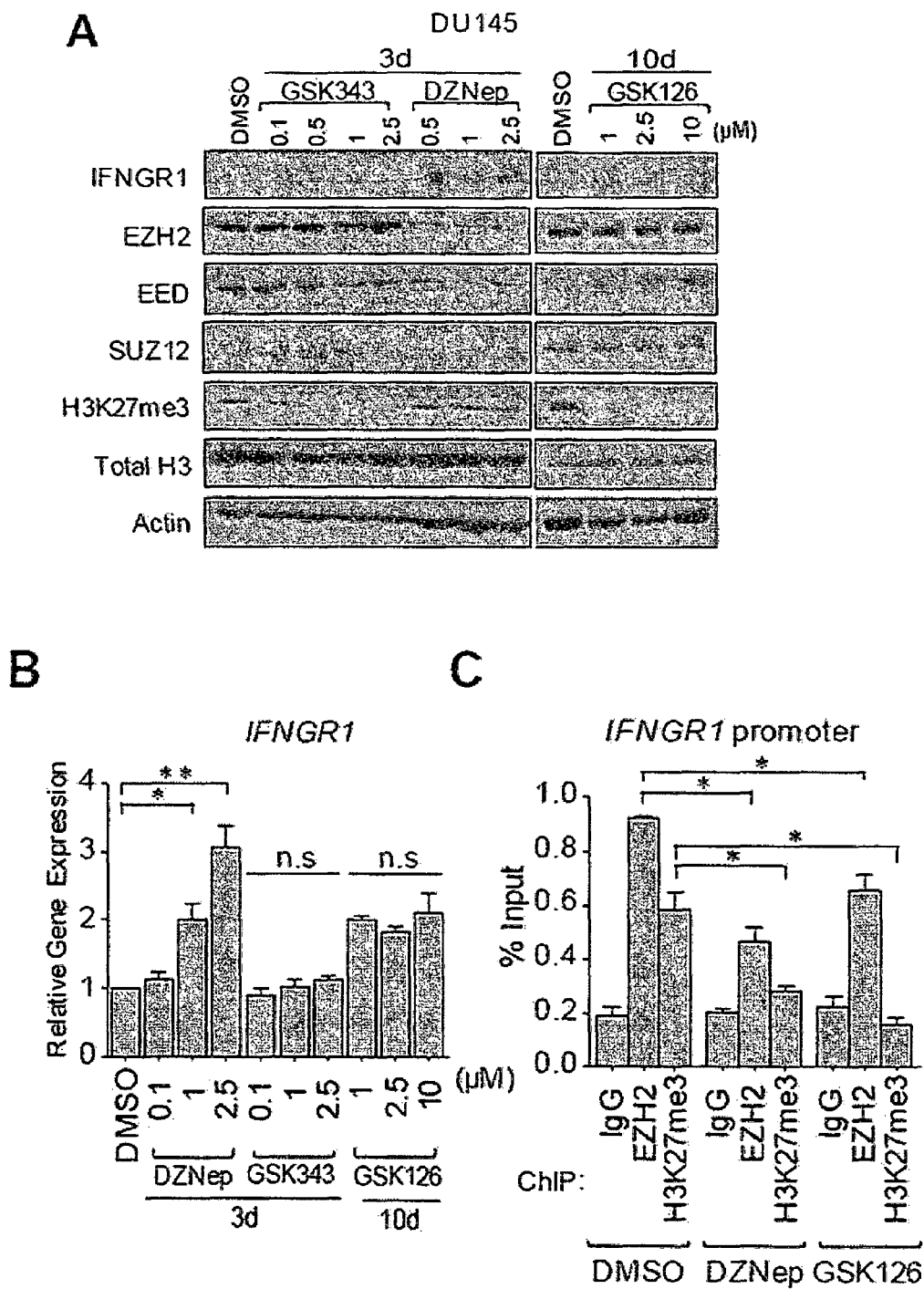
Figure 7:
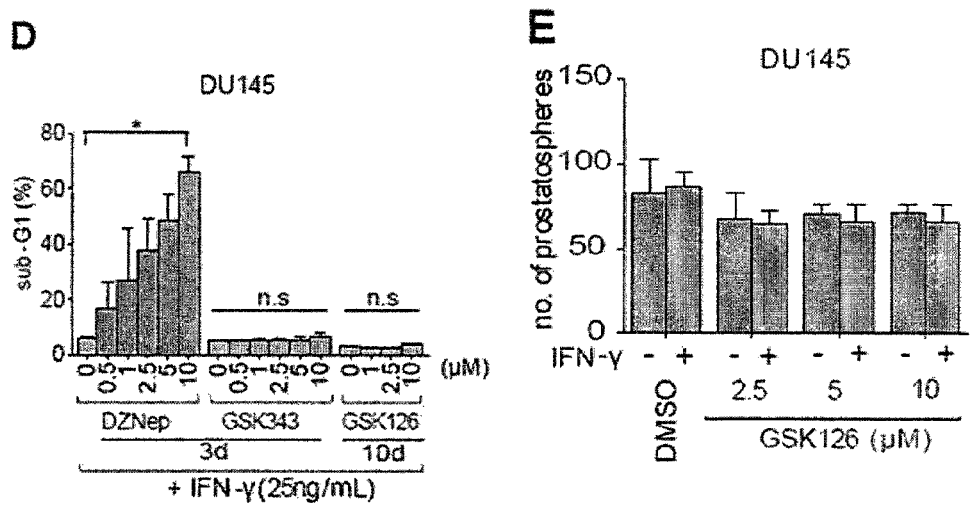
Figure 7:
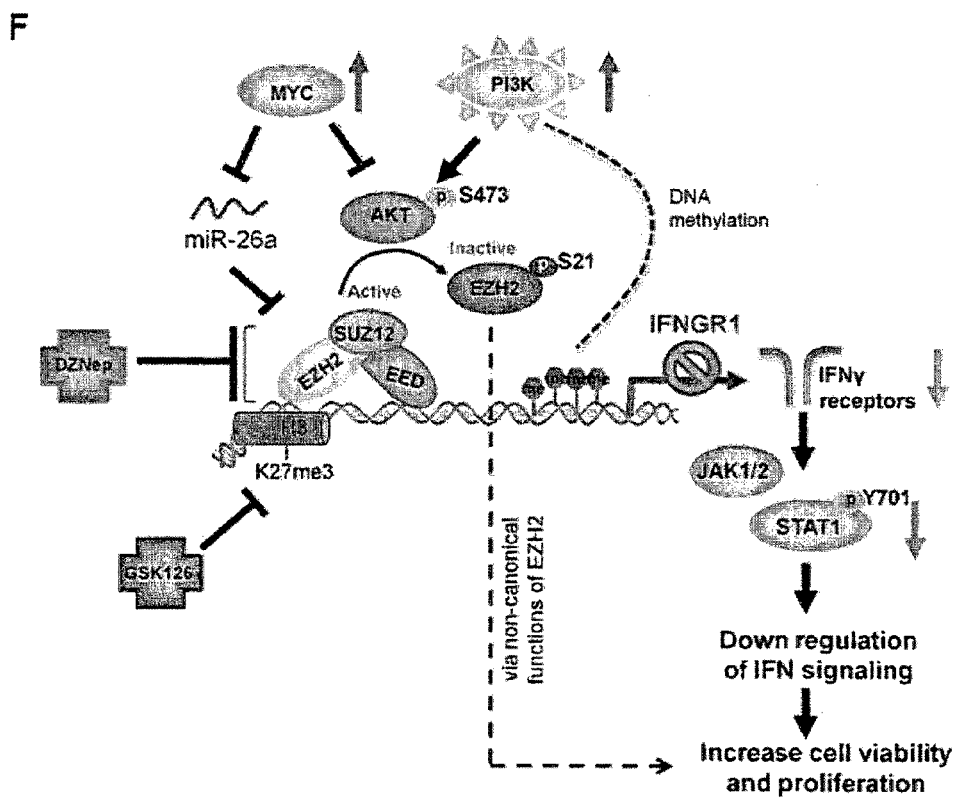

FIG. 7 is a series of analysis showing that catalytic inhibitors of EZH2 fail to recapitulate the EZH2 knockdown effects.

FIG. 7(A) is a series of western blot analysis of IFNGR1, PRC2 proteins and H3K27me3 in DU145 cells treated with DZNep, GSK343, or GSK126 at indicated doses for 3 or 10 days.

FIG. 7(B) is a histogram plot of qRT-PCR analysis of IFNGR1 expression in DU145 cells treated with indicated drugs for 3 or 10 days.

FIG. 7(C) is a histogram plot of ChIP analysis of EZH2 and H3K27me3 enrichments at IFNGR1 in DU145 cells treated with either DMSO, DZNep (2.5 μM) or GSK126 (5 μM) for 3 days. Enrichments were expressed as percentage of total input used for chromatin immuno-precipitation.

FIG. 7(D) is a histogram plot of a FACS sub-G1 DNA analysis in DU145 cells treated with DZNep, or GSK343/GSK126, in combination with IFN-γ as indicated.

FIG. 7(E) is a histogram plot of prostatosphere formation assay after treating DU145 cells with IFN-γ (25 ng/mL) and GSK126 for 10 days at doses as indicated.

FIG. 7(F) is a schematic cartoon model showing EZH2-mediated inactivation of IFN-JAK-STAT1 signaling regulated by MYC and PI3K-AKT. MYC overexpression leads to EZH2 activation through antagonizing miR-26a and PI3K-AKT-mediated EZH2 inhibition, resulting in suppression of IFNGR1 and the downsteam JAK-STAT1 signaling. DZNep depletion of EZH2/PRC2 restores IFNGR1 expression and synergizes with IFN-γ to induce growth inhibition and apoptosis.

All the data in the graph bars represent mean+SEM, n=3. *p<0.05, **p<0.01, n.s.=not significant.

Figure 8:
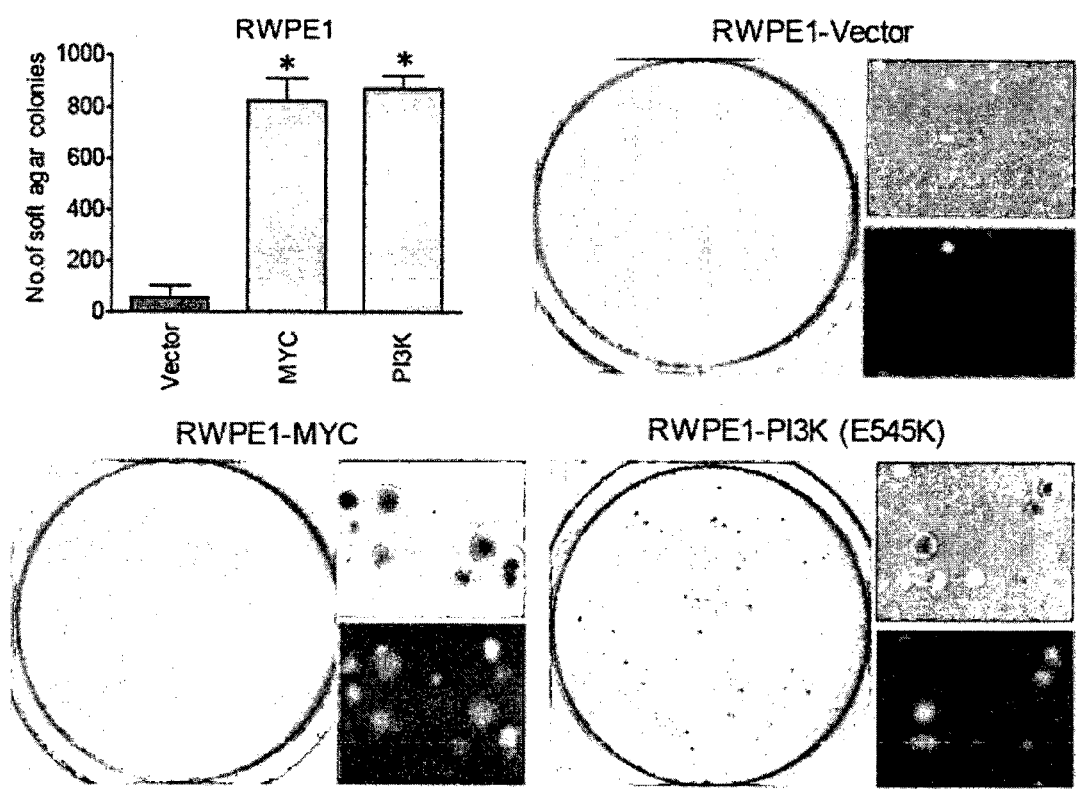

FIG. 8 is a graph and immunofluorescence and contrast microscope images validating the transformation induced by MYC and activated PI3K mutant in RWPE1 benign prostate epithelial cell line. On the top left corner is a histogram plot of a soft agar assay showing significant difference (*p<0.05) in anchorage independent growth of RWPE1-MYC and RWPE1-PI3K in comparison to RWPE1-Vector. Representative scanned image of the soft agar colonies (left), Phase-contrast microscopy image of the soft agar colonies taken at 4× magnification (top right), GFP fluorescent microscopy image of the soft agar colonies taken at 4× magnification (bottom right) showing the specificity of the overexpression.

Figure 9:
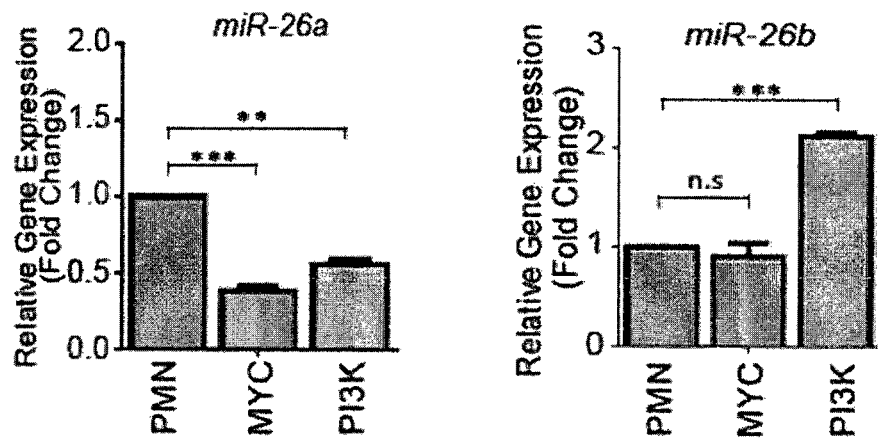
Figure 9:
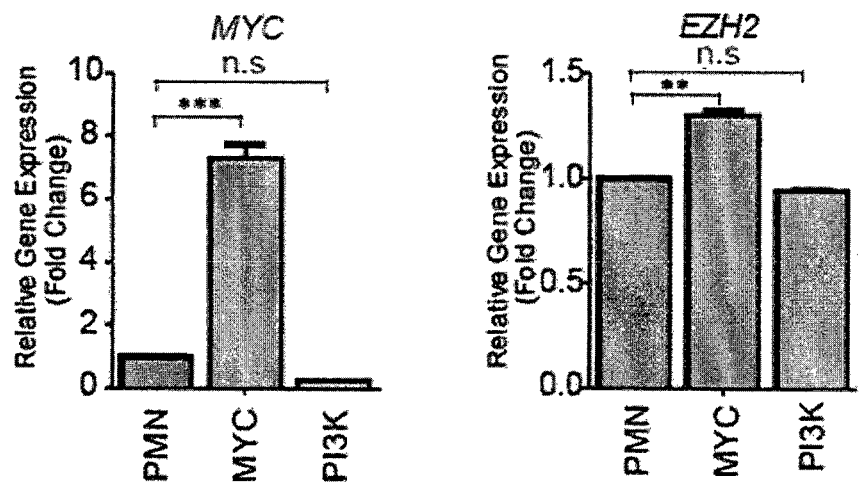
Figure 9:
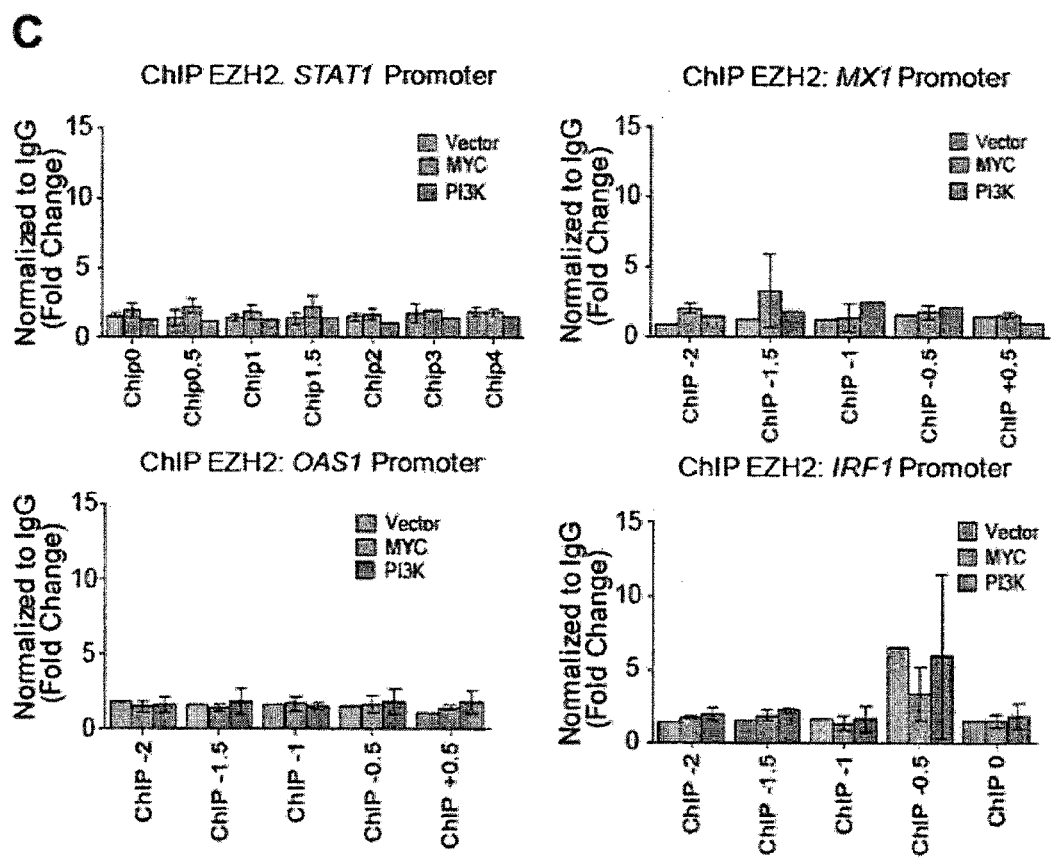
Figure 9:
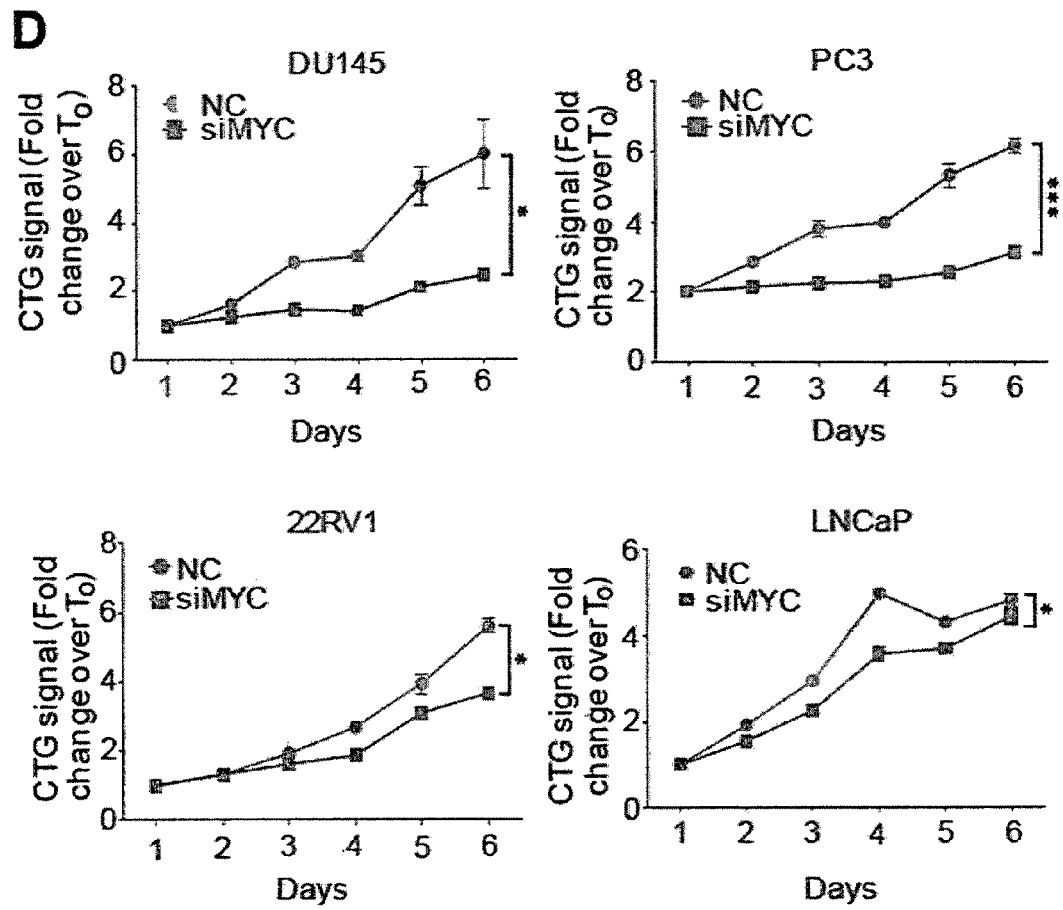
Figure 9:
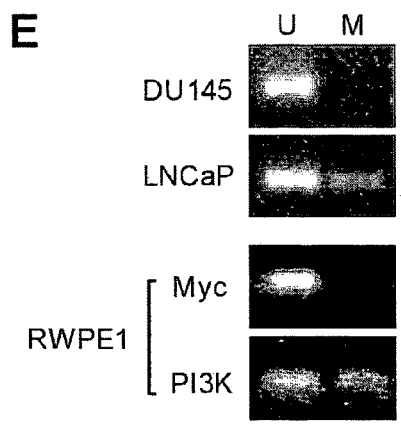

FIG. 9 is a series of graphs showing Myc overexpression in relation to miR-26a and EZH2 expression and the stratification of prostate cancer cells according to MYC dependency.

FIG. 9(A) is a pair of histogram plots of quantitative PCR analysis showing the reduction of endogenous microRNA miR-26a (left) expression in Myc overexpressing RWPE1 cells but not in miR-26b expression (right).

FIG. 9(B) is a pair of histogram plots of quantitative PCR analysis validating the over expression of Myc in RWPE1 cells that were infected with the retrovirally infected cells (left) and corresponding increase in EZH2 transcriptional expression (right).

FIG. 9(C) is a series of histogram plots of ChIP followed by qPCR indicating insignificant enrichment of EZH2 on promoters of various IFN-γ pathway activated genes in RWPE1-MYC, RWPE1-PI3K and RWPE1-Vector cells. Thus FIG. 9(C) indicates that downregulation of downstream IFN signaling genes is due to the EZH2-mediated repression of the IFN gamma receptor (IFNGR1) and that EZH2 do not affect other downstream IFN signaling genes.

FIG. 9(D) is a series of scatter plot of Cell Titer Glo proliferation assay measuring the growth of DU145, PC3, 22RV1 and LNCaP cells over 6 days in the presence or absence of siRNA against MYC expression. The growth of these cells was normalized and plotted as fold change against the Cell Titer Glo (CTG) signal on Day 0 ($T_0$).

FIG. 9(E) is a series of images of Methylation Specific PCR (MSP) analysis of IFNGR1 promoter in RWPE1 sublines and prostate cancer cell lines showing DNA methylation in LNCaP and RWPE1-PI3K cells but not in DU145 and RWPE1-Myc cells. (U is unmethylated promoter, M is methylated).

Figure 10:
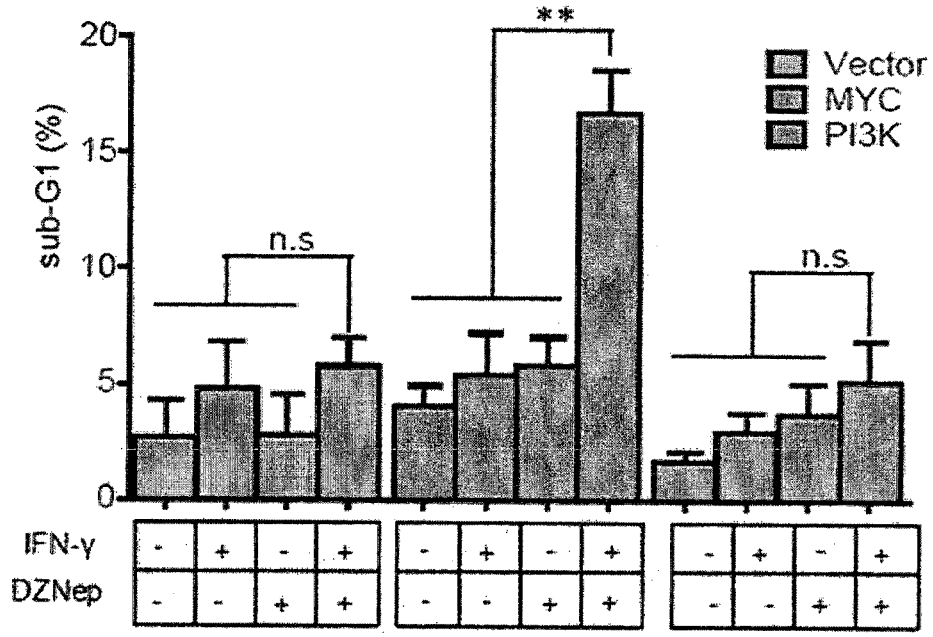
Figure 10:
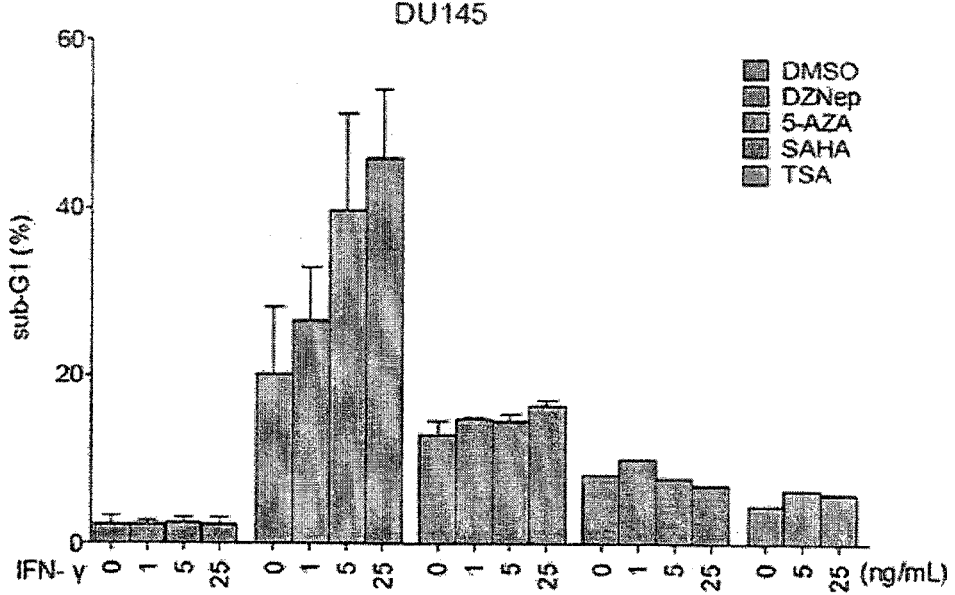
Figure 10:
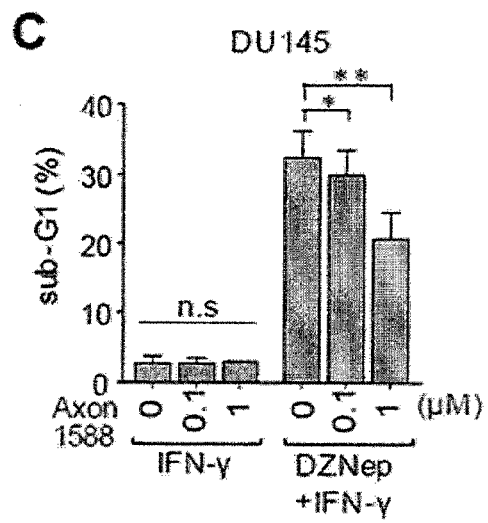
Figure 10:
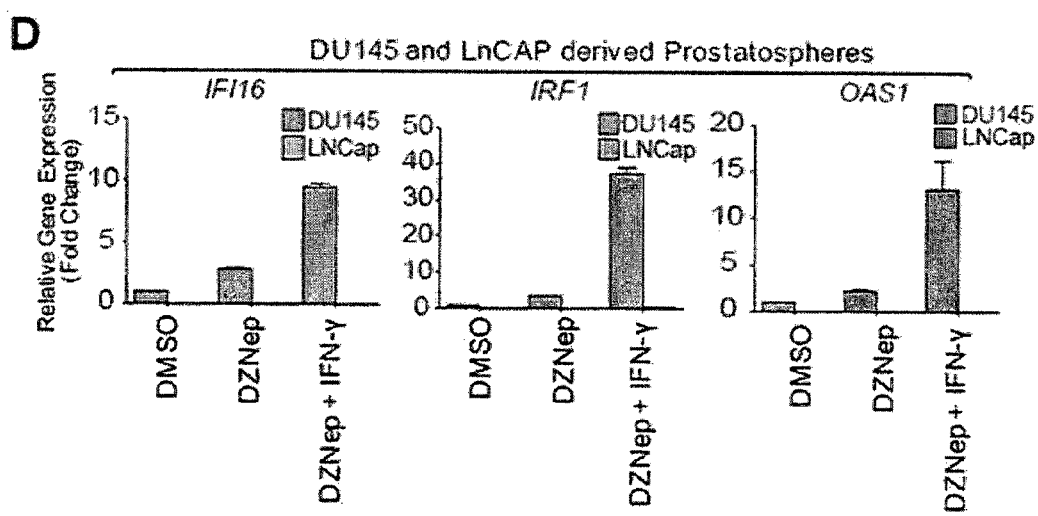

FIG. 10 is a series of graphs the effects of DZNep on apoptosis and IFN-γ stimulation.

FIG. 10(A) is a graph of FACS analysis demonstrating the synergistic effect between DZNep (2.5 μM) and IFN-γ to specifically induce cell death in RWPE1-MYC cells but not RWPE1-PI3K cells. Cells were treated with either DMSO or DZNep (2.5 μM) for 3 days with, increasing doses of IFN-γ. **p<0.01, n.s=not significant FIG. 10(B) is a graph of FACS analysis showing the synergistic induction of cell death in DU145 cells when DZNep (2.5 μM) was added in combination with IFN-γ but was not observed in other epigenetic inhibitors.

FIG. 10(C) is a graph showing a FACS-derived sub-G1 DNA analysis in DU145 cells treated with DZNep/IFN-γ in the presence or absence of JAK2 inhibitor Axon 1588.

FIG. 10(D) is a series of histogram plots of quantitative PCR analysis showing the enhanced response to IFN-γ stimulation after DZNep treatment as reflected by the upregulation of IFN responsive genes, IF116, IRF1 and OAS1 in DU145 cells but not LNCaP cells derived prostatospheres.

Figure 11:
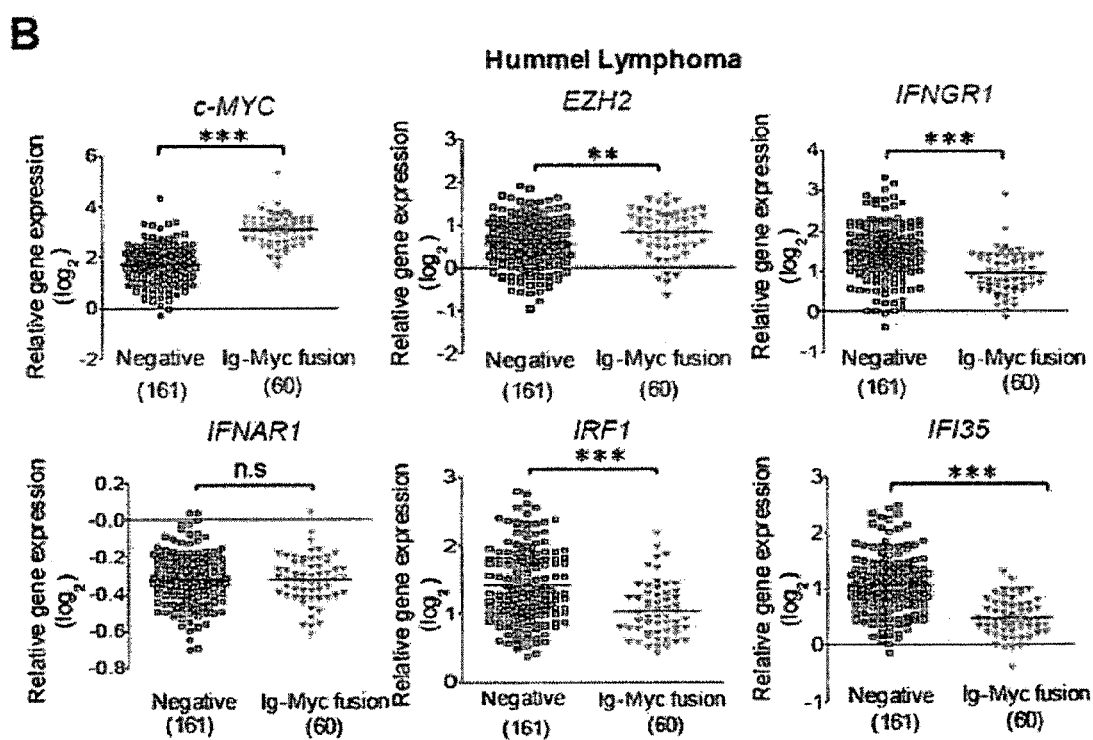

FIG. 11 is a series of heatmaps and graphs showing the inverse relationship between EZH2 and IFNGR1 expression observed in multiple human cancers, including MYC driven Burkitt's lymphoma.

FIG. 11(A) is a table summarizing of an oncomine analysis showing the upregulation of EZH2 was companied by the down regulation of IFNGR1 in many datasets of different cancer types.

FIG. 11(B) is a series of dot plots showing the mRNA expression (Log 2) of EZH2, MYC, IFNGR1 and IFN responsive genes (IRF1 and IF135) in lymphoma tumors with or without Ig-MYC fusion extracted from the Hummel Lymphoma dataset (p<0.01, *p<0.001, n.s=not significant, unpaired two tailed student's t-test).

Figure 12:
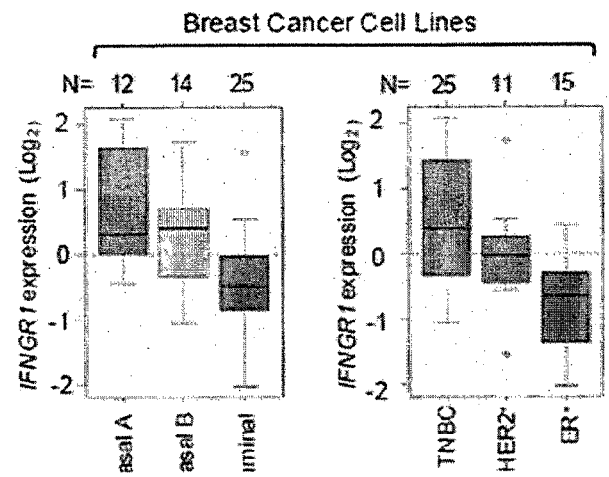
Figure 12:
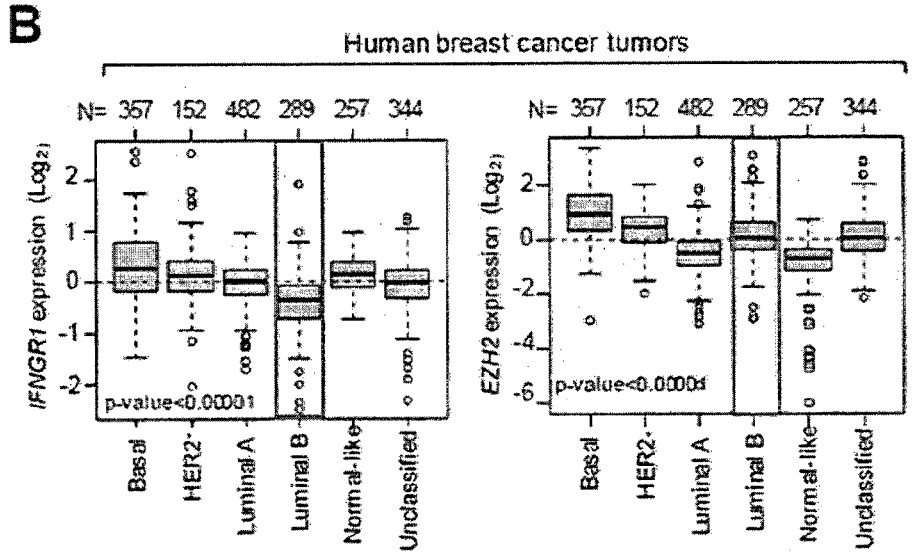
Figure 12:
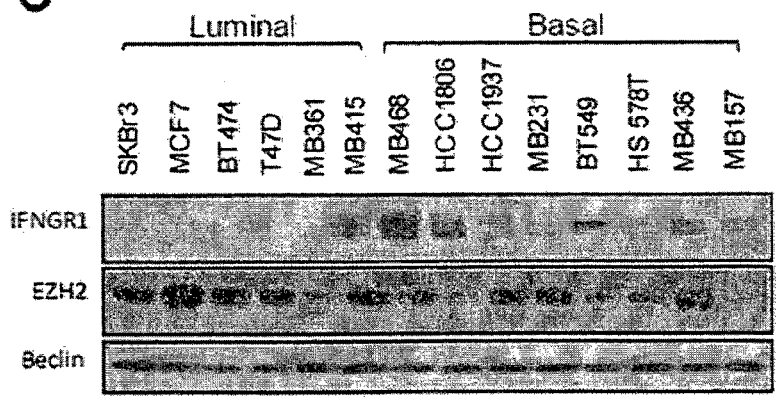
Figure 12:
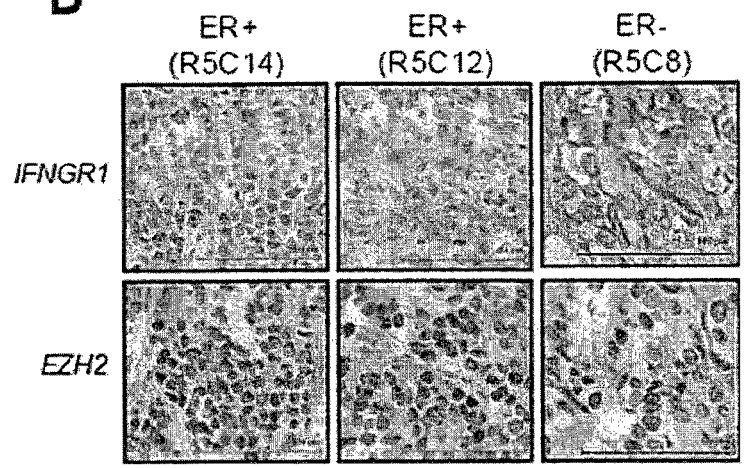
Figure 12:
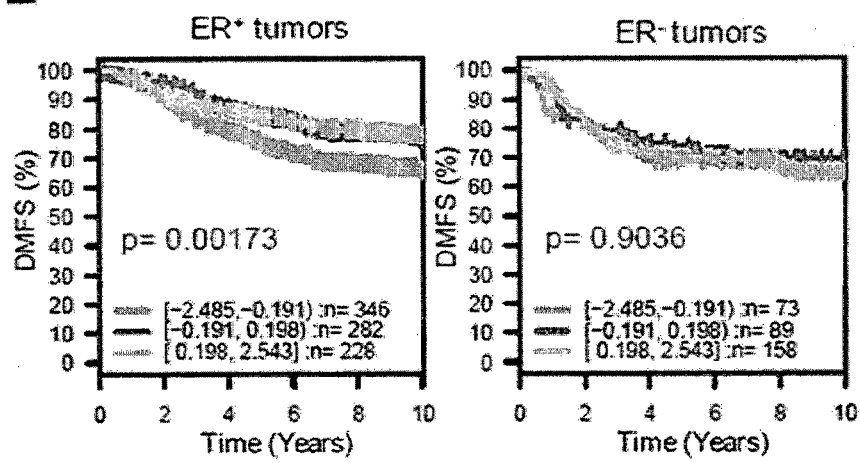
Figure 12:
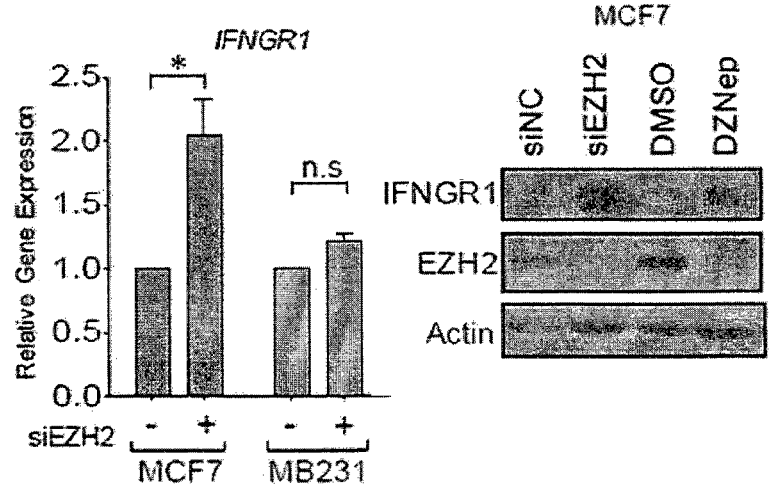
Figure 12:
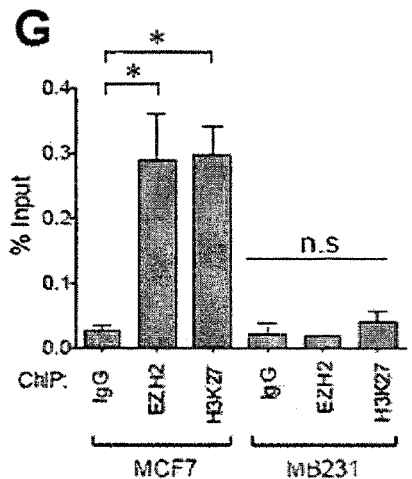
Figure 12:
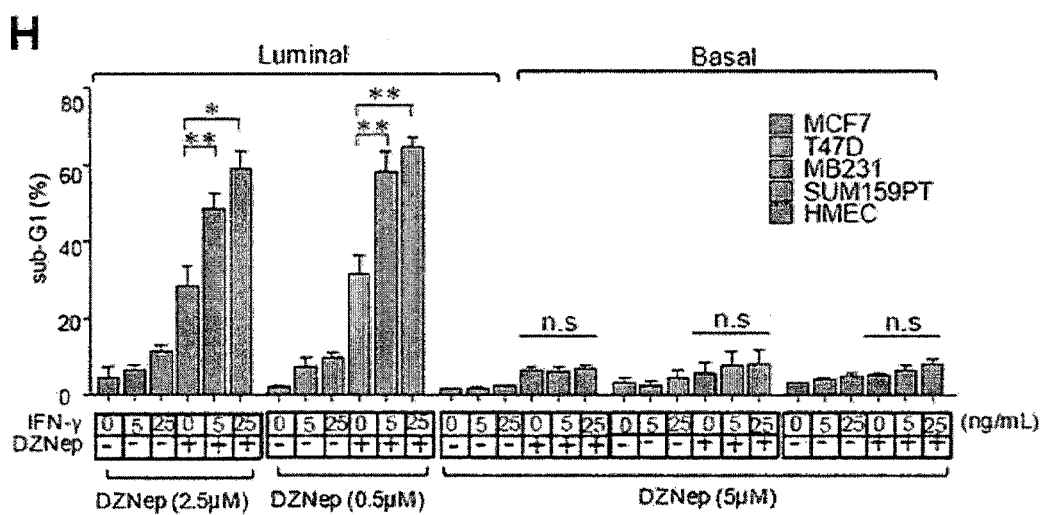
Figure 12:
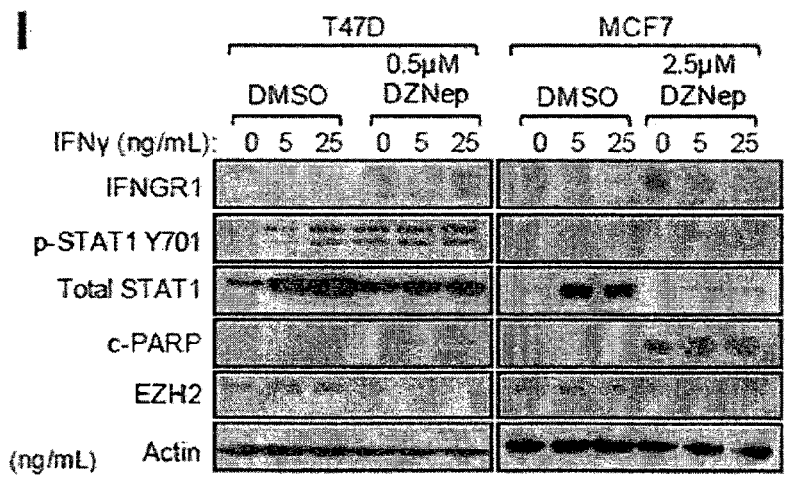

FIG. 12 is a series of graphs, western blots and IHC analysis showing how EZH2 represses IFNGR1 expression in luminal breast cancer.

FIG. 12(A) is a pair of box plots generated from GOBO analysis on a panel of breast cancer cell lines illustrating that the IFNGR1 expression is significantly lower in luminal and ER+ breast cancer cell lines as compared to other subtypes of breast cancer cell lines.

FIG. 12(B) is a pair of box plots generated from GOBO analysis showing the mRNA expression (Log 2) of IFNGR1 (left) and EZH2 (right) in a dataset containing 1881 breast tumor samples which were further categorized according to their molecular subtype. Error bars, mean±s.e.m.

FIG. 12(C) is a series of western blot analysis of IFNGR1 and EZH2 expression in a panel of luminal and basal-like breast cancer cell lines.

FIG. 12(D) is a series of representative IHC imaging showing IFNGR1 and EZH2 expression in ER+ and ER− breast tumors. Coordinates of the tumor samples in the TMA slide were as indicated in parentheses. Scale bar=100 μm.

FIG. 12(E) is a pair of Kaplan-Meier analysis of distant metastasis free survival (DMFS) of breast cancer patients with low (Grey), intermediate (Red) or high (Blue) level of IFNGR1 expression in ER+ vs. ER− tumors.

FIG. 12(F) is a graph and western blot showing (Left) qRT-PCR analysis of IFNGR1 mRNA in MCF7 and MB231 cells treated with siEZH2 (*p<0.05) and (right) western blotting of IFNGR1 and EZH2 in MCF-7 cells treated with siEZH2 or DZNep.

FIG. 12(G) is a histogram plot of a ChIP analysis using EZH2 and H3K27me3 enrichments in the IFNGR1 promoter in MCF7 and MB231 cells. The enrichment is expressed as a percentage of the total DNA input.

FIG. 12(H) is a graph of a FACS generated sub-G1 DNA analysis of a panel of breast cancer cell lines treated with DZNep in combination with IFN-γ as indicated.

FIG. 12(I) is a series of western blotting analysis of the indicated proteins in MCF7 and T47D cells treated with the indicated amount of DZNep, IFN-γ, or a combination of both. DMSO was used as a solvent and thus is used as a negative control.

Figure 13:
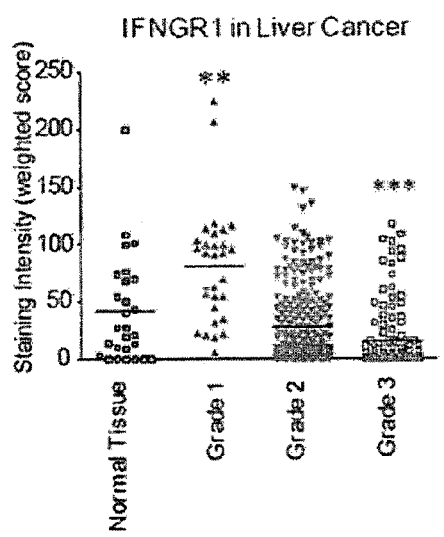
Figure 13:
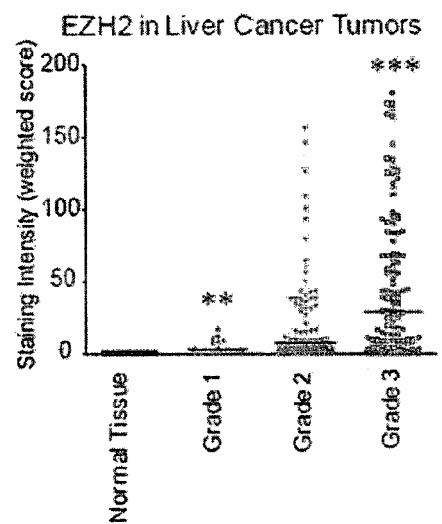
Figure 13:
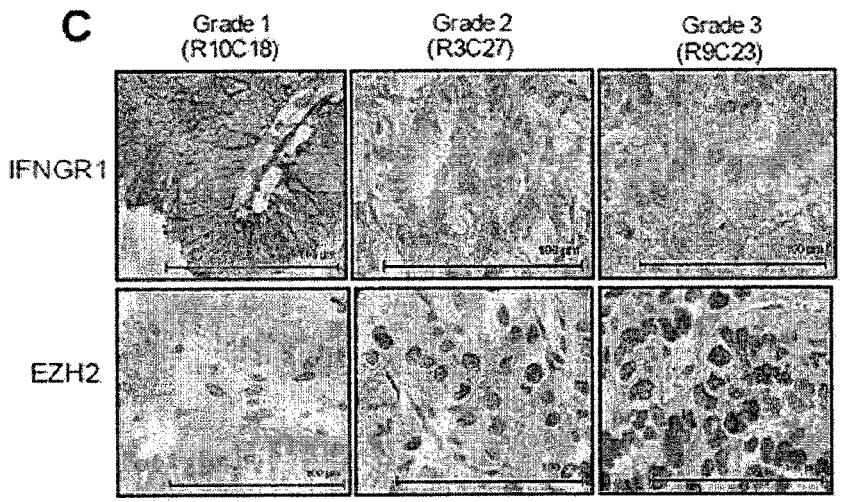
Figure 13:
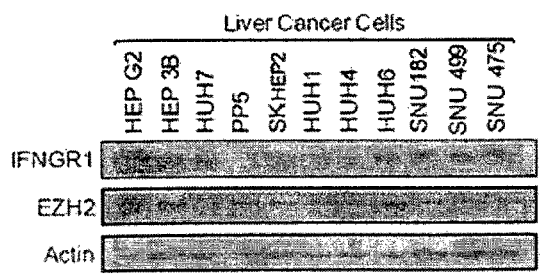
Figure 13:
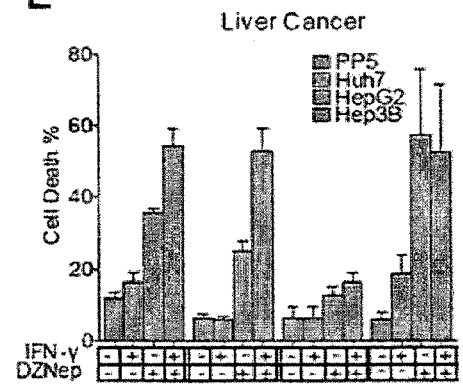

FIG. 13 is a series of box plots, IHC images and graphs demonstrating EZH2-mediated downregulation of IFNGR1 in liver cancer.

FIGS. 13 A and B are a pair of dot plots generated after quantifying the intensity of immunochemical staining of liver cancer tissue microarray (TMA) illustrating the inverse correlation between the protein expression (A) IFNGR1 and (B) EZH2 in liver cancer tumors as the disease progresses in clinical grade. (*$p<0.05$, $p<0.01$, *$p<0.001$, n.s.=not significant, two-tailed student's t-test).

FIG. 13(C) is a series of representative images of immune-histochemical staining of liver cancer tissue microarray (TMA) used to generate the plots described above. Representative images of the liver cancer TMA-IHC staining (20× magnification) showing the downregulation of IFNGR1 in liver cancer tumors with different clinical grading. Scale bars=100 μM.

FIG. 13(D) is a western blotting analysis showing the inverse correlation between protein expression level of IFNGR1 and EZH2 in a panel of liver cancer cell lines with high expression of EZH2.

FIG. 13(E) is a graph of a FACS generated sub-G1 DNA analysis of a panel of liver cancer cell lines treated with DZNep alone or in combination with IFN-γ as indicated. The FACS analysis illustrates the synergistic effect between DZNep and IFN-γ, to induce robust cell death in several liver cancer cell lines.

Figure 14:
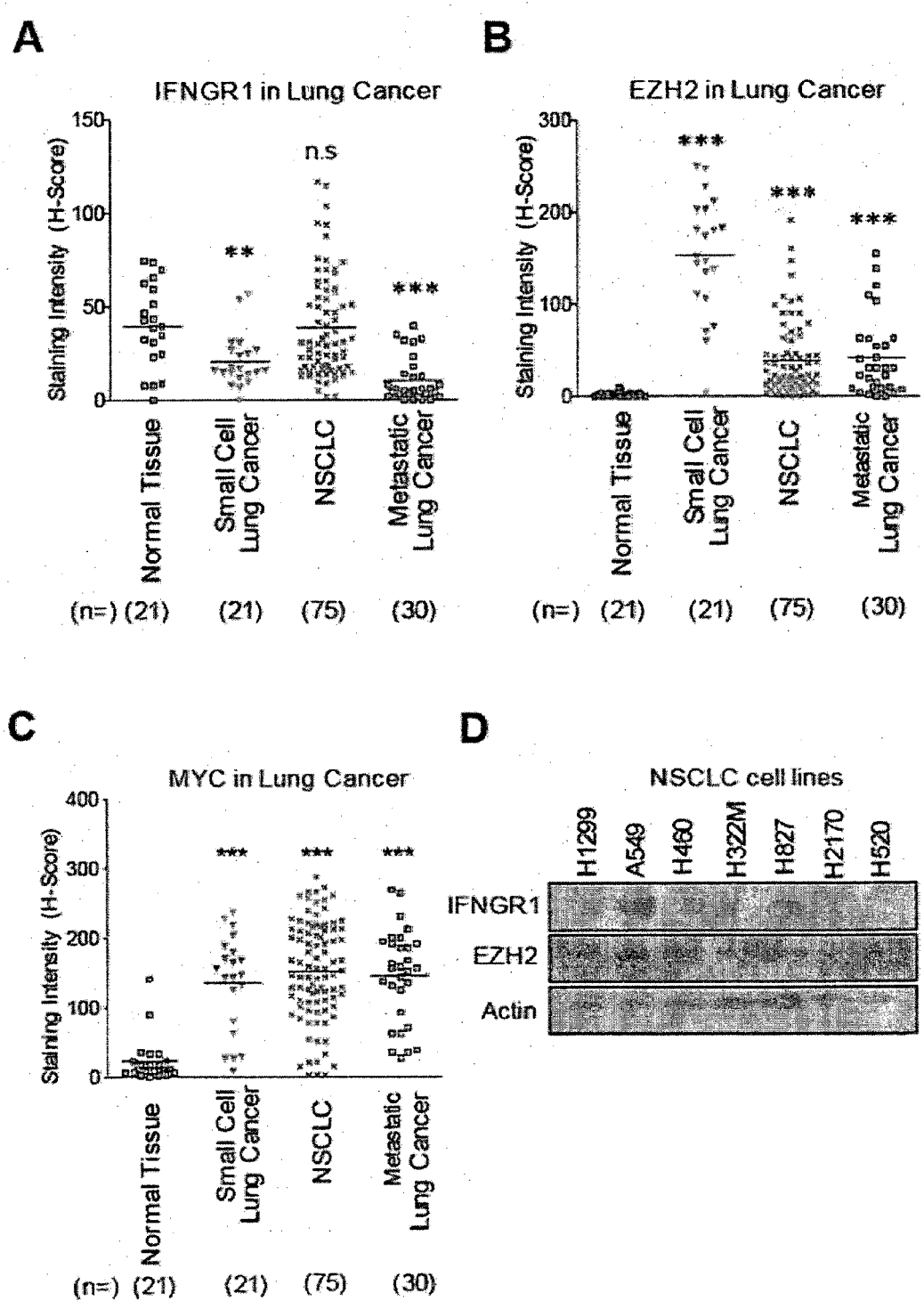
Figure 14:
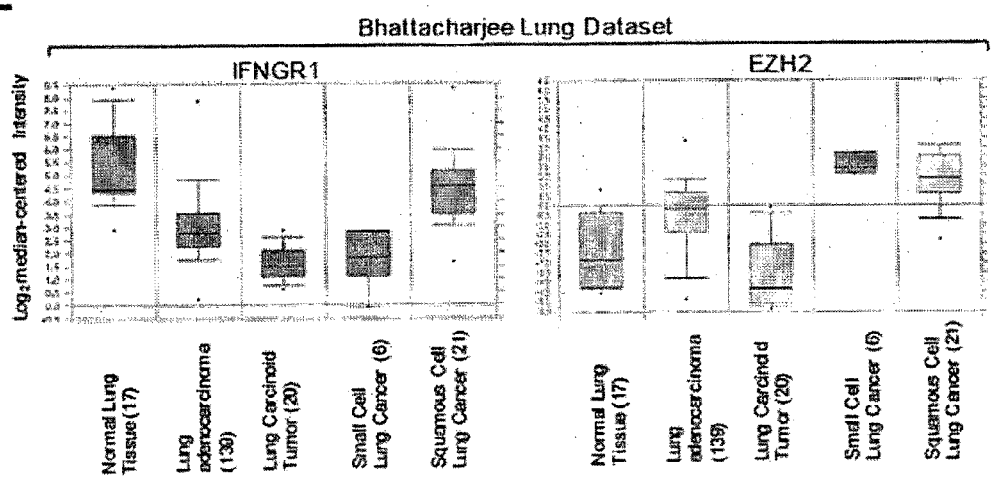
Figure 14:
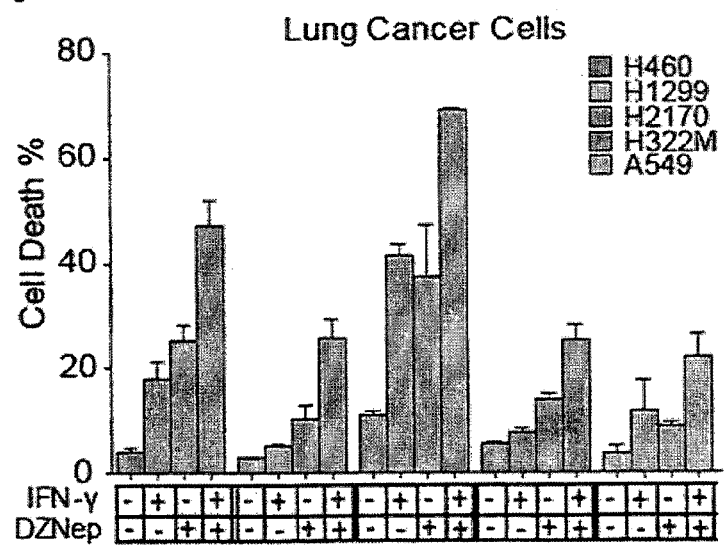
Figure 14:
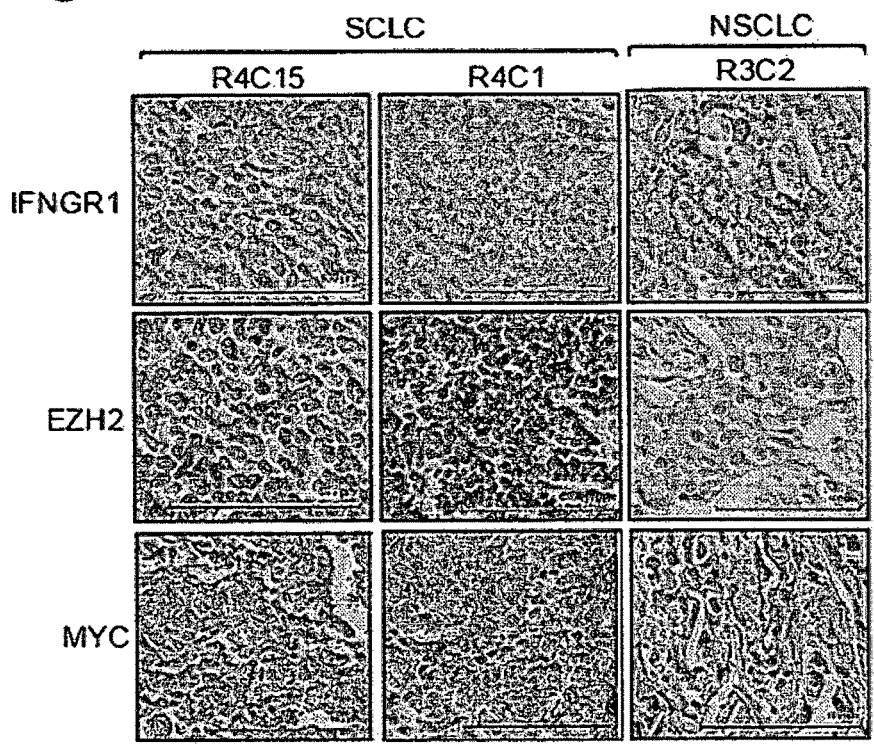
Figure 14:
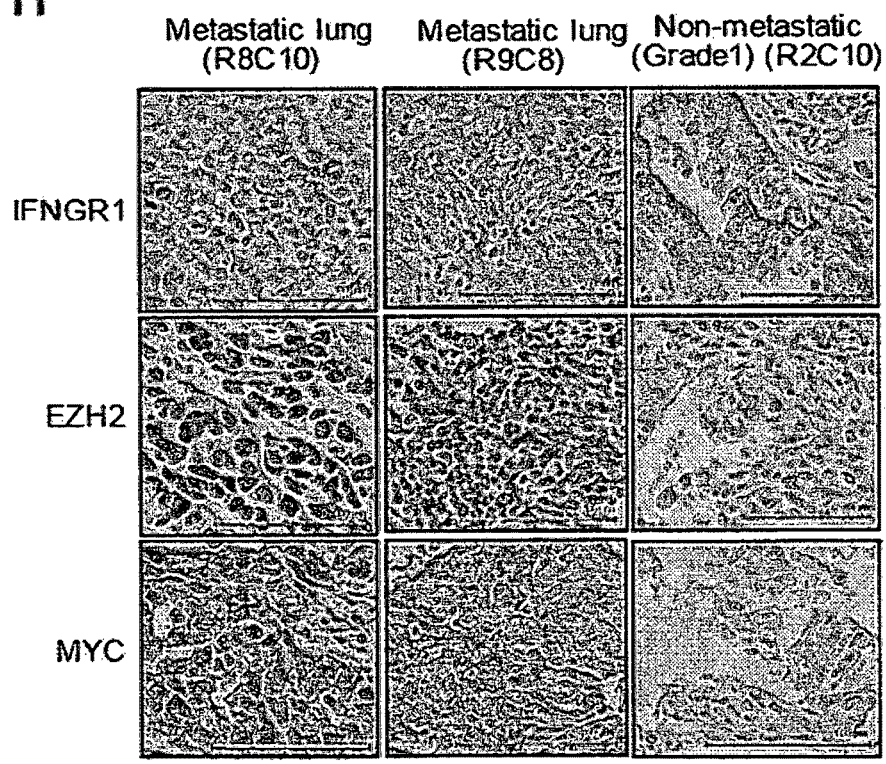

FIG. 14 is a series of scatter plots, western blots and IHC demonstrating EZH2-mediated downregulation of IFNGR1 in lung cancer.

FIGS. 14(A, B & C) is a series of scatter plots generated after quantifying the intensity of immunochemical staining of liver cancer tissue microarray (TMA) illustrating the inverse correlation between the protein expression (A) IFNGR1, (B) EZH2 and (C) MYC in different subtypes of lung cancer tumors. ($p<0.01$, *$p<0.001$, n.s.=not significant, two-tailed student's t-test)

FIG. 14(D) is a western blotting analysis showing the inversely related protein expression of IFNGR1 and EZH2 in a panel of lung cancer cell lines.

FIG. 14(E) is a pair of box plots generated from the oncomine analysis of the Bhattacharjee lung dataset showing that upregulation of (right) EZH2 is accompanied by the down regulation of (left) IFNGR1, particularly so in small cell lung cancer tumors.

FIG. 14(F) is a histogram plot generated from a FACS analysis of sub-G1 contents illustrating the synergistic effect between DZNep and IFN-γ to induce robust cell death in several lung cancer cell lines.

FIG. 14(G) is a series of representative images of lung cancer TMA-IHC staining showing downregulation of IFNGR1 in small cell lung cancer tumors with high levels of EZH2 and MYC protein expression. Scale bars=100 μM.

FIG. 14(H) is a series of representative images of lung cancer TMA-IHC staining showing the downregulation of IFNGR1 in metastatic lung cancer with high levels of EZH2 and MYC. Scale bars=100 μM.

DETAILED DESCRIPTION OF THE PRESENT INVENTION

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used herein, the singular form "a," "an," and "the" include plural references unless the context clearly dictates otherwise. For example, the term "an agent" includes a plurality of agents, including mixtures thereof and reference to "the nucleic acid sequence" generally includes reference to one or more nucleic acid sequences and equivalents thereof known to those skilled in the art, and so forth.

As used herein, the term "comprising" means-"including". Thus, for example, a composition "comprising" X may consist exclusively of X or may include one or more additional components.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The present disclosure relates to pharmaceutical compositions and therapies for cancer, such as for example, prostate cancer, breast cancer including but not limited to luminal B breast cancer, liver cancer, ovarian cancer, acute lymphoblastic leukemia (ALL).

During development, a cell's fate is decided by the initial gene expression. After acquiring its fate and position, this cellular identity is maintained by keeping some genes "on" and others "off". This transcriptional "memory" if perturbed can lead to severe developmental defects. If the maintenance mechanism fails, cells may lose their capacities of proliferation, differentiation, adhesion or invasion. Among other hallmarks, cancer is a result of defects in maintaining the cellular transcriptional memory, leading to lack of differentiation, or anaplasia. Hence, dysregulation of the transcriptional maintenance system can lead to malignancy.

The Polycomb Group (PcG) and trithorax Group (trxG) have been implicated in maintenance of the cellular memory and prevent changes in cell type specific transcription programs. They are known to be involved in the process of histone modification, DNA methylation and chromatin transformation. To establish and maintain the cell identity, many pathways are involved in repressing specific sets of genes. From *Drosophila* to mammals, the genes of Polycomb group and trithorax group are widely conserved and they maintain the transcription patterns which are set in the first stages of embryonic life, and in the adulthood. TrxG and PcG respectively regulate active and repressed genes related to development and cell cycle regulation. Multiple lines of evidence show that PcG proteins are dysregulated and play important roles in cancer progression.

Among various epigenetic modifying enzymes, the Polycomb repressor complex 2 (PRC2) is of particular importance since its key component EZH2, a histone methyltransferase specific for repressive H3K27 trimethylation (H3K27me3), is often deregulated in human cancers. The role of EZH2-mediated gene silencing has been implicated in regulating cancer cell proliferation, invasion and metastasis. Moreover, increasing number of EZH2 or H3K27me3 target genes linked to important cancer pathways have been recently identified. EZH2 is overexpressed in hormone-refractory, metastatic prostate cancer, and is a biomarker of prostate metastases. Hence, EZH2 and its associated histone methyltransferase activity in the majority of cancers, which suggest that EZH2 enzymatic activity is a promising cancer drug target.

EZH2 inhibitors such as for example, S-adenosylhomocysteine hydrolase (SAHH) inhibitor 3-deazaneplanocin A (DZNep) that can modulate histone methylation and disrupt EZH2 complex, have been shown to induce apoptosis in some cancer cell lines. However, DZNep has numerous side effects and produces widely varied response in a cancer-specific manner. The term "inhibitor" or "antagonist" is used in the broadest sense herein, and is understood to include all molecules that partially or entirely block, inhibit, and/or neutralize at least one biological activity of their target (e.g., EZH2). For example, the term "antagonist antibody" refers to an antibody that inhibits or decreases the biological activity of an antigen, for example EZH2, that the antibody binds. In some examples, the antibody or the antigen binding fragment thereof specifically binds to EZH2 to reactivate expression of genes repressed by EZH2 of genes, thereby, for example, inhibiting proliferation of the target tumor cell.

It is thus an object of the invention to develop combinatorial pharmacologic approaches for epigenetic gene reactivation. Without being bound by any theories, the present inventors surprisingly found that IFNGR1, the gene that encodes for interferon-gamma receptor gamma subunit has frequently been observed to be down-regulated in as significant number of prostate cancer cell lines and advanced prostate cancer tumours. As indicated above, IFN-γ, the naturally occurring ligand of IFNGR1, has been previously used as an anti-tumour agent to treat cancers including prostate cancer but with limited success.

In the present disclosure, it is shown that down-regulation of the IFNGR1 receptor leads to desensitization of cancer cells to an enhancer of interferon-gamma receptor activity treatment, such as IFN-γ treatment. Since the IFN-γ pathway can only be specifically be activated the IFN-γ ligand, the non-responsiveness to IFN-γ treatment due to the absence or low number of INFGR1 allows the prostate cancer cells to evade cell death by reduced activation of the IFN-γ-STAT1 tumour suppressor pathway.

Advantageously, the inventors further identified EZH2 to be an epigenetic factor that mediates the repression of genes including but not limited to IFNGR1 (encoding for IFN-γ Receptor subunit 1), IFNAR2, IF116, IFNAR1, IFNGR2, IFIT1, GBP1, IRF9, STAT2, IFIH1, STAT1, MX1, IFIT2, IF116, IF144, IFIT3 and ISG15 in highly metastatic prostate cancer cells. Other exemplary representative genes are shown in Table 2 below. Additionally, the inventors found that in addition to prostate cancer, IFNGR1 level is also downregulated in cancers including but not limited to liver, lung, breast, leukemia such as ALL ovarian, and cancers when compared to IFNGR1 level in normal (non-tumour or non-cancerous cells, tissues, organs or organisms).

Accordingly, in one example there is provided a pharmaceutical composition comprising a histone-lysine N-methyltransferase EZH2 (enhancer of zeste homolog 2) inhibitor and an enhancer of interferon-gamma receptor activity. In another example, disclosed herein is the pharmaceutical composition described herein, wherein the interferon-gamma receptor can be the interferon-gamma receptor 1 (IFNGR1) encoding for interferon-gamma receptor (IFNGR1) subunit 1. In a further example, the interferon gamma receptor can be the interferon-gamma receptor 2 (IFNGR2) encoding for interferon-gamma receptor (IFNGR1) subunit 2. In one example, disclosed is the pharmaceutical composition described herein, further comprising one or more pharmaceutically acceptable excipients, vehicles or carriers. As used herein, the term "enhancer" is used in its broadest sense and is understood to include all molecules that partially or entirely activate, improve, and/or enhance at least one biological activity of their target (e.g., interferon-gamma receptor). The enhancer can act directly (e.g. by binding to the receptor) or indirectly (e.g. by inhibiting molecules that interfere with the activity of the interferon-receptor, such as IFNGR1, or by improving the binding of a ligand to the receptor).

As used herein, the term "pharmaceutical composition" refers to the presence of at least one histone-lysine N-methyltransferase EZH2 (enhancer of zeste homolog 2) inhibitor and at least one an enhancer of interferon-gamma receptor activity as defined herein. Thus, a pharmaceutical composition of the invention may comprise two or more histone-lysine N-methyltransferase EZH2 (enhancer of zeste homolog 2) inhibitors comprising but not limited to a small molecule inhibitor of EZH2, such as the inhibitors described in Table 1, a EZH2 binding protein, such as an antibody, and a nucleic acid molecule or conjugate thereof capable of inhibiting the expression of EZH2, such as a siRNA, a miRNA or an aptamer and two or more enhancer of interferon-gamma receptor activity comprising but not limited to a small molecule enhancer, IFN-γ, a IFNGR1-binding molecule, such as a peptide, a protein or a nucleic acid. For example, the pharmaceutical composition as disclosed herein may comprise a combination of DZNep and a siRNA capable of binding and inhibiting translation of EZH2 mRNA and a combination of IFN-γ and a molecule capable of neutralizing and inhibiting binders of IFN-γ. By binder of IFN-γ, it is meant any molecule capable of binding IFN-γ that may inhibit its ability to bind to its receptor IFNGR1. Such molecules may include proteins such as enzymes (e.g. proteases), antibodies, or peptides. The pharmaceutical composition may further optionally comprise at least one pharmaceutically acceptable carrier, diluent, vehicle or excipient.

As used herein, the term "pharmaceutically acceptable carrier", "pharmaceutically acceptable vehicle" or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in subjects, preferably humans. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

A compound or compounds as described herein, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w).

The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or *acacia*. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

Advantageously, the present disclosure shows that IFNGR expression (e.g. IFNGR1 expression) can be restored in diseased cells where expression of IFNGR is absent or downregulated because of EZH2 overexpression. The inventors surprisingly found that EZH2 overexpression results in repression of IFNGR expression. Hence, the subsequent absence or low numbers of IFNGR receptors at the surface of the diseased cells, such as for example, cancer cells may lead to unresponsiveness of cells to IFN-γ stimulation. In turn, the IFN-γ-STAT1 tumour suppressor pathway may not be activated by IFN-γ.

Thus, the present disclosure relates to the restoration of INFGR expression through reactivation (or derepression) of interferon-gamma receptor gene, by inhibition of EZH2 enzyme. In one example, the present invention discloses a pharmaceutical composition that may comprise at least one EZH2 inhibitor, thereby for example restoring the EZH2-mediated repression of IFNGR expression such as INFGR1 and at least one enhancer of interferon gamma activity, to reactivate the receptors that Examples of EZH2 inhibitors are presented below and may include but are not limited to small chemical molecules (or agents or drugs) inhibitors that inhibit the activity of EZH2, molecules that inhibit the expression of EZH2, such as siRNA, miRNA or aptamers, or antibodies that bind EZH2, thereby inhibiting the EZH2-mediated repression of INFGR, such as INFGR1 in affected cells. Advantageously, the restoration of INFGR1 through EZH2 may not require amount or dosage of EZH2 inhibitor that would lead to potential detrimental side effects to the patient. The present technology proposes treatment and diagnosis of advanced prostate cancer and other cancers comprising the use of EZH2 inhibitors in combination with IFN-γ.

In one example, there is provided an inhibitor of EZH2 including but not limited to the small molecules inhibitors presented in Table 1 below.

TABLE 1

Small molecules EZH2 inhibitors
EZH2 Inhibitors (−)-1-[(1R,4R,5S)-3-(Hydroxymethyl)-4,5-dihydroxy-2-cyclopenten-1-yl]4-aminoimidazo[4,5-c]pyridine hydrochloride (DZNep; 3-deazaneplanocin A)
1-{[4-amino-5-(2,2-dimethylpropanoyl)-1,3-thiazol-2-yl]sulfanyl}-3,3-dimethylbutan-2-one
4-[4-(4-methyl-1,3-thiazol-2-yl)phenyl]-1,2,3-thiadiazole
2-{[(3,4-dichlorophenyl)carbamoyl]amino}benzoic acid
N-(2-methylquinolin-6-yl)quinoxaline-2-carboxamide
2-[(4-tert-butylphenyl)carbonyl]-1H-imidazole
1-(2-hydroxyphenyl)-3-[4-(methoxymethoxy)phenyl]propane-1,3-dione
N-(3-acetylphenyl)-8-methoxy-2-oxo-2H-chromene-3-carboxamide
1-{3-[4-(2-phenylethynyl)phenyl]-1H-pyrazol-1-yl}ethan-1-one
3-(thiophen-2-yl)benzoic acid
5-(6-methoxynaphthalen-2-yl)-1H-pyrazole
4-methyl-5-[3-(methylsulfanyl)-1H-pyrazol-5-yl]-2-(thiophen-2-yl)-1,3-thiazole
2-{[(2-chloro-6-fluorophenyl)methyl]sulfanyl}-1-(2,3-dihydro-1,4-benzodioxin-6-yl)ethan-1-one
3-(3-chlorophenyl)-5-(thiophen-3-yl)-1,2,4-oxadiazole
2,3-dihydro-1-benzofuran-5-ylmethanimidamido thiophene-2-carboxylate
N-(2,3-dihydro-1,4-benzodioxin-6-yl)[(furan-2-ylmethyl)carbamothioyl]formamide
N-[4-(diethylamino)phenyl]-3-methylbenzamide
3-[5-(1,2-oxazol-3-yl)thiophen-2-yl]-5-phenyl-1,2,4-oxadiazole
ethyl(2E)-2-cyano-3-{[(E)-{[4-dimethylamino)phenyl]methylidene}arnino](methane)sulfinirnidamido}prop-2-enoate
(2Z)-2-(4-ethylphenyl)-3-(4-methoxyphenyl)prop-2-enenitrile
5-tert-butyl-3-methyl-N-phenylthieno[3,2-b]thiophene-2-carboxamide
5-(1-butyl-2-oxo-2,3-dihydro-1H-indol-3-ylidene)-2-(piperidin-1-yl)-4,5-dihydro-1,3-thiazol-4-one
(2E,6E)-2,6-bis(thiophen-2-ylmethylidene)cyclohexan-1-one
2-[(E)-2-(3,4-dimethoxyphenyl)ethenyl]-1,3-benzothiazole
2-chloro-N-[3-hydroxy-4-(5-methyl-1,3-benzoxazol-2-yl)phenyl]-5-nitrobenzamide
6-chloro-2-phenyl-4H-thiochromen-4-one methyl 2-(3,4-dihydro-2H-1,5-benzodioxepine-7-amido)benzoate
3-chloro-N,N-dimethyl-4-[(1 E)-[2-(quinoxalin-2-yl)hydrazin-1-ylidene]methyl]aniline
(2E)-1-(2-methyl-1H-indol-3-yl)-3-(thiophen-2-yl)prop-2-en-1-one
N-(2,3-dihydro-1,4-benzodioxin-6-yl)-2-(thiophen-2-yl)-1,3-thiazole-4-carboxamide
4-[(E)-2-(1-methyl-1H-1,3-benzodiazol-2-yl)ethenyl]-1,3-thiazole
3-(4-bromophenyl)-3,4-dihydro-1,2,3-benzotriazin-4-one
N-(2,4-dichlorophenyl)-3,4-dihydro-2H-1-benzopyran-2-carboxamide
N,N-dimethyl-4-[(E)-2-phenylethenyl]aniline
2-(3,4-dichlorophenyl)quinoxaline
N-(3-tert-butyl-1H-pyrazol-5-yl)-2,3-dihydro-1,4-benzodioxine-2-carboxamide
(2E)-2-(1,3-benzothiazol-2-yl)-3-(4-chlorophenyl)prop-2-enenitrile
(4-tert-butylphenyl)methanimidamido 2-(thiophen-2-yl)acetate
5-[4-(3-methyl-1-benzothiophen-2-yl)-1,3-thiazol-2-yl]-1,2-oxazole
1-(4-fluorophenyl)-3-(1-phenyl-5-propyl-1H-pyrazol-4-yl)urea
2-[(2Z)-2-phenyl-2-[(2E)-2-(thiophen-2-ylmethylidene)hydrazin-1-ylidene]ethyl]-1H-1,3-benzodiazole
N-{7-oxo-8-oxa-4-thiatricyclo[7.4.0.0^{2,6}]trideca-1(9),2,5,10,12-pentaen-5-yl}thiophene-2-carboxamide
2-(2-chlorophenyl)-1-[4-(dimethylamino)phenyl]ethan-1-one ethyl 4-cyano-1-(4-methylphenyl)-1H-pyrazole-3-carboxylate
3-hydrazinylquinoxaline-2-thiol
1-[(5-tert-butylthiophen-2-yl)carbonyl]piperidine
3-[5-(2-phenylethynyl)thiophen-2-yl]-1-(thiophen-2-ylcarbonyl)-1H-pyrazole TABLE 1-continued Small molecules EZH2 inhibitors
EZH2 Inhibitors 2,5-dichloro-N-(2,3-dihydro-1,4-benzodioxin-2-ylmethyl)thiophene-3-carboxamide
1-tert-butyl-N-(2,3-dihydro-1,4-benzodioxin-6-yl)-5-methyl-1H-pyrazole-3-carboxamide
4-(5-propylpyridin-2-yl)benzonitrile
5-(4-chlorophenyl)-3-(2,2-dichloroacetamido)thiophene-2-carboxamide
(4-methanesulfonamidophenyl)methanimidamido thiophene-2-carboxylate
ethyl 7-methyl-2-phenylpyrazolo[1,5-a]pyrimidine-6-carboxylate
6-(4-chlorophenyl)-3-phenylthieno[2,3-e][1,2,4]triazine
1-{1-phenyl-1H-pyrazolo[3,4-d]pyrimidin-4-yl}-2,3-dihydro-1H-indole
5-(4-chlorophenyl)-2-(4-methylphenyl)-2H-1,2,3,4-tetrazole
4-[(1 E)-[2-(3,5-dichloropyridin-4-yl)hydrazin-1-ylidene]methyl]-N,N-dimethylaniline
3-(5-tert-butyl-1,2-oxazol-3-yl)-1-phenylurea
(4-chlorophenyl)methanimidamido 3-chlorothiophene-2-carboxylate
N-{4-[(E)-2-phenyldiazen-1-yl]phenyl}acetamide
methyl 4-[(pyrimidin-2-ylsulfanyl)methyl]benzoate
2-phenylimidazo[1,2-a]pyridine
6-chloro-2-phenyl-4H-thiochromen-4-one
2-{[(4-methylphenyl)methyl]sulfanyl}-5-(pyrazin-2-yl)-1,3,4-thiadiazole
5,7-dihydroxy-2-(4-hydroxyphenyl)-4H-chromen-4-one
(E)-[I-(1H-pyrrol-2-yl)ethylidene]amino N-(4-chlorophenyl)carbamate
1-benzoyl-3-2,3-dihydro-1H-inden-5-ylthiourea
1-{1-phenyl-1H-pyrazolo[3,4-d]pyrimidin-4-yl}-2,3-dihydro-1H-indole
N,5-diphenyl-1,3,4-oxadiazole-2-carboxamide
(3Z)-3-(2,3-dihydro-1-benzofuran-5-ylmethylidene)-2,3-dihydro-1H-indol-2-one
[(3-methylbutyl)sulfanyl]-N-phenylformamide
2,4-dihydroxy-5,7-diphenylpyrano[2,3-d]pyrimidin-8-ium perchlorate
ethyl 7-hydroxy-9-oxo-9H-xanthene-2-carboxylate
[({[3,5-Dimethyl-1-(2-methyl-2-propanyl)-1H-pyrazol-4-yl]methylene}amino)oxy]{[3-(trifluoromethyl)phenyl]amino}methanone
5-[(4-iodophenyl)amino]-3-phenyl-1,3-thiazolidine-2,4-dione
N-(furan-2-ylmethyl)-2-[methane(4-phenoxyphenyl)sulfonamido]acetamide
N-(3-methoxyphenyl)-6-phenylpyridazin-3-amine
ethyl (2E)-3-[(2-chlorophenyl)amino]-2-cyanoprop-2-enoate
1-[3-chloro-1-benzothiophen-2-yl)carbonyl]-1H,2H,3H,4H,6H,10bH-pyrimido[2,1-a]isoindol-6-one
2-(4-chlorophenyl)-5-[(cyclopropylmethyl)sulfanyl]-1,3,4-oxadiazole
1-[6-(benzyloxy)-3-tert-butyl-2-hydroxyphenyl]ethan-1-one
3-[(1 E)-1-[(2,2-dichloroethenyl)imino]-2,2-dimethylpropyl]-1-(4-methylphenyl)thiourea
6,7-dimethyl-2-phenylquinoxaline
5-(2,3-dihydro-1-benzofuran-5-yl)-3-(4-fluorophenyl)-1,2,4-oxadiazole
2-{4-[(4-methylphenyl)methoxy]phenyl} acetonitrile
1-cyclohexyl-3-8-oxatricyclo[7.4.0.0^{2,7}]trideca-1(9),2(7),3,5,10,12-hexaen-5-ylurea
5-(1,2,3-thiadiazol-4-yl)-3-[4-(trifluoromethyl)phenyl]-1,2,4-oxadiazole
N-(2-methylquinolin-6-yl)-2-phenylacetamide
3-(piperidin-1-ylcarbonyl)-5-(thiophen-2-yl)-1,2-oxazole
N-(3,4-dimethylphenyl)[(E)-N'-(thiophen-2-ylmethylidene)hydrazinecarbonyl]formamide
2-(2,3-dimethoxyphenyl)-2,3-dihydro-1,3-benzothiazole
2-methyl-5-(naphthalen-2-yl)-1,3-thiazole hydrobromide
(cyclohexylcarbamothioyl)-N-(4-fluorophenyl)formamide
4-(1,3-benzothiazol-2-yl)-1-methyl-1H-pyrazol-3-amine
(4-tert-butylphenyl)methanimidamido 5-methyl-1,2-oxazole-3-carboxylate
N-[2-(methylsulfanyl)-1,3-benzothiazol-6-yl]thiophene-2-carboxamide
N-(5-cyclopropyl-1,3,4-thiadiazol-2-yl)-2H-1,3-benzodioxole-5-carboxamide
(2E)-3-(2-chlorophenyl)-N-(2-methylbut-3-yn-2-yl)prop-2-enamide
1-naphthalen-1-yl-3-8-oxatricyclo[7.4.0.0^{2,7}]trideca-1(13),2,4,6,9,11-hexaen-5-ylthiourea
3-methyl-N-phenyl-1-benzothiophene-2-carbothioamide
5-(2,5-dichlorophenyl)-N-[2-(trifluoromethyl)phenyl]furan-2-carboxamide
3-(5-methyl-1,2-oxazol-3-yl)-5-(thiophen-2-yl)-1,2,4-oxadiazole
N-(1H-indazol-3-yl)-3-methoxybenzamide
2-(4-tert-butylphenyl)-5-[(propane-1-sulfonyl)methyl]-1,3,4-oxadiazole
1-[2-(4-chlorophenoxymethyl)-4-methyl-1,3-thiazol-5-yl]ethan-1-one
(4-methanesulfonamidophenyl)methanimidamido N-(4-methylphenyl)carbamate
N-phenyl-4,5,6,7-tetrahydro-1,3-benzothiazol-2-amine hydrochloride
7-nitro-N-(2-phenylethyl)-1H-indole-2-carboxamide
2-{[(2E)-4-(pyridin-2-ylsulfanyl)but-2-en-1-yl]sulfanyl}pyridine
4-[(E)-2-(3-methylthiophen-2-yl)ethenyl]-2-[(3-nitropyridin-2-yl)sulfanyl]pyrimidine
4-(4-chlorophenyl)-2-[(4-methoxyphenyl)methyl]-1,3-thiazole
(3Z)-3-{[5-(thiophen-2-yl)thiophen-2-yl]methylidene}-2,3-dihydro-1H-indol-2-one
N-(4-bromo-2,5-difluorophenyl)-2,3-dimethylbenzamide
sodium N-phenyl(phenylamino)carboximidate
2-(benzylsulfanyl)-N-(2,3-dihydro-1H-inden-2-yl)acetamide
(5Z)-5-[(5-methylfuran-2-yl)methylidene]-3-phenyl-1,3-thiazolidine-2,4-dione
N-{4-[(3-chlorophenyl)carbamoyl]phenyl}thiophene-2-carboxamide
N-[(3-chlorophenyl)methyl]-5-(methylsulfanyl)-1,3,4-thiadiazol-2-amine
(E)-2-(phenylamino)-3-(phenylimino)guanidine
(2Z)-3-methyl-2-[2-(3-methyl-2,3-dihydro-1,3-benzoxazol-2-ylidene)hydrazin-1-ylidene]-2,3-dihydro-1,3-benzoxazole
3-[2-(2H-1,4-benzothiazin-3-yl)hydrazin-1-yl]-2H-1,4-benzothiazine
3-(3,4-dimethyl-1,2-oxazol-5-yl)-1-[4-(dimethylamino)-3,5-difluorophenyl]carbonylurea

TABLE 1-continued

Small molecules EZH2 inhibitors
EZH2 Inhibitors (3Z)-3-[2-(2,5-difluorophenyl)hydrazin-1-ylidene]piperidin-2-one
N'-[(E)-[1-(1-benzofuran-2-yl)ethylidene]amino](methylsulfanyl)methanimidamide
(2Z)-3-(9H-fluoren-2-ylcarbamoyl)prop-2-enoic acid
4-[2-(2,3-dihydro-1,4-benzodioxin-6-yl)diazen-1-yl]-N,N-diethylaniline
4,5-dichloro-N-(3-chloro-4-fluorophenyl)-1,2-thiazole-3-carboxamide
5-[4-(4-methoxyphenoxy)phenyl]-1H-pyrazole
1-cyclohexyl-3-[(Z)-(1H-pyrazol-3-ylmethylidene)amino]thiourea
[5-(4-chlorophenyl)-3-methyl-2-sulfanylidene-1,3,4-thiadiazinan-6-ylidene]amino 5-tert-butylthiophene-2-carboxylate
N-(2-phenylethyl)benzenecarbothioamide
5-amino-3-methyl-2-N-phenylthiophene-2,4-dicarboxamide
3-amino-5-(thiophen-3-yl)thiophene-2-carboxamide
(2E)-2-{[4-(trifluoromethoxy)phenyl]imino}-3,4-dihydro-2H-1,3-benzoxazin-4-one
3-hydroxy-9H-xanthen-9-one
4-[(E)-2-(3,5-dihydroxyphenyl)ethenyl]benzene-1,2-diol
(3-chlorophenyl)methanimidamido 6-(2,2,2-trifluoroethoxy)pyridine-3-carboxylate
5-phenyl-3-(pyrrolidin-1-yl)-1,2-thiazole-4-carbonitrile
7-hydroxy-3-(4-hydroxyphenyl)-4H-chromen-4-one
2-(4-fluorophenyl)-2H,3H,5H,6H,7H,8H-[1,2,4]triazolo[4,3-a]pyrimidin-3-one
(4-chlorophenyl)methanimidamido 2,6-difluorobenzoate
2-(2-amino-3-methoxyphenyl)-4H-chromen-4-one
6,7-dimethoxy-2-phenylquinoxaline
6-methoxy-3-phenyl-[1,2,4]triazolo[4,3-a]pyridazine
5-[4-(furan-2-ylcarbonyl)piperazin-1-yl]-3-(thiophen-2-yl)-1,2,4-thiadiazole
(E)-{1-[2-(4-chlorophenoxymethyl)-1,3-thiazol-4-yl]ethylidene}amino benzoate
N-[(2-chloro-6-fluorophenyl)carbonyl]-N'-(4-methylpyridin-2-yl)ethanediamide
(E)-hydroxy[1-(2-phenyl-1,3-thiazol-4-yl)ethylidene]amine
ethyl 1-{[4-(trifluoromethoxy)phenyl]carbamoyl}piperidine-4-carboxylate
3-(3-methyl-1H-indol-1-yl)-N-[4-(morpholin-4-yl)phenyl]propanamide
6,8-dimethyl-1-methylidene-2-(4-methylphehyl)-1,4-dihydronaphthalene
N'-[(2-methyl-1,3-thiazol-4-yl)methoxy]-4-(trifluoromethyl)benzene-1-carboximidamide
1-[4-(benzyloxy)phenyl]-3-[(3-cyanopyridin-2-yl)amino]urea
2-phenylimidazo[1,2-a]pyridine
3-(morpholin-4-yl)-5-[4-(trifluoromethyl)phenyl]-1,2-thiazole-4-carbonitrile
N-(2-chlorophenyl)-2-[(3-cyano-6-acetylpyridin-2-yl)sulfanyl]acetamide
3-[4-(4-methoxyphenyl)-1,3-thiazol-2-yl]-5-methyl-1,2-oxazole
N-(3-bromo-5-methylpyridin-2-yl)-4-ethylbenzamide
2-(5-methyl-1,2-oxazol-3-yl)-5-[3-(trifluoromethyl)phenyl]-1,3,4-oxadiazole
(E)-[1-(3-methyl-1-benzothiophen-2-yl)ethylidene]amino N-phenylcarbamate
N-(2,3-dihydro-1H-inden-2-yl)-3-(3-methyl-1H-indol-1-yl)propanamide
1,3-dimethanesulfonyl-2,3-dihydro-1H-1,3-benzodiazole
methyl 2-[5-methyl-2-(thiophene-2-amido)-1,3-thiazol-4-yl]acetate
4-[(5-{[(4-chlorophenyl)sulfanyl]methyl}furan-2-yl)carbonyl]morpholine
2-oxo-2-phenylethyl 2,3-dimethoxybenzoate
N-(4-chlorophenyl)-4-hydroxy-2-oxo-1,2-dihydroquinoline-3-carboxamide
(2,4-dichlorophenyl)methyl N-[(2-fluorophenyl)carbonyl]carbamate
2-[(4-chlorophenyl)carbonyl]-1-benzofuran
4-chlorophenyl 2,3-dihydro-1-benzofuran-5-carboxylate
2-[4-(dimethylamino)phenyl]-1,2,3,4-tetrahydroquinolin-4-one
[6-(ethylsulfanyl)pyridin-3-yl]methanimidamido thiophene-2-carboxylate
N-[(6-methyl-2-oxo-4-propyl-1,2-dihydropyridin-3-yl)methyl]-6-[2-(4-methylpiperazin-1-yl)pyridin-4-yl]-1-(propan-2-yl)-1H-indazole-4-carboxamide (GSK343)
N-[(4,6-dimethyl-2-oxo-1,2-dihydro-3-pyridinyl)methyl]-3-methyl-1-((1S)-1-methylpropyl)-6-[6-(1-piperazinyl)-3-pyridinyl]-1H-indole-4-carboxamide (GSK126)
N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-indazole-4-carboxamide (GSK926)

In one specific non-limiting example, there is provided the pharmaceutical composition as described herein wherein said inhibitor is (−)-1-[(1R,4R,5S)-3-(Hydroxymethyl)-4,5-dihydroxy-2-cyclopenten-1-yl]4-aminoimidazo[4,5-c]pyridine hydrochloride (DZNep; 3-deazaneplanocin A).

In one example, the disclosure relates to a pharmaceutical composition as described herein, comprising at least one EZH2 inhibitor and at least one enhancer of IFN-γ receptor activity, wherein said inhibitor is an EZH2-binding protein. As used herein the term "protein", "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. Inventive proteins preferably contain only natural amino acids, although non-natural amino acids that is, compounds that do not occur in nature but that can be incorporated into a polypeptide chain and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. As used herein "dipeptide" refers to two covalently linked amino acids.

Thus, the term "EZH2-binding protein" as used herein refers to peptides, polypeptides or proteins having the ability to specifically bind to the EZH2 protein. For example, the EZH-binding protein may be an antibody or an antigen binding fragment. The term "antigen binding fragment(s)" used herein refers to fragments comprising portions of an intact antibody including some or all of the antigen binding regions and having the ability to bind specifically to the antigen of the intact antibody. For example, the antigen binding fragment may be a Fab fragment, a Fab' fragment, aF(ab')2 fragment, a Fv fragment, or a scFv fragment, but is not limited thereto. A Fab fragment contains the variable region and the constant region of a light chain and a variable region and the first constant domain (CH1) of a heavy chain. A Fab fragment possesses one antigen binding site. A Fab' fragment is different from a Fab fragment in that Fab' additionally has the hinge region with at least one cysteine residue at the C-terminal end of CH1. A F(ab')2 fragment comprises a pair of Fab fragments, which are generally covalently linked together by a disulfide bond between hinge cysteine residues near their carboxy termini. A Fv fragment is an antibody fragment which contains a complete antigen recognition and binding site, consisting of a dimer of one heavy and one light chain variable domain in tight association. Recombinant techniques for producing the Fv fragment are well-known in the art. A Fv fragment may have a structure in which the heavy chain and the light chain variable regions are linked by a non-covalent bond. Single-chain Fv (scFv) fragments generally may have a dimer structure in which the heavy chain and the light chain variable regions are covalently bound via a peptide linker whereas disulfide-linked (scFv)2 fragments may have a structure in which two scFv fragments are directly linked to each other at the C-termini through a disulfide bond. The antigen binding fragment may be obtained using a protease to digest an intact antibody, such as papain to obtain Fab fragments or pepsin to obtain F(ab')2 fragments. Alternatively, the antigen binding fragment may be prepared by a genetic recombinant technique.

In one non-limiting, the disclosure relates to a pharmaceutical composition as described herein, wherein said EZH2-binding protein is an antibody or fragment thereof. The term "antibody" used herein includes intact antibodies as well as antigen binding fragments of intact antibody molecules, i.e., fragments having antibody-like specific binding to an antigen, for example, the EZH2 protein.

The antibody may be a monoclonal antibody, a bispecific antibody, a non-human antibody, a humanized antibody, a human antibody, a chimeric antibody, a Fab fragment, a F(ab') fragment, a scFV fragment, a disulfide-bond Fv (sdFv) fragment, an anti-idiotype (anti-Id) antibody, and an epitope-binding fragment of these antibodies, but is not limited thereto.

The antibody may be a humanized antibody or a human antibody. A humanized form of a non-human antibody, such as a murine antibody, may be a chimeric antibody which contains minimal sequence derived from the non-human immunoglobulin, chains of the immunoglobulin, or fragments thereof, such as Fab, Fab', F(ab')2, and Fv.

A non-human antibody is humanized using a method known in the art. In general, a humanized antibody has at least one amino acid residue introduced from a non-human donor. The humanization of a non-human antibody may be performed by replacing residues from a CDR of a human antibody with CDR residues from the antibody of the non-human species, such as mouse, rat, rabbit, or non-human primate, having the desired specificity, affinity, and capacity. In some instances, framework region (FR) residues of the human immunoglobulin are replaced by corresponding non-human residues.

A human antibody possesses an amino acid sequence which corresponds to that of an antibody produced by a human and/or has been made using any of the techniques for making human antibodies. Human antibodies may be produced using various techniques known in the art, such as phage display, genetic recombinant techniques, and/or cell engineering.

Effector regions of human antibodies may interact with complement and effector cells of the human immune system. In addition, the human immune system does not recognize human antibodies as foreign materials, and thus, the immune reaction against human antibodies introduced into a human may be significantly less severe than that against non-human and chimeric antibodies introduced into a human. Moreover, human antibodies have a long half-life in the blood stream, and therefore, dosage and frequency of administration may be reduced.

The term "chimeric antibody" used herein refers to an antibody with sequences derived from two different species.

In another example, disclosed herein is a pharmaceutical composition as disclosed herein, wherein said inhibitor is a nucleic acid molecule or conjugate thereof. The EZH2-binding protein a EZH2 The role of inhibiting EZH2 in our study is to sensitize the advanced prostate cancer cells to IFN-γ induced cell death. This effect is achieved by restoring the expression of IFNGR1 by relieving the repression mediated by EZH2 through the usage of another EZH2 inhibitor, DZNep. The "nucleic acid molecule" or "polynucleotide" refers to polymers of nucleotides, and includes but is not limited to DNA, RNA, DNA/RNA hybrids including polynucleotide chains of regularly and/or irregularly alternating deoxyribosyl moieties and ribosyl moieties (i.e., wherein alternate nucleotide units have an —OH, then and then an —OH, then an —H, and so on at the 2' position of a sugar moiety), and modifications of these kinds of polynucleotides, wherein the attachment of various entities or moieties to the nucleotide units at any position are included. Thus as used herein, a "nucleic acid molecule EZH2 inhibitor" may be any nucleic acid or/and polynucleotide as defined herein comprising but not limited to a nucleotide, an oligonucleotide, a polynucleotide such as for example, a DNA single or double stranded, an RNA, an aptamer, a'microRNA (miRNA), a locked nucleic acid, a small interfering RNA (siRNA) or a peptide nucleic acid (PNA) that has the ability to inhibit the expression of the EZH2 gene, or EZH2 protein, or the catalytic or functional activity of EZH2 responsible for repressing the activity of molecules, such as for example, INFGR receptor. In other words, the nucleic acid has the ability to inhibit the repressive activity of EZH2 as defined herein.

Another modification of the oligonucleotides of the invention involves chemically linking to the oligonucleotide one or more moieties or "conjugates" which enhance the activity, cellular distribution or cellular uptake of the oligonucleotide. The compounds of the invention can include conjugate groups covalently bound to functional groups such as primary or secondary hydroxyl groups. Conjugate groups of the invention can include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenan-thridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Oligonucleotides composed of 2'-deoxyribonucleotides (oligodeoxyribonucleotides) are fragments of DNA and are often used in the polymerase chain reaction, a procedure that can greatly amplify almost any small amount of DNA. There, the oligonucleotide is referred to as a primer, allowing DNA polymerase to extend the oligonucleotide and replicate the complementary strand.

In one specific non-limiting example, the nucleic acid molecule as described herein is a small interfering RNA. As used herein, the term "siRNA" is meant to refer to a small inhibitory RNA duplex that induces gene silencing by operating within the RNA interference ("RNAi") pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

Each siRNA can include between 17 and 31 base pairs, more preferably between 18 and 26 base pairs, and most preferably 19 and 21 base pairs. Some, but not all, siRNA have unpaired overhanging nucleotides on the 5' and/or 3' end of the sense strand and/or the antisense strand. Additionally, the term "siRNA" includes duplexes of two separate strands, as well as single strands that can form hairpin structures comprising a duplex region, which may be referred to as short hairpin RNA ("shRNA").

As used herein, the terms "shRNA" or "hairpins" are meant to refer to unimolecular siRNA comprised by a sense region coupled to an antisense region through a linker region. A shRNA may have a loop as long as, for example, 4 to 30 or more nucleotides. In some embodiments it may be preferable not to include any non-nucleotides moieties. The shRNA may also comprise RNAs with stem-loop structures that contain mismatches and/or bulges, micro-RNAs, and short temporal RNAs. RNAs that comprise any of the above structures can include structures where the loops comprise nucleotides, non-nucleotides, or combinations of nucleotides and non-nucleotides. The sense strand and antisense strand of a shRNA are part of one longer molecule or, in the case of fractured hairpins, two (or more) molecules that form a fractured hairpin structure.

Figure 1:
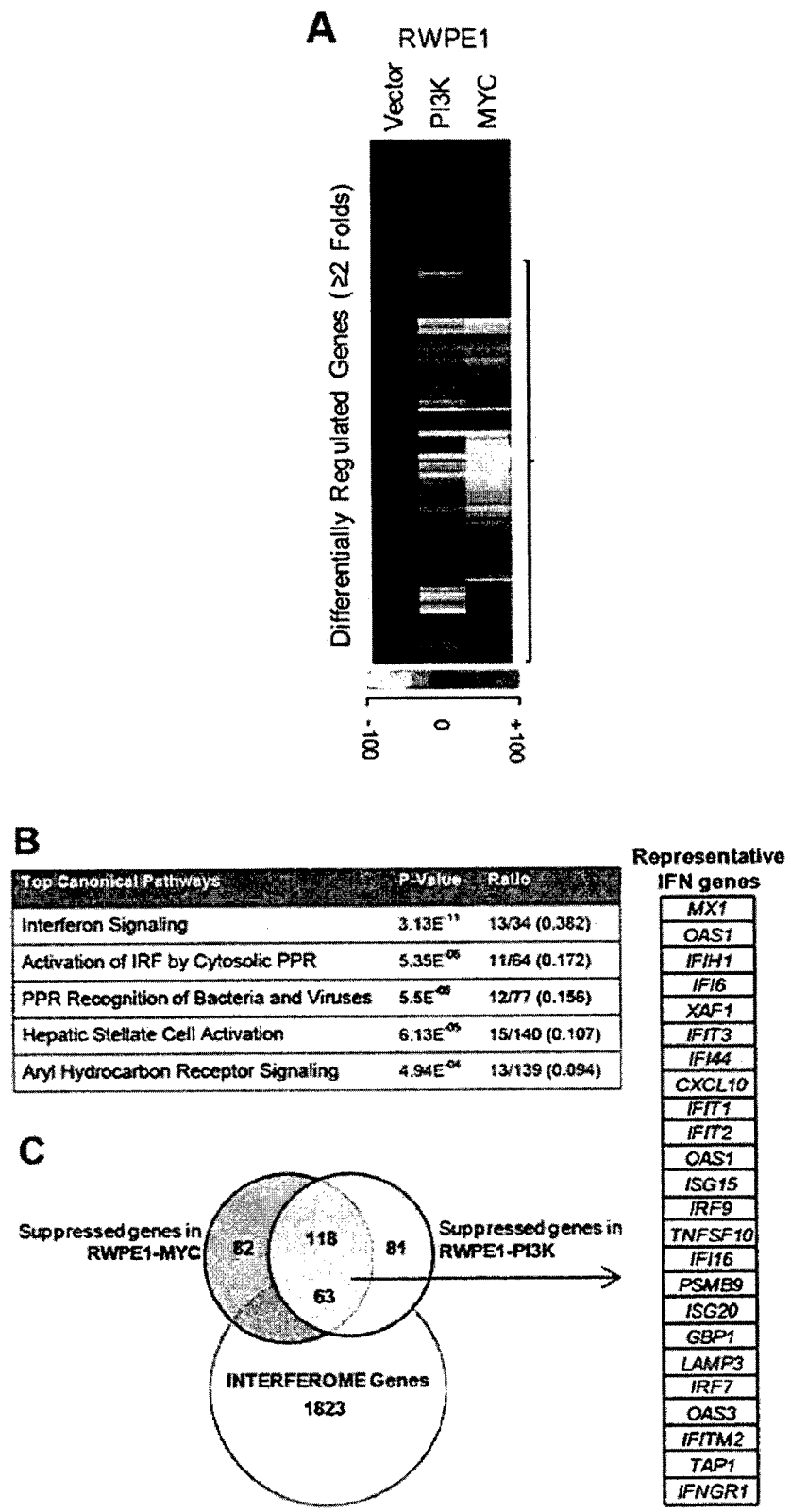
FIG. 1 is a series of drawings, graphs and western-blot analysis showing that oncogenic transformation by MYC and PI3K induced transcriptional inactivation of IFN-γ-JAK-STAT1 signaling pathway.
Figure 1:
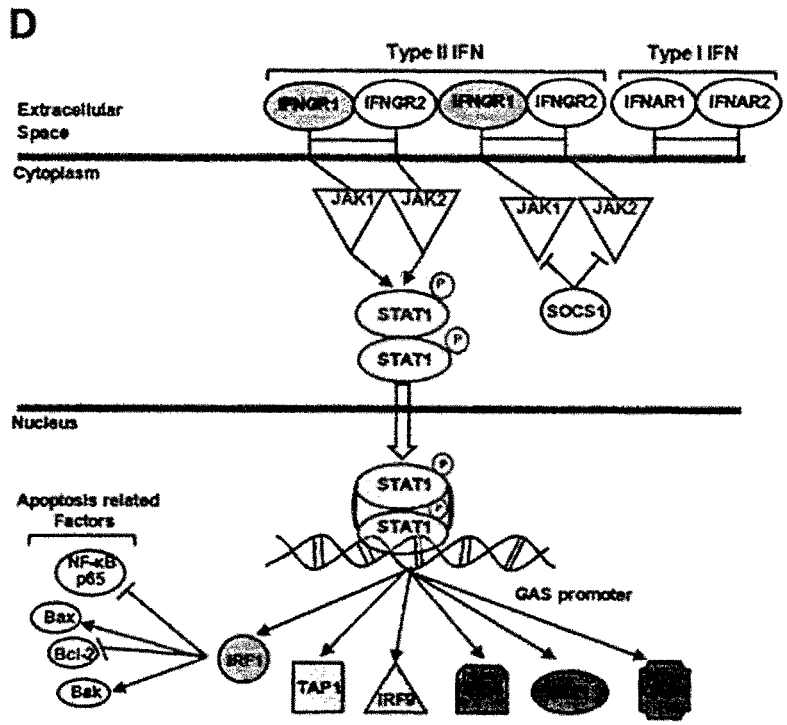
Figure 1:
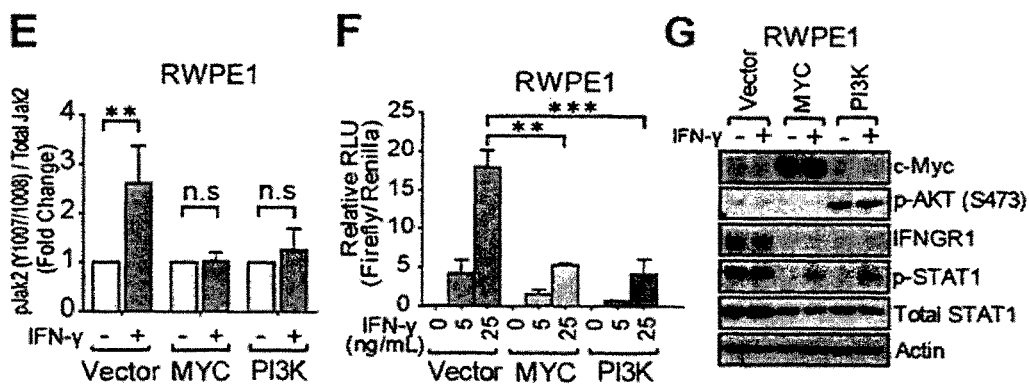
Figure 1:
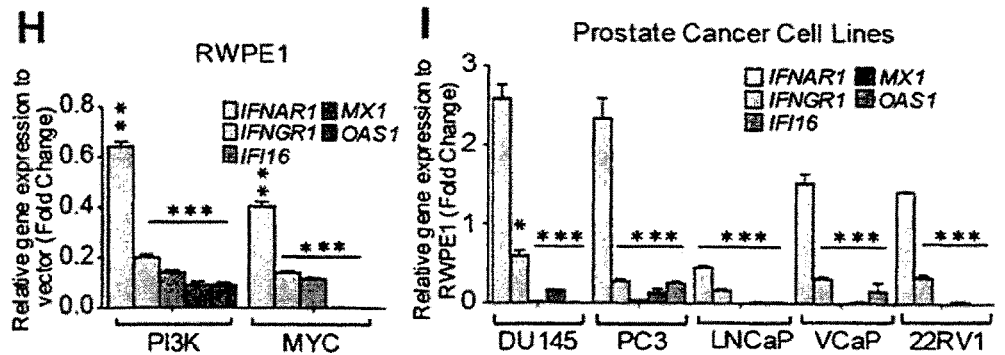
Figure 2:
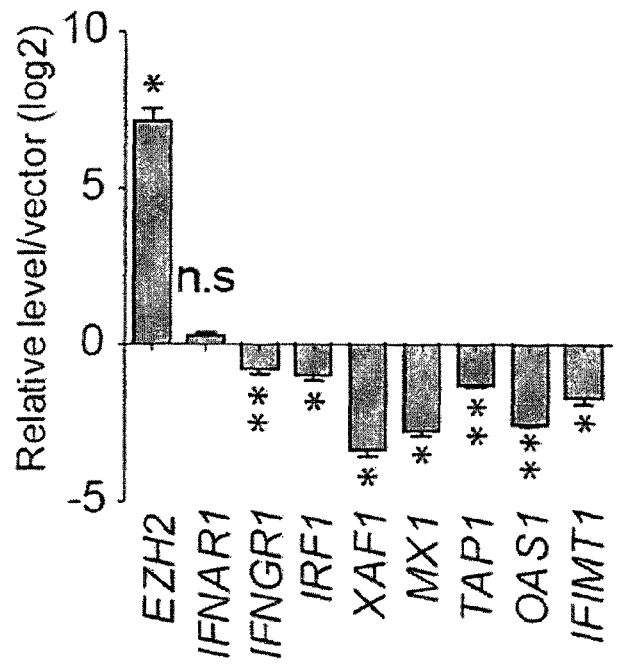
FIG. 2 is a series of graphs and analysis showing that IFNGR1 is a direct target of EZH2 in MYC-driven, but not PI3K-driven prostate cancer cells.
Figure 2:
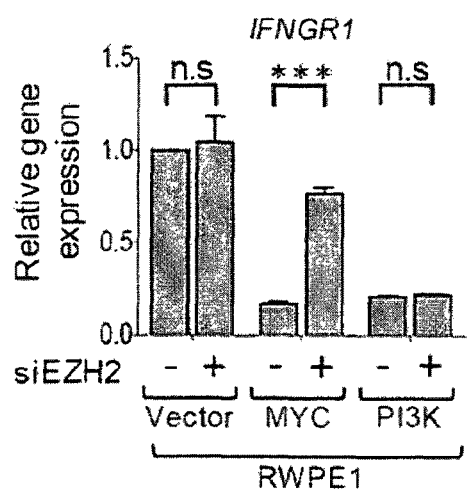
Figure 2:
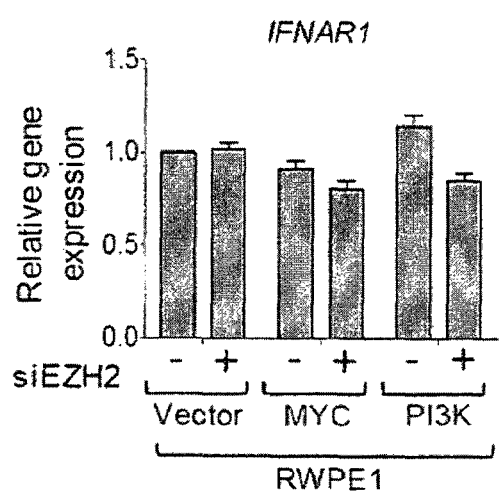
Figure 2:
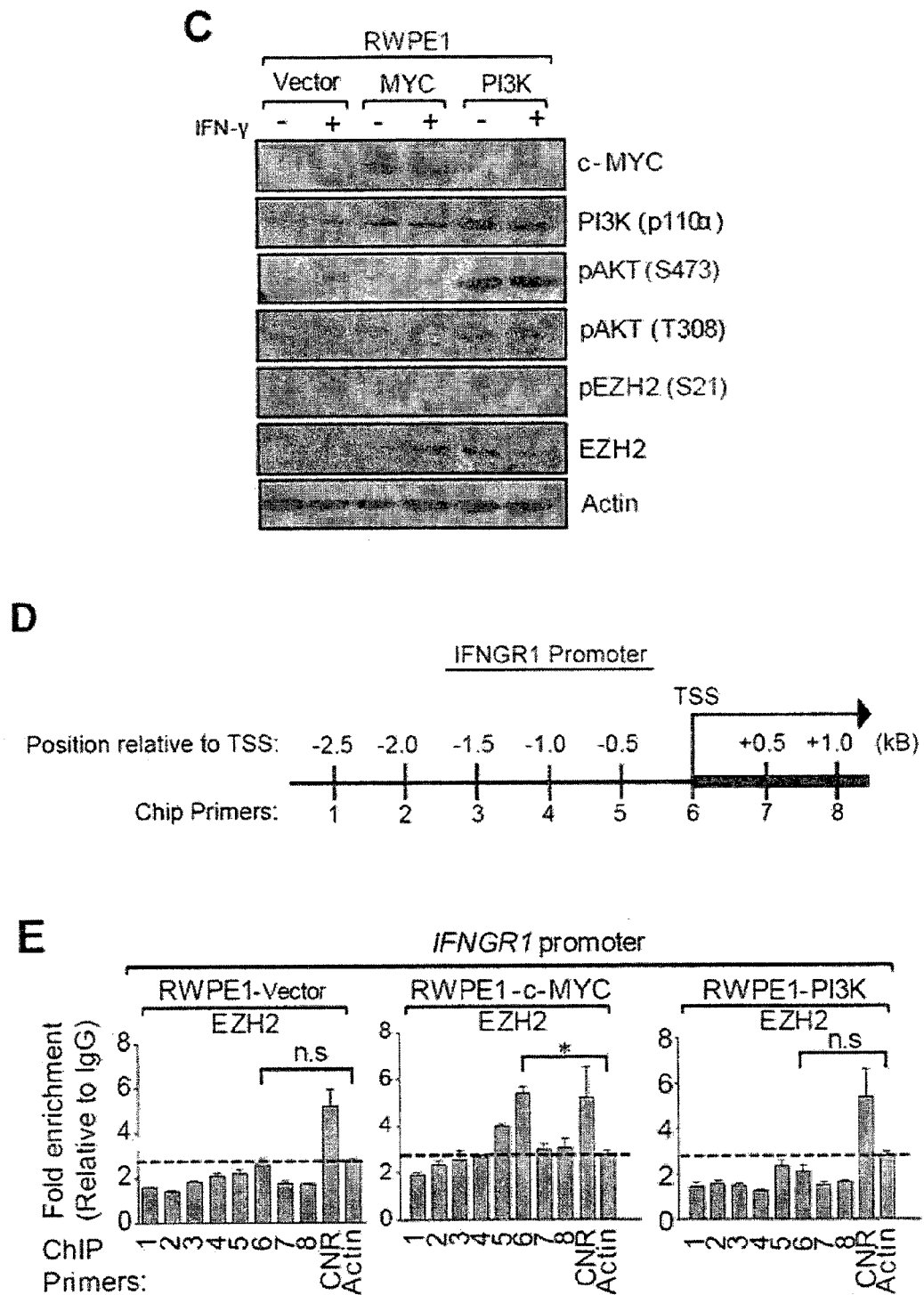
Figure 2:
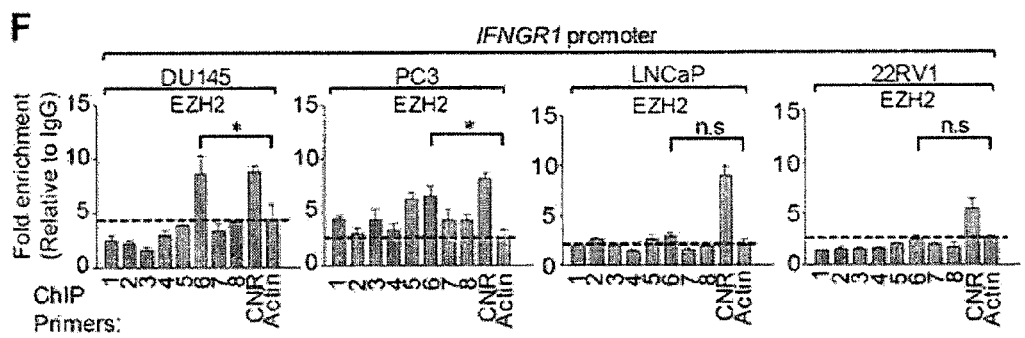
Figure 2:
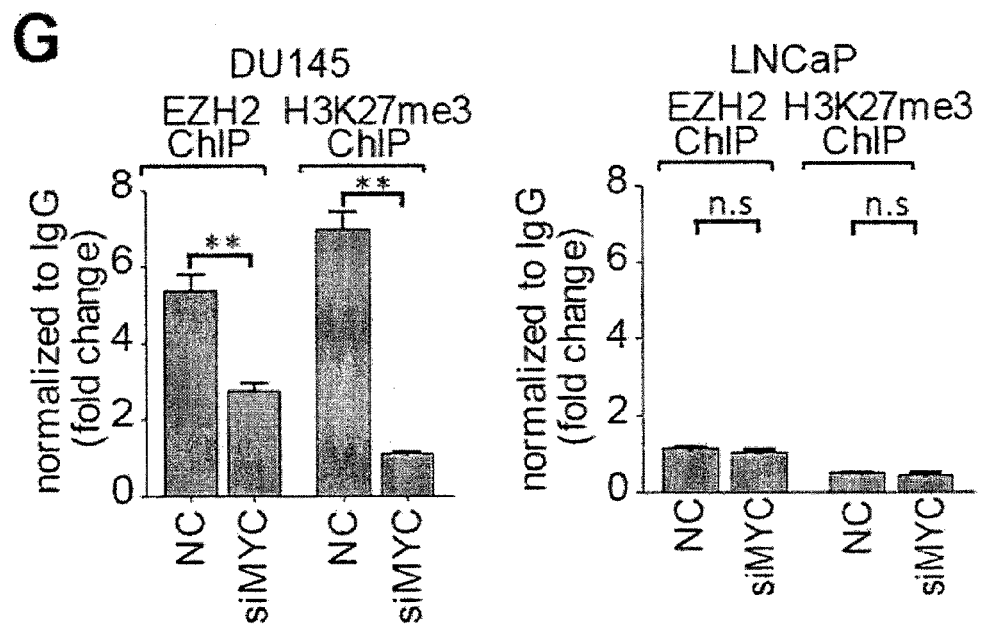

In one example, there is provided a pharmaceutical composition as described herein, wherein said enhancer is interferon-gamma (IFN-γ). It has been shown herein that EZH2 inhibitors sensitize cells to IFN-γ receptor enhancer, such as for example, IFN-γ. Accordingly, in response to derepression of the IFNGR1 gene, the IFNGR1 receptor is expressed at the surface of the target cells. Consequently, IFNGR1 ligands, such as for example, IFN-γ may bind to the receptor and activate the STAT1 tumour suppressor pathway. For example, FIG. 1 shows that the epigenetic repression of IFNGR1 is mediated by EZH2 and is reversible. The inventors demonstrated that, for example DZNep is a potent inhibitor of EZH2 that effectively relieve the repression of IFNGR1 and allows activation of the IFN-γ-STAT1 pathway in cancer cells, such as prostate cancer cells. In other words, DZNep sensitize the cells to IFN-γ. The specificity of DZNep towards EZH2 is further shown in FIG. 2. Thus, adding IFN-γ to EZH2 inhibitor treatment surprisingly enhances the beneficial therapeutic effect of EZH2 inhibitor.

In one example, disclosed herein is a pharmaceutical composition as described herein, wherein said inhibitor is DZNep and said enhancer is IFN-γ. In other non-limiting examples, the pharmaceutical composition may comprise IFN-γ and an inhibitor of EZH2, as described herein, including but not limited to a small molecule inhibitor, a EZH2-binding protein such as an EZH2 antibody and a nucleic acid such as at least one siRNA capable of silencing EZH2 expression.

The pharmaceutical compositions described herein, comprising at least one EZH2 inhibitor and at least one IFNGR enhancer can be useful for treating one or more diseases responsive to relief from EZH2 repression and the IFN-γ pathway activation. Without wishing to be bound to any particular theory, it is believed that the interaction of the compounds disclosed herein with EZH2 results in the inhibition of EZH2 activity and thus in the pharmaceutical utility of these compounds. Thus in one example, there is provided a pharmaceutical composition as described herein, for use in therapy. Accordingly, the disclosure includes a method of treating a mammal, for instance a human, having a disease responsive to inhibition of EZH2 activity and activation of IFNGR1, comprising administrating to the mammal having such a disease, an effective amount of at least one pharmaceutical composition provided herein. In one non-limiting specific example, there is provided a method of treating a patient having cancer comprising administration of the pharmaceutical composition as defined herein. In another example, the method as disclosed herein, comprises administration of the pharmaceutical composition comprising DZNep as a EZH2 inhibitor and IFN-γ as an enhancer of interferon gamma receptor activity to the patient in need thereof. An effective concentration may be ascertained experimentally, for example by assaying blood concentration of the compound, or theoretically, by calculating bioavailability.

The term "treatment" (and grammatical variants thereof) as used herein is intended to be construed broadly and includes a reference to any and all uses which remedy a disease state or symptoms, prevent the establishment of disease, or otherwise prevent, hinder, retard, or reverse the progression of disease or other undesirable symptoms in any way whatsoever. Accordingly, the term "treatment" can include any of the following (i) the prevention or inhibition of cancer, or recurrence thereof, (ii) the reduction or elimination of symptoms or cancer cells, (iii) the substantial or complete elimination of cancer, and (iv) the stabilization (i.e. not worsening) of cancer.

In one example, there is provided the use of a pharmaceutical composition as described herein, comprising for example at least one EZH2 inhibitor, such as DZNep, an antibody, or a siRNA, and at least one IFNGR enhancer such as IFN-γ, in the manufacture of a medicament for the treatment of a patient having cancer. In one embodiment, there is provided the use of the pharmaceutical composition as described herein, wherein cancer is a metastatic cancer.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In one example, there is provided the method as described herein, wherein said inhibitor is used in a daily dosage of between about 0.01 and about 1000 mg/kg body weight per day. In a further example, the amount of inhibitor is between about 0.1 and about 500 mg/kg body weight, more preferred 0.1 and about 100 mg/kg body weight and most preferred 1.0 and about 10 mg/kg body weight per day. In another example, there is provided the method as described herein, wherein said inhibitor is used in amount of less than 3 mg/kg, or less than 2 mg/kg, or less than 1 mg/kg, or less than 0.8 mg/kg, or less than 0.5 mg/kg, or less than 0.2 mg/kg, or between about 0.1 mg/kg to about 3 mg/kg.

In one example, there is provided the method as described herein, wherein said enhancer is used in an amount of less than $5 \times 10^8$ IU/kg, or less than $10^8$ IU/kg, or less than $5 \times 10^7$ IU/kg, or less than $2 \times 10^7$ IU/kg, or less than $10^7$ IU/kg, or less than $5 \times 10^6$ IU/kg, or less than $2 \times 10^6$ IU/kg, or less than $10^6$ IU/kg, or less than $5 \times 10^5$ IU/kg, or less than $2 \times 10^5$ IU/kg or in an amount of between about $1 \times 10^5$ IU/kg to about $10^8$ IU/kg of body weight per day. In a further example, there is provided the method as described herein, wherein said enhancer is used in an amount of less than $5 \times 10^6$ IU/kg, or less than $10^6$ IU/kg, or less than $5 \times 10^5$ IU/kg, or less than $2 \times 10^5$ IU/kg, or in an amount of between about $1 \times 10^5$ IU/kg to about $10^6$ IU/kg.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and *acacia* or tragacanth; pastilles comprising the active ingredient in an inert base such as gelatin and glycerin or sucrose and *acacia*; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for, example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The pharmaceutical composition of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

Formulations

Pharmaceutical preparations for delivery by various routes are formulated as shown in the following tables. "Active ingredient" or "active compound" as used in the tables means at least one EZH2 inhibitors and at least one INF-gamma receptor enhancer of the pharmaceutical composition.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | % wt./wt. |
|---|---|
| Active ingredient | 1.0 g |
| Magnesium stearate | 0.5% |
| Crosscarmellose sodium | 2.0% |
| Lactose | 76.5% |
| PVP (polyvinylpyrrolidine) | 1.0% |

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The at least two components of the pharmaceutical composition disclosed (i.e. the at least one EZH2 inhibitor and the at least one IFN-gamma receptor enhancer) may be co-administered at the same time (e.g. simultaneously) or at different times (e.g. sequentially) and over different periods of time, which may be separate from one another or overlapping. Where the two components are co-administered simultaneously they may be provided in one or more pharmaceutical compositions. Where the two components are provided in the form of separate compositions the two components may be co-administered separately, sequentially or simultaneously. The two components may be administered in any order but in one example the at least one EZH2 inhibitor is administered prior to the at least one IFN-gamma receptor enhancer.

In one example, the at least two components of the pharmaceutical compositions may be administered by the same or different routes. For example, the composition is administered locally. In another example as shown in example 6 described below, IFN-γ is administered via intraperitoneal (I.P) route once daily and DZNep via subcutaneous injection once every 2 days. The present disclosure also envisages administering the compounds systemically. In some instances, the compounds are administered orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, orally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof. For example, in some variations, the compounds are administered intravenously, intra-arterially or orally. For example, in some variations, the compounds are administered intravenously.

Where the two components are administered as separate compositions, they may be administered within 120, 96, 84, 72, 48, 36, 24, 12, 6, 3, 2, 1, 0.5, 0.25 or 0.125 hours of each other. For example, EZH2 inhibitor is administered within 84, 72, 48, 36, 24, 12, 6, 3, 2, 1, 0.5, 0.25 or 0.125 hours prior to administration of the IFN-γ receptor enhancer. It may be useful to administer IFN-γ receptor enhancer prior the EZH2 inhibitor to assess the effect of the enhancer on the expression of factors involved, for example in apoptosis, cell cycle arrest, proliferation or any molecular mechanism useful in the treatment of aggressive cancer and thus adapt the amount of drug needed and the EZH2 inhibitor to be used in a given patient. For example, it may be advantageous to administer IFN-γ intraperitoneally and to administer DZNep by subcutaneous injection rather than by intraperitoneal administration to reduce potential adverse effects such as weight loss.

In one example, there is provided the method as described herein, wherein cancer is metastatic cancer. Since as explained above, metastatic cancers such as for example metastatic prostate cancers, are often refractory to hormonal and surgical treatments, it may be advantageous to treat metastatic cancer with the pharmaceutical composition of the invention. In one example, the method as described herein can be used for treating prostate cancer, such as for example, metastatic prostate cancer. In another example, there is provided the methods as described herein, wherein cancer includes but is not limited to liver, ovarian, lung, acute lymphoblastic leukemia, breast particularly luminal B breast, bladder, and lymphoma mantle-cell cancer. In some embodiments, the cancer treated or prevented in the invention may be any form of a cancer. Any forms of tumor or cancer may be used in the invention including for example, a benign tumor and a metastatic malignant tumor. Examples of cancers include, but are not limited to, gastric cancer, colon cancer, lung cancer, breast cancer, bladder cancer, neuroblastoma, melanoma, head and neck cancer, esophagus cancer, cervix cancer, prostate cancer and leukemia.

Other examples of tumors include, but are not limited to, haematological malignancies and solid tumours. Solid tumours include for instance a sarcoma, arising from connective or supporting tissues, a carcinoma, arising from the body's glandular cells and epithelial cells or a lymphoma, a cancer of lymphatic tissue, such as the lymph nodes, spleen, and thymus.

Other cancers that can be envisaged to be treated by the method of the invention are solid tumours. As indicated above, the present disclosure is partially based on the unexpected discovery that in some cancer cell lines, tissue isolated from patient with cancer or, a tumor sample isolated from a patient having cancer the levels of EZH2 is increased and the level of INFGR1 is decreased. One skilled in the art would be able to determine the level of the mRNA, cDNA or proteins (e.g. EZH2 or INFGR) by techniques such as for example, RT-PCR, microarrays, ChIPs, immunofluorescence or western blot.

Thus, in one example, there is provided the method as described herein wherein the patient is characterized by an increased level of EZH2 in a tumor sample and a decreased level of IFNGR1 in a tumor sample. As presently shown by the inventors, a tumor cell, a tumour sample tissue or a whole organism having cancer wherein the level of EZH2 is increased and IFNGR1 is decreased as compared to a normal (or non-tumour) cell, normal (or non-tumour) tissue or healthy (non-cancerous) organism.

As used herein, the expression "gene upregulated in cancer" or a gene with "increased level" refers to a gene that is expressed (e.g., mRNA or protein expression) at a higher level in cancer (e.g., prostate cancer) relative to the level in other tissues. In some embodiments, genes upregulated in cancer are expressed at a level at least 10%, preferably at least 25%, even more preferably at least 50%, still more preferably at least 100%, yet more preferably at least 200%, and most preferably at least 300% higher than the level of expression in other tissues.

As used herein, the term "gene downregulated in cancer" or a gene with "decreased level" refers to a gene that is expressed (e.g., mRNA or protein expression) at a lower level in cancer tissue relative to the level in other tissue. In some embodiments, genes downregulated in cancer tissue are expressed at a level at least 10%, preferably at least 25%, even more preferably at least 50%, still more preferably at least 100%, yet more preferably at least 200%; and most preferably at least 300% lower than the level of expression in other tissues.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject. A "therapeutic" compound as defined herein is a compound (or an agent or a molecule or a composition) capable of acting prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state. In one example, the therapeutic compound includes but is not limited to an apoptosis promoting compound, a chemotherapeutic compound or a compound capable of alleviating or eliminating cancer in a patient.

The term "treat" or "treating" as used herein is intended to refer to providing an pharmaceutically effective amount of a peptide of the present invention or a respective pharmaceutical composition or medicament thereof, sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

Based on the above, there is provided a method for determining susceptibility of a patient suffering from cancer to a treatment with a pharmaceutical composition as defined herein, wherein the method comprises comparing a first level of EZH2, including but not limited to, EZH2 mRNA level in a tumor sample, EZH2 cDNA level made from mRNA from said tumor sample, and EZH2 protein level from said tumor sample, with a second level of EZH2 including but not limited to, EZH2 mRNA level from a non-tumor sample from said patient, EZH2 cDNA level made from mRNA from said non-tumor sample, and EZH2 protein level from said non-tumor sample; comparing a first level of IFNGR1 including but not limited to, IFNGR1 mRNA level from said tumor sample, IFNGR1 cDNA level made from mRNA from said tumor sample, and IFNGR1 protein level from said tumor sample with the level of IFNGR1, including but not limited to, IFNGR1 mRNA level from a non-tumor sample from said patient, IFNGR1 cDNA level made from mRNA from said non-tumor sample, and IFNGR1 protein level from said non-tumor sample; and wherein a patient characterized by an increased level of EZH2 in said tumor sample and a decreased level of IFNGR1 in said tumor sample is susceptible to a treatment with said pharmaceutical composition. Advantageously, the experimental results presented herein allowed the identification of for example, EZH2 and INFGR1, as potential therapeutic targets for the pharmaceutical composition as described herein. The term "susceptibility" in the context of the present invention refers to a patient's ability to be responsive to anti-cancer treatment, and relates to the presence or absence of EZH2 and INFGR1.

Hence, in one example, there is provided a method for treating cancer in a patient with a difference in the level of EZH2 mRNA, and/or EZH2 cDNA, and/or EZH2 protein and IFNGR1 mRNA, and/or IFNGR1 cDNA, and/or IFNGR1 protein in a tumor sample, and the level of EZH2 mRNA, and/or EZH2 cDNA, and/or EZH2 protein and IFNGR1 mRNA, and/or IFNGR1 cDNA, and/or IFNGR1 protein from a non-tumor sample, wherein the level of EZH2 mRNA, and/or EZH2 cDNA, and/or EZH2 protein are at least 2-fold higher in the tumor sample and the IFNGR1 mRNA, and/or IFNGR1 cDNA, and/or IFNGR1 protein level is at least 2-fold lower in the tumor sample, wherein the method comprises administration of a pharmaceutical composition as described herein to the patient. As explained above, there is an inverted correlation between the levels of EZH2 and IFNGR1 in patients having cancer or suspected to have cancer, making them more susceptible to treatment with the pharmaceutical compositions as described herein. The difference between the normalized levels of mRNAs, cDNAs or proteins between the tumour and non-tumour sample, is ideally no less than about 1.2-fold difference (higher or lower as indicated above, no less than about 1.2-fold no less than about 1.4-fold difference, no less than about 1.5-fold difference, no less than about 1.7-fold difference, no less than about 1.9-fold difference, no less than about 2-fold difference, no less than about 3-fold difference, no less than about 5-fold difference or no less than about 10-fold difference. In another example, there is provided the use of a pharmaceutical composition as described herein in the manufacture of a medicament for treating cancer in a patient with a difference in the level of EZH2 mRNA, and/or EZH2 cDNA, and/or EZH2 protein and IFNGR1 mRNA, and/or IFNGR1 cDNA, and/or IFNGR1 protein in a tumor sample, and the level of EZH2 mRNA, and/or EZH2 cDNA, and/or EZH2 protein and IFNGR1 mRNA, and/or IFNGR1 cDNA, and/or IFNGR1 protein from a non-tumor sample, wherein the level of EZH2 mRNA, and/or EZH2 cDNA, and/or EZH2 protein are at least 2-fold higher in the tumor sample and the IFNGR1 mRNA, and/or IFNGR1 cDNA, and/or IFNGR1 protein level is at least 2-fold lower in the tumor sample.

In one example, there is provided a method for treating cancer in a patient with a difference in the level of EZH2 mRNA, and/or EZH2 cDNA, and/or EZH2 protein and IFNGR1 mRNA, and/or IFNGR1 cDNA, and/or IFNGR1 protein in a tumor sample, and the level of EZH2 mRNA, and/or EZH2 cDNA, and/or EZH2 protein and IFNGR1 mRNA, and/or IFNGR1 cDNA, and/or IFNGR1 protein from a non-tumor sample, wherein the level of EZH2 mRNA, and/or EZH2 cDNA, and/or EZH2 protein are at least 2-fold higher in the tumor sample and the IFNGR1 mRNA, and/or IFNGR1 cDNA, and/or IFNGR1 protein level is at least 2-fold lower in the tumor sample, wherein the method comprises administration of a pharmaceutical composition as described herein, to the patient. In another example, there is provided the use of a pharmaceutical composition as described herein in the manufacture of a medicament for treating cancer in a patient with a difference in the level of EZH2 mRNA, and/or EZH2 cDNA, and/or EZH2 protein and IFNGR1 mRNA, and/or IFNGR1 cDNA, and/or IFNGR1 protein in a tumor sample, and the level of EZH2 mRNA, and/or EZH2 cDNA, and/or EZH2 protein and IFNGR1 mRNA, and/or IFNGR1 cDNA, and/or IFNGR1 protein from a non-tumor sample, wherein the level of EZH2 mRNA, and/or EZH2 cDNA, and/or EZH2 protein are at least 2-fold higher in the tumor sample and the IFNGR1 mRNA, and/or IFNGR1 cDNA, and/or IFNGR1 protein level is at least 2-fold lower in the tumor sample.

In another example, there is provided the method (or the medicament, or the pharmaceutical composition) as described herein, wherein the cancer comprises but is not limited to, prostate, liver, ovarian, lung, acute lymphoblastic leukemia, breast particularly luminal B breast, bladder, and lymphoma mantle-cell cancer. Based on the experimental results described herein, it may be possible to determine that patients having a tumor or suspected to have cancer, with a normalized high level of EZH2 and a normalized low level of INFGR1 as compared to the levels of EZH2 and INFGR1 in a corresponding tissue of a healthy subject, will respond efficiently to treatment with a pharmaceutical composition as described herein.

In one example, there is provided the method as described herein, wherein the first level of EZH2 protein from said tumor sample and the second level of EZH2 protein from said non-tumor sample, and wherein a first level of IFNGR1 protein from said tumor sample with the level of IFNGR1 protein from said non-tumor sample is examined by immunohistochemistry. The method includes the use of antibodies or fragments thereof directed against an antigen comprised in the EZH2 and the IFNGR1 proteins, and the use of secondary antibodies that have been modified with detectable moieties, such as for example, fluorescent, luminescent, chemiluminescent or radioactive moieties. The examination by immunochemistry should allow the skilled person in the art to quantify and normalize the amount of protein in the tumor sample and the non-tumor sample, in order to be able to compare the levels of proteins.

In another example, there is provided the method as described herein, wherein the level of EZH2 expression from said tumor sample and from said non-tumor sample, and wherein the level of IFNGR1 expression from said tumor sample and from said non-tumor sample is examined by q-PCR, wherein q-PCR comprises selecting primers comprising but not limited to primers having the nucleic acid sequences of SEQ ID No's 3 to 34. The person in the skilled art may select some primers to perform a quantitative polymerase chain reaction in order to be able to compare the expression levels of genes of interest in a tumour and a non-tumour sample.

In a further example, the present disclosure provides a method for determining susceptibility of a patient suffering from advanced prostate cancer to a treatment with a pharmaceutical composition as defined herein, wherein the method comprises comparing a first level of IFNGR1, including but not limited to, IFNGR1 mRNA level in a tumor sample, IFNGR1 cDNA level made from mRNA from said tumor sample, and IFNGR1 protein level from said tumor sample with the level of IFNGR1, including but not limited to, IFNGR1 mRNA level from a non-tumor sample from said patient, IFNGR1 cDNA level made from mRNA from said non-tumor sample, and IFNGR1 protein level from said non-tumor sample; and wherein a patient characterized by a decreased level of IFNGR1 in said tumor sample is susceptible to a treatment with said pharmaceutical composition.

In one example, there is provided a method for determining susceptibility of a patient suffering from breast cancer to a treatment with a pharmaceutical composition as defined herein, wherein the method comprises comparing a first level of IFNGR1, including but not limited to, IFNGR1 mRNA level in a tumor sample, IFNGR1 cDNA level made from mRNA from said tumor sample, and IFNGR1 protein level from said tumor sample with the level of IFNGR1, including but not limited to, IFNGR1 mRNA level from a non-tumor sample from said patient, IFNGR1 cDNA level made from mRNA from said non-tumor sample, and IFNGR1 protein level from said non-tumor sample; wherein a patient suffering from basal breast cancer is characterized by an increased level of INFGR1 in said tumor sample is not susceptible to a treatment with said pharmaceutical composition; and wherein a patient suffering from luminal breast cancer is characterized by a decreased level of INFGR1 in said tumor sample is susceptible to a treatment with said pharmaceutical composition.

In one example, there is provided a method for making a prognosis with respect to the clinical outcome of a patient suffering from cancer comprising comparing a first level of EZH2, including but not limited to, EZH2 mRNA level in a tumor sample, EZH2 cDNA level made from mRNA from said tumor sample, and EZH2 protein level from said tumor sample, with a second level of EZH2, including but not limited to, EZH2 mRNA level from a non-tumor sample from said patient, EZH2 cDNA level made from mRNA from said non-tumor sample, and EZH2 protein level from said non-tumor sample; comparing a first level of IFNGR1, including but not limited to, IFNGR1 mRNA level from said tumor sample, IFNGR1 cDNA level made from mRNA from said tumor sample, and IFNGR1 protein level from said tumor sample with the level of IFNGR1, including but not limited to, IFNGR1 mRNA level from a non-tumor sample from said patient, IFNGR1 cDNA level made from mRNA from said non-tumor sample, and IFNGR1 protein level from said non-tumor sample; and making a prognosis with respect to the clinical outcome of a patient suffering from cancer. In a further example, there is provided the method as defined above, wherein said clinical outcome indicates the susceptibility to treatment with said pharmaceutical composition as defined herein. In another example, there is provided the method as defined herein, wherein the cancer, can include but is not limited to, prostate, liver, ovarian, lung, particularly small cell lung, leukemia, particularly acute lymphoblastic leukemia, breast particularly luminal B breast, bladder, or lymphoma mantle-cell cancer.

EXPERIMENTAL SECTION

Example 1

MYC or PI3K-Mediated Oncogenic Transformation in Prostate Epithelial Cells Induces Transcriptional Inactivation of IFN-γ-JAK-STAT1 Signaling Gene amplification of MYC or constitutive activation of PI3K signaling pathway occurs frequently in advanced prostate cancer. To investigate the molecular events induced by MYC or PI3K, immortalized prostate epithelial RWPE cells were used and infected them with retroviral MYC or a constitutively activating mutant of PIK3CA (E545K), resulting in transformed cell lines showing elevated level of MYC or AKT phosphorylation, designated as RWPE1-MYC, and RWPE1-PI3K, respectively (FIG. 8 and FIG. 2C).

As oncogenic transformation is often coupled with epigenetic gene silencing, gene expressing profiling was performed and the focus was on pathways and gene sets that are downregulated upon oncogenic transformation. Among 610 genes differentially expressed (with 2-fold cutoff, P<0.01), a set of 344 genes were identified that was downregulated in both RWPE1-MYC and RWPE1-PI3K cells as compared with the empty vector control RWPE1 cells (FIG. 1A, Table 2). Ingenuity Pathway Analysis (IPA) indicates that this gene set was enriched for canonical interferon signaling as the top gene network (P<3×10$^{-11}$) (FIG. 1B).

Furthermore, 63 out of 344 genes commonly downregulated in MYC- and PI3K-activated cell lines were identified as interferon responsive genes (IFN genes) in the INTERFEROME database (FIG. 1C), which can be mapped at multiple levels in the IFN-JAK-STAT1 signaling cascade (FIG. 1D, highlighted in green). Notably, IFNGR1, which encodes the interferon γ receptor 1, was downregulated, while IFNAR1, which encodes the interferon α1 receptor, was not (FIG. 1D). Thus, these findings suggest that MYC or PI3K activation in prostate epithelial cells may have induced a transcriptional inactivation of IFN-signaling, which is specific for IFNGR1, but not IFNAR1.

Downregulation of interferon γ receptor (IFNGR1) expression is expected to cause reduced response to IFN-γ stimulation, leading to impaired activation of JAK-STAT1 activity. Indeed, IFN-γ-induced phosphorylation of JAK2 and STAT1 transcriptional activity, as measured by an ELISA-based assay and a STAT1-mediated luciferase reporter assay respectively, were much reduced in both RWPE1-MYC and RWPE1-PI3K cells as compared to the control RWPE1 cells (FIGS. 1E and F).

Consistently, western blotting confirms the downregulation of IFNGR1 protein expression and dampened induction of STAT1 Tyr701 phosphorylation in response to IFN-γ treatment in RWPE1-MYC and RWPE1-PI3K cells as compared with the RWPE1 cells (FIG. 1G). Quantitative RT-PCR (qRT-PCR) analysis further validated the gene expression array data by showing the down regulation of IFNGR1 and various IFN downstream genes in both MYC- and PI3K-transformed RWPE1 cells (FIG. 1H). Importantly, the downregulation of IFNGR1 (but not IFNAR1) and the downstream IFN responsive genes were also found in a panel of prostate cancer cell lines (FIG. 1I).

TABLE 2

Downregulated genes expressed in terms of fold difference in either RWPE1-MYC or RWPE1-PI3K cells with a cut-off of <−2 after normalizing against the vector control RWPE1 cells.

| Symbol | RWPE1 Vector | PI3K (E545K) | MYC |
|---|---|---|---|
| IFI27 | 1 | −17.8743 | −73.0761 |
| IFI6 | 1 | −16.5152 | −40.9701 |
| IFI44L | 1 | −16.4912 | 0 |
| KLK5 | 1 | −15.3243 | 0 |
| RSAD2 | 1 | −14.7267 | 0 |
| XAF1 | 1 | −13.6573 | 0 |
| KLK5 | 1 | −13.4396 | −28.0406 |
| MX2 | 1 | −10.6677 | 0 |
| OAS2 | 1 | −9.71016 | 0 |
| OAS1 | 1 | −9.6326 | 0 |
| CLDN1 | 1 | −9.53868 | −12.4893 |
| EPSTI1 | 1 | −8.94257 | −24.3219 |
| RARRES3 | 1 | −8.77149 | 0 |
| S100P | 1 | −7.93449 | −1.09225 |
| XAF1 | 1 | −7.60302 | −11.5538 |
| TRIM22 | 1 | −7.42753 | −16.0546 |
| LAMP3 | 1 | −7.11102 | −5.8311 |
| HERC6 | 1 | −7.07562 | −20.6502 |
| SNRPN | 1 | −6.85279 | −1.59023 |
| MX1 | 1 | −6.83834 | −98.8357 |
| TNFSF10 | 1 | −6.24743 | −12.7431 |
| CCL2 | 1 | −6.14527 | 0 |
| CRIP1 | 1 | −6.0692 | −4.90306 |
| IFIT3 | 1 | −6.01677 | −39.1901 |
| SAMD9 | 1 | −5.89703 | −13.0126 |
| ISG15 | 1 | −5.73126 | −16.4992 |
| STAT1 | 1 | −5.59124 | −18.4787 |
| RPS4Y1 | 1 | −5.56669 | 1.485994 |
| OAS2 | 1 | −5.49693 | 0 |
| DDX60 | 1 | −5.44447 | −16.8777 |
| BTBD11 | 1 | −5.42183 | −3.77361 |
| ECGF1 | 1 | −5.38314 | −6.2397 |
| IFIT1 | 1 | −5.31675 | −31.9666 |
| IFIT3 | 1 | −5.30808 | 0 |
| CXCL10 | 1 | −5.25124 | −7.99236 |
| ZIC2 | 1 | −5.23106 | −4.08437 |
| IFITM1 | 1 | −5.13859 | −10.2944 |
| FOXQ1 | 1 | −5.10141 | −9.38273 |
| PNLIPRP3 | 1 | −5.0611 | 0 |
| SERPINA3 | 1 | −5.02867 | −5.9415 |
| SAMD9L | 1 | −4.99383 | 0 |
| AKR1B10 | 1 | −4.96005 | 0 |
| MXRA5 | 1 | −4.93851 | −5.07588 |
| OAS1 | 1 | −4.92301 | −6.837 |
| MKX | 1 | −4.88046 | −4.90035 |
| OAS2 | 1 | −4.86569 | 0 |
| OASL | 1 | −4.79873 | −18.0583 |
| ALDH3A1 | 1 | −4.7885 | −4.68453 |
| KRT15 | 1 | −4.74698 | −13.4386 |
| DDX58 | 1 | −4.62593 | −8.44421 |
| IFIT2 | 1 | −4.53772 | −23.129 |
| IFI44 | 1 | −4.5224 | −33.3923 |
| OAS1 | 1 | −4.45264 | −6.51132 |
| CTGF | 1 | −4.44726 | −16.4104 |
| STAT1 | 1 | −4.44203 | −14.4979 |
| SNRPN | 1 | −4.44051 | −1.1559 |
| UGT1A6 | 1 | −4.37973 | −5.34731 |
| IRF7 | 1 | −4.36642 | −7.12519 |
| DHRS3 | 1 | −4.34558 | −2.30335 |
| KLK10 | 1 | −4.32362 | −5.64646 |
| FAM43A | 1 | −4.29989 | −2.4056 |
| SDPR | 1 | −4.28703 | −3.76978 |
| SGK | 1 | −4.26917 | −17.862 |
| UGT1A6 | 1 | −4.22413 | −4.91623 |
| RNF150 | 1 | −4.16771 | 0 |
| GBP1 | 1 | −4.09511 | −7.4659 |
| CDH13 | 1 | −4.09377 | −1.81876 |
| RPS4Y2 | 1 | −4.07922 | 1.789499 |
| ID1 | 1 | −4.07902 | −1.19702 |
| IGFBP6 | 1 | −4.02618 | −3.19651 |
| PRICKLE1 | 1 | −4.01465 | −3.25904 |
| FRAS1 | 1 | −3.98435 | −1.06816 |
| GPRC5C | 1 | −3.94143 | −2.20771 |
| TSHZ2 | 1 | −3.93678 | 0 |
| SP110 | 1 | −3.92097 | −8.33054 |
| TSHZ3 | 1 | −3.89158 | 0 |
| IRF7 | 1 | −3.88008 | −5.31077 |
| TFCP2L1 | 1 | −3.79911 | −5.64592 |
| KLHDC8B | 1 | −3.70366 | −2.18648 |
| IFIH1 | 1 | −3.65978 | −8.78613 |
| NEBL | 1 | −3.64006 | −2.75499 |
| PDK4 | 1 | −3.63403 | 0 |
| P8 | 1 | −3.62499 | −1.07519 |
| NCOA7 | 1 | −3.62028 | −3.14289 |
| OASL | 1 | −3.6186 | 0 |
| SFRP1 | 1 | −3.60717 | −3.33534 |
| ADRB2 | 1 | −3.6005 | −7.32535 |
| PRRG2 | 1 | −3.58798 | −2.16193 |
| IRF1 | 1 | −3.54903 | −4.88511 |
| SP110 | 1 | −3.54245 | −8.60818 |
| NFIX | 1 | −3.49562 | −4.27031 |
| HSH2D | 1 | −3.49469 | −6.57252 |
| NUPR1 | 1 | −3.47694 | −1.1016 |
| AUTS2 | 1 | −3.44727 | −5.80848 |
| CH25H | 1 | −3.44105 | 0 |
| MME | 1 | −3.42257 | −3.38259 |
| CEL | 1 | −3.38582 | −1.97371 |
| SLC1A3 | 1 | −3.38279 | −2.55169 |

TABLE 2-continued

Downregulated genes expressed in terms of fold difference in either RWPE1-MYC or RWPE1-PI3K cells with a cut-off of <−2 after normalizing against the vector control RWPE1 cells.

| | RWPE1 | | |
|---|---|---|---|
| Symbol | Vector | PI3K (E545K) | MYC |
| OAS3 | 1 | −3.37572 | −4.84003 |
| P2RY5 | 1 | −3.36923 | −3.10518 |
| GBP4 | 1 | −3.32848 | −3.72049 |
| SUSD2 | 1 | −3.32179 | 0 |
| STAT1 | 1 | −3.317 | −7.77765 |
| HERC5 | 1 | −3.30749 | −26.7293 |
| ELF3 | 1 | −3.28097 | −4.19081 |
| RAET1G | 1 | −3.27051 | −1.1041 |
| HES4 | 1 | −3.26397 | −2.1495 |
| IL6 | 1 | −3.25509 | −3.73924 |
| PLSCR1 | 1 | −3.25128 | −5.09925 |
| NOTCH1 | 1 | −3.24542 | −1.5392 |
| PARP9 | 1 | −3.23719 | −4.95694 |
| AKR1C2 | 1 | −3.22758 | −2.09065 |
| CALML3 | 1 | −3.21559 | −3.42797 |
| PRIC285 | 1 | −3.20522 | −7.484 |
| RND3 | 1 | −3.20391 | −2.99375 |
| CPS1 | 1 | −3.18838 | 1.33824 |
| NINJ1 | 1 | −3.16788 | −1.44584 |
| COL8A1 | 1 | −3.15052 | −7.55795 |
| SNCA | 1 | −3.14852 | −2.52501 |
| UBE2H | 1 | −3.13817 | −2.5673 |
| PTPRM | 1 | −3.12065 | 1.918932 |
| IRF9 | 1 | −3.11836 | −13.022 |
| AHNAK | 1 | −3.11139 | −2.56856 |
| S1PR3 | 1 | −3.09794 | −4.16193 |
| COL8A1 | 1 | −3.09684 | 0 |
| NAV2 | 1 | −3.0429 | −1.5603 |
| AHNAK | 1 | −3.01399 | −2.70158 |
| SP100 | 1 | −3.00103 | −3.7716 |
| FXYD3 | 1 | −2.98965 | −3.21165 |
| STARD5 | 1 | −2.98829 | −3.84417 |
| SP100 | 1 | −2.98761 | −3.236 |
| PTGER4 | 1 | −2.9803 | −3.35191 |
| COL5A1 | 1 | −2.97542 | −3.3449 |
| CGNL1 | 1 | −2.95599 | 0 |
| DLL1 | 1 | −2.95361 | −4.96959 |
| HAS3 | 1 | −2.93769 | −4.85051 |
| TLE4 | 1 | −2.92651 | −2.38054 |
| FBXO2 | 1 | −2.91668 | −3.50251 |
| C15orf48 | 1 | −2.91543 | −1.73605 |
| FBXO32 | 1 | −2.874 | −2.99236 |
| TSC22D3 | 1 | −2.8608 | −2.28563 |
| IL13RA2 | 1 | −2.85721 | −3.26831 |
| C1QTNF1 | 1 | −2.85168 | −1.1121 |
| SNCA | 1 | −2.84333 | −2.18968 |
| KLF4 | 1 | −2.82996 | 1.191471 |
| PLTP | 1 | −2.81382 | 1.667983 |
| ECM2 | 1 | −2.81232 | 2.447139 |
| C5orf23 | 1 | −2.80702 | −1.66034 |
| MATN2 | 1 | −2.80379 | −3.7195 |
| IFI35 | 1 | −2.78241 | −8.54067 |
| GDF15 | 1 | −2.78075 | 1.20734 |
| PDZD2 | 1 | −2.77311 | −4.37154 |
| LRIG1 | 1 | −2.77302 | −2.75495 |
| PARP10 | 1 | −2.76716 | −3.58787 |
| EFEMP1 | 1 | −2.73839 | −12.8271 |
| ABCA1 | 1 | −2.73342 | −1.93387 |
| SPOCK1 | 1 | −2.73079 | 1.300084 |
| TAP1 | 1 | −2.72792 | −2.95213 |
| PARP12 | 1 | −2.72389 | −3.21894 |
| C14orf159 | 1 | −2.66409 | −2.1711 |
| H1F0 | 1 | −2.66214 | −3.18551 |
| PDPN | 1 | −2.65938 | 1.228458 |
| NNMT | 1 | −2.64692 | −5.21434 |
| C1orf116 | 1 | −2.6387 | −6.05598 |
| TRMT1 | 1 | −2.62477 | −1.93189 |
| MDK | 1 | −2.61659 | −2.24699 |
| CA12 | 1 | −2.61268 | 1.295919 |
| DKK3 | 1 | −2.61203 | −5.73642 |
| FAM46B | 1 | −2.60997 | −5.69141 |
| IFNGR1 | 1 | −2.60734 | −2.75367 |
| LAP3 | 1 | −2.6027 | −1.91627 |
| CFB | 1 | −2.60197 | −5.86999 |
| GAMT | 1 | −2.59296 | −2.24434 |
| TDRD7 | 1 | −2.58147 | −8.24047 |
| AKR1C3 | 1 | −2.54231 | −3.72025 |
| CEACAM1 | 1 | −2.54059 | 0 |
| ARMCX2 | 1 | −2.52824 | 1.293912 |
| SCD5 | 1 | −2.52258 | −2.11499 |
| DKK3 | 1 | −2.51378 | −5.36429 |
| UBE2L6 | 1 | −2.51067 | −6.74206 |
| TM4SF1 | 1 | −2.48929 | −5.70556 |
| SLC43A3 | 1 | −2.48614 | 1.166472 |
| EFEMP1 | 1 | −2.48131 | −13.2097 |
| C9orf3 | 1 | −2.47376 | −1.63753 |
| ZBTB16 | 1 | −2.47129 | −4.49531 |
| BCL6 | 1 | −2.46016 | −3.94866 |
| APOL3 | 1 | −2.45744 | −3.05898 |
| CYP2J2 | 1 | −2.4506 | −4.44102 |
| IL8 | 1 | −2.4491 | −2.62036 |
| TSC22D3 | 1 | −2.44766 | −2.04666 |
| CCL5 | 1 | −2.44673 | −9.50327 |
| MAP2 | 1 | −2.44317 | −2.51548 |
| C19orf66 | 1 | −2.43681 | −4.961 |
| FXYD3 | 1 | −2.4298 | −2.58134 |
| CPA4 | 1 | −2.42461 | 0 |
| LMO2 | 1 | −2.42267 | −2.60662 |
| PID1 | 1 | −2.42209 | −4.08724 |
| D4S234E | 1 | −2.42147 | −3.22768 |
| RBBP8 | 1 | −2.42131 | −2.37137 |
| STX10 | 1 | −2.41265 | −1.98528 |
| EFEMP1 | 1 | −2.40053 | −4.27066 |
| TRIM21 | 1 | −2.40041 | −4.2023 |
| UBE2L6 | 1 | −2.39853 | −3.83604 |
| KITLG | 1 | −2.38863 | −2.18432 |
| MN1 | 1 | −2.38314 | −1.2506 |
| DPYSL3 | 1 | −2.37977 | 1.278269 |
| ISG20 | 1 | −2.36002 | −7.67305 |
| PSMB9 | 1 | −2.35768 | −7.74624 |
| NT5E | 1 | −2.35693 | −3.01737 |
| APOE | 1 | −2.35637 | −2.71449 |
| FBLN1 | 1 | −2.3551 | −4.2408 |
| UBA7 | 1 | −2.35421 | 0 |
| SOD2 | 1 | −2.35192 | −2.40564 |
| PROS1 | 1 | −2.33164 | −3.33977 |
| HBEGF | 1 | −2.32723 | 1.632474 |
| LPHN1 | 1 | −2.31898 | 2.72042 |
| CXCL2 | 1 | −2.31796 | −3.233 |
| TMEM156 | 1 | −2.30881 | −1.49085 |
| ZNFX1 | 1 | −2.30577 | −4.00188 |
| SSBP2 | 1 | −2.30116 | −2.59611 |
| VAMP5 | 1 | −2.2968 | −3.18909 |
| MBP | 1 | −2.27955 | −1.22528 |
| ZC3HAV1 | 1 | −2.27785 | −4.22738 |
| IRS2 | 1 | −2.27749 | −2.3939 |
| SAA1 | 1 | −2.27607 | −7.09373 |
| LIMCH1 | 1 | −2.25982 | −4.10693 |
| IRX4 | 1 | −2.24545 | −3.35408 |
| H19 | 1 | −2.23655 | −7.11566 |
| KCNMA1 | 1 | −2.23573 | −2.1332 |
| ALDH3A2 | 1 | −2.23002 | −2.51574 |
| GAMT | 1 | −2.22638 | −2.09051 |
| CRYAB | 1 | −2.22188 | −2.19121 |
| DHX58 | 1 | −2.19676 | −3.48679 |
| ENC1 | 1 | −2.17211 | −2.89626 |
| PARP14 | 1 | −2.16842 | −4.22674 |
| HTRA1 | 1 | −2.15993 | −2.42448 |
| C10orf59 | 1 | −2.15484 | 1.108868 |
| TFPI | 1 | −2.1438 | −4.71083 |
| PODXL | 1 | −2.13888 | 1.806846 |
| ETS2 | 1 | −2.12799 | −1.95914 |
| DHRS2 | 1 | −2.11015 | −3.003 |
| IGFBP4 | 1 | −2.09946 | −1.21718 |

TABLE 2-continued

Downregulated genes expressed in terms of fold difference in either RWPE1-MYC or RWPE1-PI3K cells with a cut-off of <−2 after normalizing against the vector control RWPE1 cells.

| | RWPE1 | | |
|---|---|---|---|
| Symbol | Vector | PI3K (E545K) | MYC |
| C10orf54 | 1 | −2.09598 | −2.94343 |
| CFH | 1 | −2.08862 | −2.49672 |
| FLRT2 | 1 | −2.0816 | −1.15986 |
| FOXA1 | 1 | −2.08024 | −3.46667 |
| C1S | 1 | −2.07987 | −2.95596 |
| NPTX2 | 1 | −2.06893 | 1.557073 |
| ATF3 | 1 | −2.06752 | 1.07467 |
| KRT13 | 1 | −2.05874 | −2.62563 |
| AOX1 | 1 | −2.05855 | 0 |
| CDH11 | 1 | −2.05177 | −3.59808 |
| TNFRSF14 | 1 | −2.04958 | −1.71062 |
| STAT2 | 1 | −2.04954 | −4.87075 |
| SLC43A3 | 1 | −2.04937 | 1.417271 |
| NOTCH3 | 1 | −2.04889 | 5.393062 |
| PHF11 | 1 | −2.03569 | −2.45454 |
| STS-1 | 1 | −2.02838 | −1.35028 |
| EIF2AK2 | 1 | −2.02668 | −3.49876 |
| IFITM2 | 1 | −2.02407 | −3.87637 |
| KLF6 | 1 | −2.01916 | −1.84199 |
| BASP1 | 1 | −2.00465 | −1.86717 |
| OSBP2 | 1 | −1.97101 | −3.60614 |
| LEPREL1 | 1 | −1.96294 | −5.84162 |
| SOD2 | 1 | −1.93428 | −2.33246 |
| PLAC8 | 1 | −1.93272 | −10.2138 |
| PHF11 | 1 | −1.91247 | −2.45303 |
| PIK3R1 | 1 | −1.89025 | −3.47858 |
| CBR3 | 1 | −1.86845 | −3.24695 |
| SAA1 | 1 | −1.86567 | −8.07595 |
| MYADM | 1 | −1.84083 | −2.38509 |
| REC8 | 1 | −1.8097 | −2.54367 |
| PRSS23 | 1 | −1.80801 | −2.5119 |
| KRT14 | 1 | −1.8055 | −3.95635 |
| KRT19 | 1 | −1.80052 | −5.97256 |
| LY6E | 1 | −1.79411 | −2.31856 |
| SAA2 | 1 | −1.78685 | −5.57727 |
| HRASLS3 | 1 | −1.78336 | −3.9676 |
| ZNF256 | 1 | −1.78203 | −3.42712 |
| GALNT10 | 1 | −1.77767 | −2.05615 |
| ZSCAN18 | 1 | −1.7735 | −5.8675 |
| DPYD | 1 | −1.75581 | −2.85288 |
| TMEM40 | 1 | −1.7444 | −3.29025 |
| ASCL2 | 1 | −1.74426 | −3.7976 |
| FEZ1 | 1 | −1.73308 | −2.00585 |
| FAM46A | 1 | −1.7221 | −3.39868 |
| TACSTD2 | 1 | −1.72204 | −4.46011 |
| ARID5B | 1 | −1.69279 | −4.48695 |
| HCP5 | 1 | −1.68987 | −5.48799 |
| LPXN | 1 | −1.68657 | −2.39644 |
| IFITM3 | 1 | −1.68021 | −3.37424 |
| ZBTB16 | 1 | −1.64861 | −2.35628 |
| PPP1R3C | 1 | −1.63292 | −3.31748 |
| FOS | 1 | −1.62189 | −2.43906 |
| IGFBP7 | 1 | −1.55948 | −4.80971 |
| NMI | 1 | −1.55433 | −3.49245 |
| FAM111A | 1 | −1.54744 | −3.2378 |
| RAB7B | 1 | −1.53697 | −3.0797 |
| EPDR1 | 1 | −1.50587 | −3.14162 |
| CLIC3 | 1 | −1.49496 | −3.21748 |
| KRT5 | 1 | −1.47614 | −3.16513 |
| C1RL | 1 | −1.45983 | −2.57394 |
| PSMB8 | 1 | −1.43906 | −2.4564 |
| EMP1 | 1 | −1.43275 | −3.40126 |
| CAV2 | 1 | −1.41908 | −2.50767 |
| LOX | 1 | −1.40002 | −2.6319 |
| PSMB8 | 1 | −1.39608 | −2.53212 |
| PSMB8 | 1 | −1.39003 | −2.11675 |
| DNER | 1 | −1.37583 | −2.12381 |
| CASP1 | 1 | −1.36673 | −4.60663 |
| BST2 | 1 | −1.31658 | −5.99401 |
| SAA1 | 1 | −1.30334 | −2.97076 |
| C1orf225 | 1 | −1.29701 | −2.264 |
| ABCC3 | 1 | −1.29217 | −3.06003 |
| KRT16 | 1 | −1.27737 | −2.12919 |
| SQRDL | 1 | −1.27004 | −2.71467 |
| S100A8 | 1 | −1.25056 | −5.09928 |
| CASP1 | 1 | −1.2314 | −4.31351 |
| SLC47A2 | 1 | −1.21808 | −2.47908 |
| OPTN | 1 | −1.21739 | −2.3348 |
| TFAP2C | 1 | −1.21697 | −4.82067 |
| TIMP2 | 1 | −1.2166 | −3.20078 |
| PLEKHA4 | 1 | −1.14712 | −2.10986 |
| IRS1 | 1 | −1.09989 | −2.04009 |
| ARHGDIB | 1 | −1.0664 | −4.20726 |
| C1orf53 | 1 | −1.05763 | −2.70324 |
| FAM134B | 1 | 0 | −4.58487 |
| HOXA5 | 1 | 1.035466 | −3.57871 |
| FST | 1 | 1.091432 | −3.08217 |
| FST | 1 | 1.096288 | −8.719 |
| S100A9 | 1 | 1.110295 | −2.93526 |
| IL1B | 1 | 1.110625 | −2.09728 |
| ADM | 1 | 1.135267 | −4.52446 |
| CAMK2B | 1 | 1.230406 | −2.28352 |
| IFI16 | 1 | 1.242815 | −5.96296 |
| KIF20A | 1 | 1.299295 | −2.39991 |
| ZNF415 | 1 | 1.30571 | −3.33475 |
| FGFBP1 | 1 | 1.572931 | −8.86766 |
| C10orf116 | 1 | 1.597527 | −2.28262 |
| ADFP | 1 | 1.638751 | −3.57931 |
| PI3 | 1 | 1.705046 | −2.77734 |
| RRAGD | 1 | 1.825306 | −3.24677 |
| C1orf115 | 1 | 2.042584 | −2.0006 |
| PHACTR3 | 1 | 3.263027 | −2.71081 |

Example 2

IFNGR1 is a Direct Target of EZH2 in MYC-Driven, but not PI3K-Driven Prostate Cancer Cells The mechanism of loss of IFNGR1 and its downstream IFN responsive genes could result from epigenetic modifications such as DNA methylation or histone modifications. Given a well-known role of EZH2 in advanced prostate cancer, and that both MYC and PI3K signaling have been recently shown to regulate EZH2 expression or activity, the possible role of EZH2 in control of IFN signaling was investigated in MYC and PI3K-transformed cells. To this end, it was found that the ectopic overexpression of EZH2 in RWPE1 cells is able to selectively downregulate IFNGR1 (but not IFNAR1) and other IFN responsive genes (FIG. 2A). Notably, in RWPE1-MYC cells, EZH2 knockdown was able to restore the expression of IFNGR1 (but not IFNAR1), which however was note seen in RWPE1-PI3K cells (FIG. 2B). Thus, EZH2 appears to be involved in IFNGR1 repression only in MYC-driven cells, but not in PI3K-driven cells.

MYC has been previously known to upregulate EZH2 expression via downregulating miR-26a/b. It has also been recently shown to affect EZH2 activity by antagonizing PI3K-AKT-mediated phosphorylation of EZH2 on serine 21. Akt-induced EZH2 phosphorylation on serine 21 is inhibitory to EZH2 gene silencing activity but promotes its Polycomb-independent oncogenic activity. Indeed, we found that MYC-driven RWPE cells showed concurrent reductions of phosphorylation on both AKT (S473) and EZH2 (S21) as compared with PI3K-driven cells (FIG. 2C).

Meanwhile, MYC overexpression only led to a modest decrease in miR-26a, and consistently a modest induction of EZH2 mRNA level (FIGS. 9A and B). These findings suggest that MYC overexpression in our system more likely modulates the EZH2 activity through counteracting AKT-mediated EZH2 inhibition, rather than through miR-26a-mediated mechanism.

Next, we investigated whether EZH2 directly represses IFNGR1 as well as the downstream IFN genes. Chromatin immunoprecipitation (ChIP) followed by quantitative PCR analysis in the vicinity of the promoter region of IFNGR1 (FIG. 2D) shows significant EZH2 enrichments in RWPE1-MYC cells (FIG. 2E, compared with the positive control gene CNR1), but not in RWPE1-PI3K and the vector control RWPE cells (FIG. 2E). In addition, no EZH2 enrichment was found in genes downstream of IFNGR1 (FIG. 9C). Therefore, the transcriptional inactivation of IFN-JAK-STAT1 signaling seen in MYC-driven cells may stem from a direct suppression of IFNGR1 by EZH2.

Similar to transformed RWPE1-MYC cells, we found a significant EZH2 enrichments in the IFNGR1 promoter in two prostate cancer cell lines, DU145 and PC3 which have been previously known to carry MYC amplification or sensitive to MYC inhibition, but not in LNCaP and 22RV1 cells which are less sensitive to MYC knockdown, and thus appeared to be MYC-independent (FIG. 2F, FIG. 9D). Furthermore, MYC knockdown in DU145 cells resulted in much reduced enrichments of both EZH2 and H3K27me3 in the IFNGR1 promoter (FIG. 2G), which however was not seen in LNCaP cells. This data further supports that EZH2-mediated silencing of IFNGR1 is MYC-dependent.

In addition, we found a partial DNA hypermethylation in the IFNGR1 promoter in RWPE1-PI3K cells and LNCaP cells but not in RWPE1-MYC and DU145 cells (FIG. 9E). Thus, using both transformed RWPE1 cells and prostate cancer cell lines we conclude that EZH2-mediated repression of IFNGR1 is restricted to MYC-associated prostate cancer cells, while the IFNGR1 downregulation in PI3K-transformed RWPE1 or LNCaP cells is independent of EZH2, and might be associated with the promoter DNA hypermethylation.

Example 3

IFNGR1 is Downregulated in a Subset of Metastatic Prostate Tumors Associated with MYC To validate the IFNGR1 downregulation in clinical samples, we examined the expression of IFNGR1, together with MYC and EZH2 in a previously published prostate cancer gene expression dataset which covers the disease progression from benign prostatic epithelium to metastatic prostate cancer. We found that a subset of metastatic tumors show strong upregulations of MYC and EZH2, while IFNGR1 and the downstream IFN genes were downregulated towards the metastatic progression (FIG. 3A).

Figure 3:
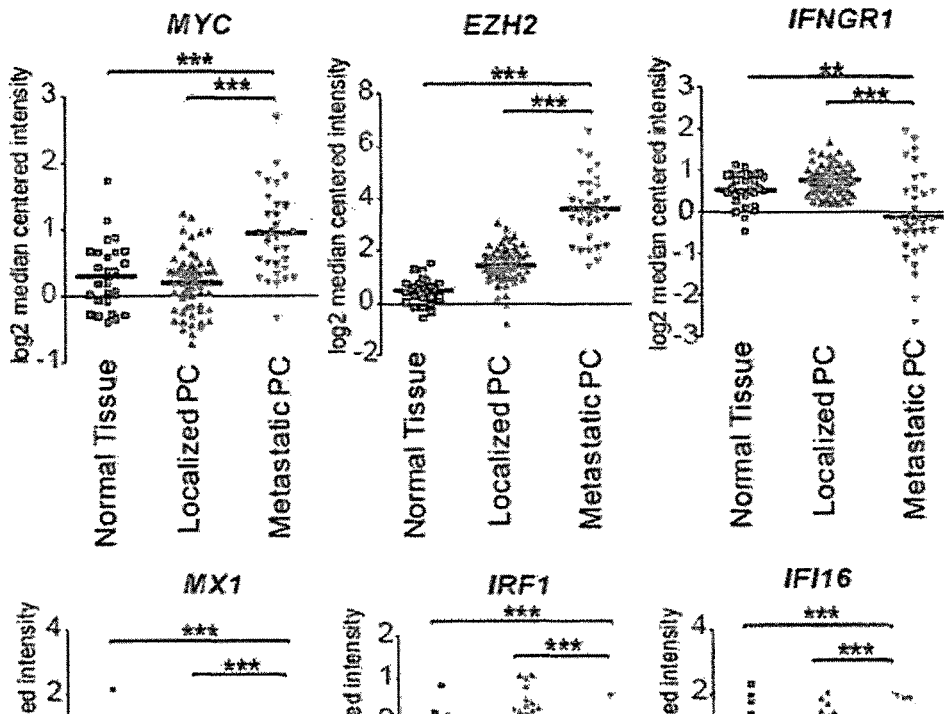
FIG. 3 is a series of scatter plots and immunohistochemistry images showing the inverse relationship between MYC/EZH2 and IFNGR1 expression levels in advanced prostate cancer.
Figure 3:
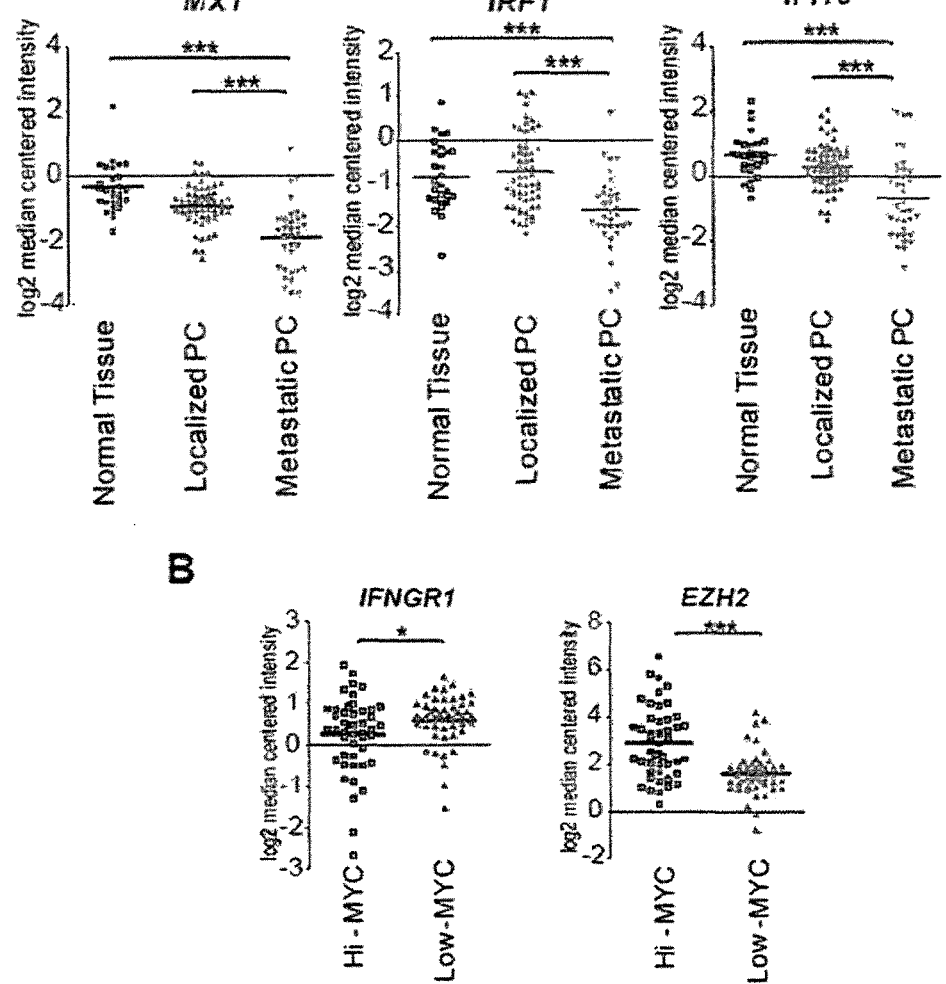
Figure 3:
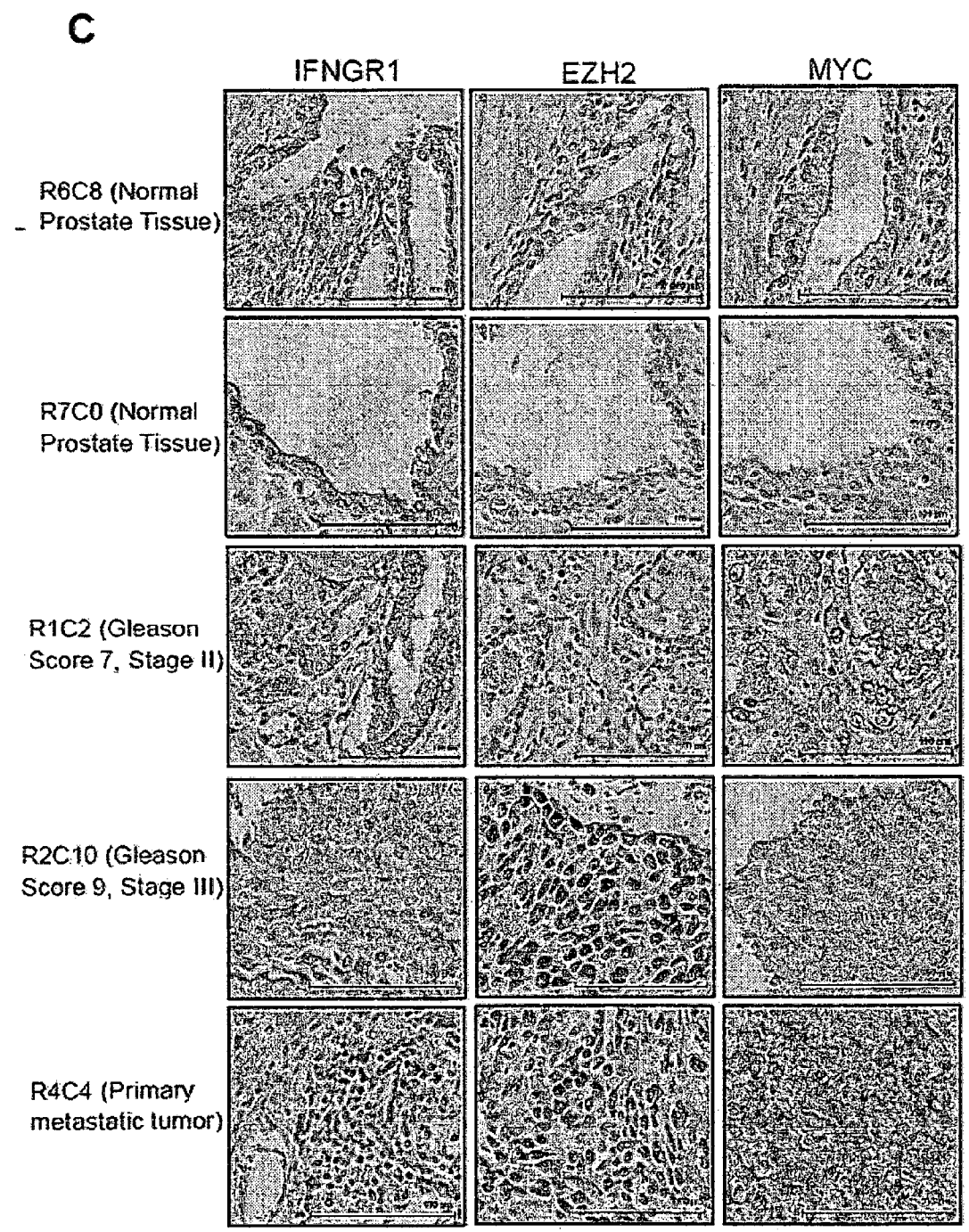

Moreover, when these tumors were stratified based on the MYC levels, we found that high MYC tumors tend to express higher levels of EZH2 and lower levels of IFNGR1 (FIG. 3B). Immunohistochemistry (IHC) analysis in a set of prostate tissues of different grades and stages confirms that high grade and metastatic tumors express higher levels of MYC and EZH2 but lower IFNGR1 in these tumors (FIG. 3C). Thus, our finding suggests that IFNGR1 downregulation by EZH2 may occur in a subset of metastatic prostate tumors associated with MYC.

Example 4

Figure 4:
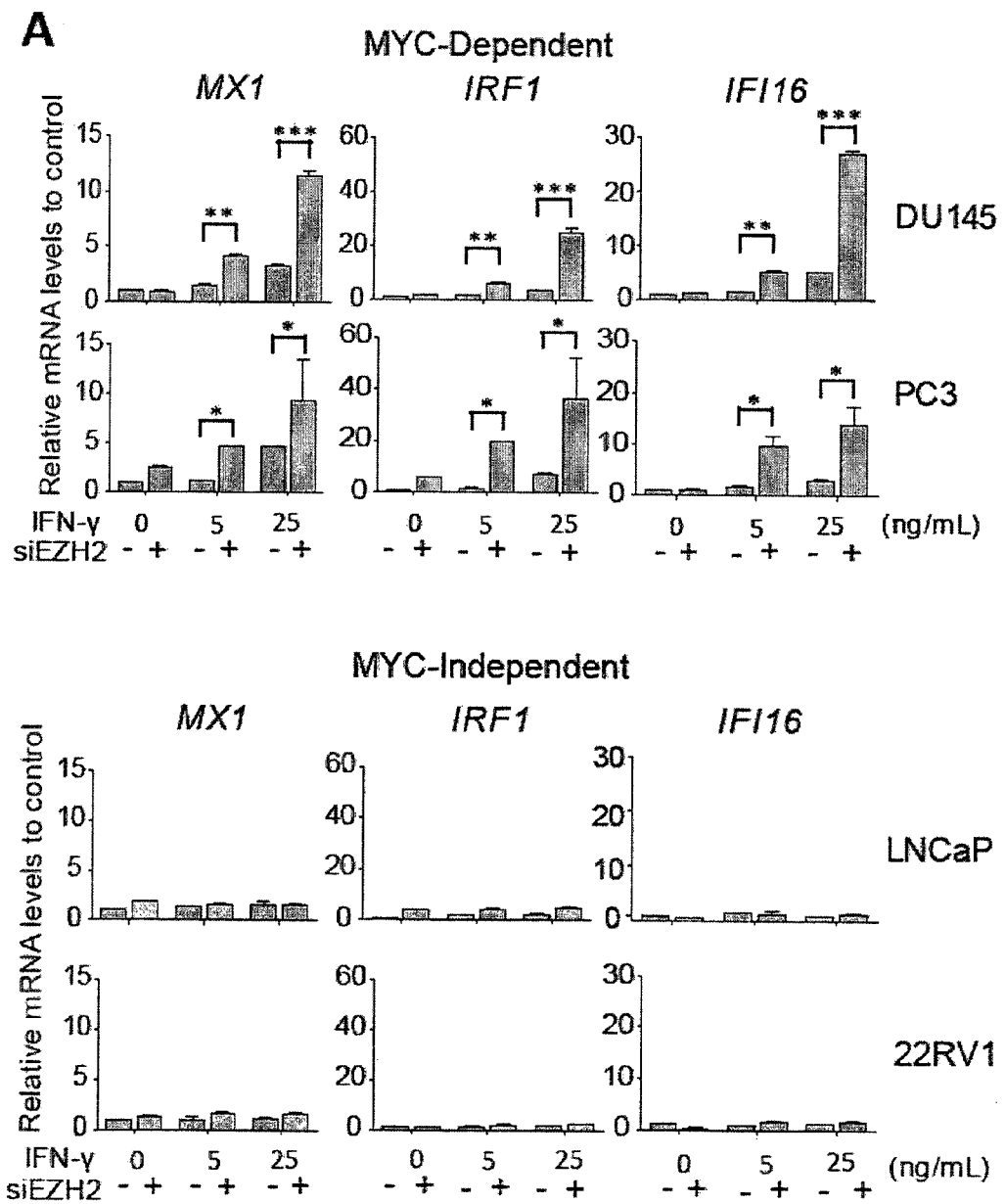
FIG. 4 is a series of graphs and western blots showing that MYC/EZH2-mediated inactivation of IFNγ-JAK-STAT1 signaling confers growth and survival advantages.
Figure 4:
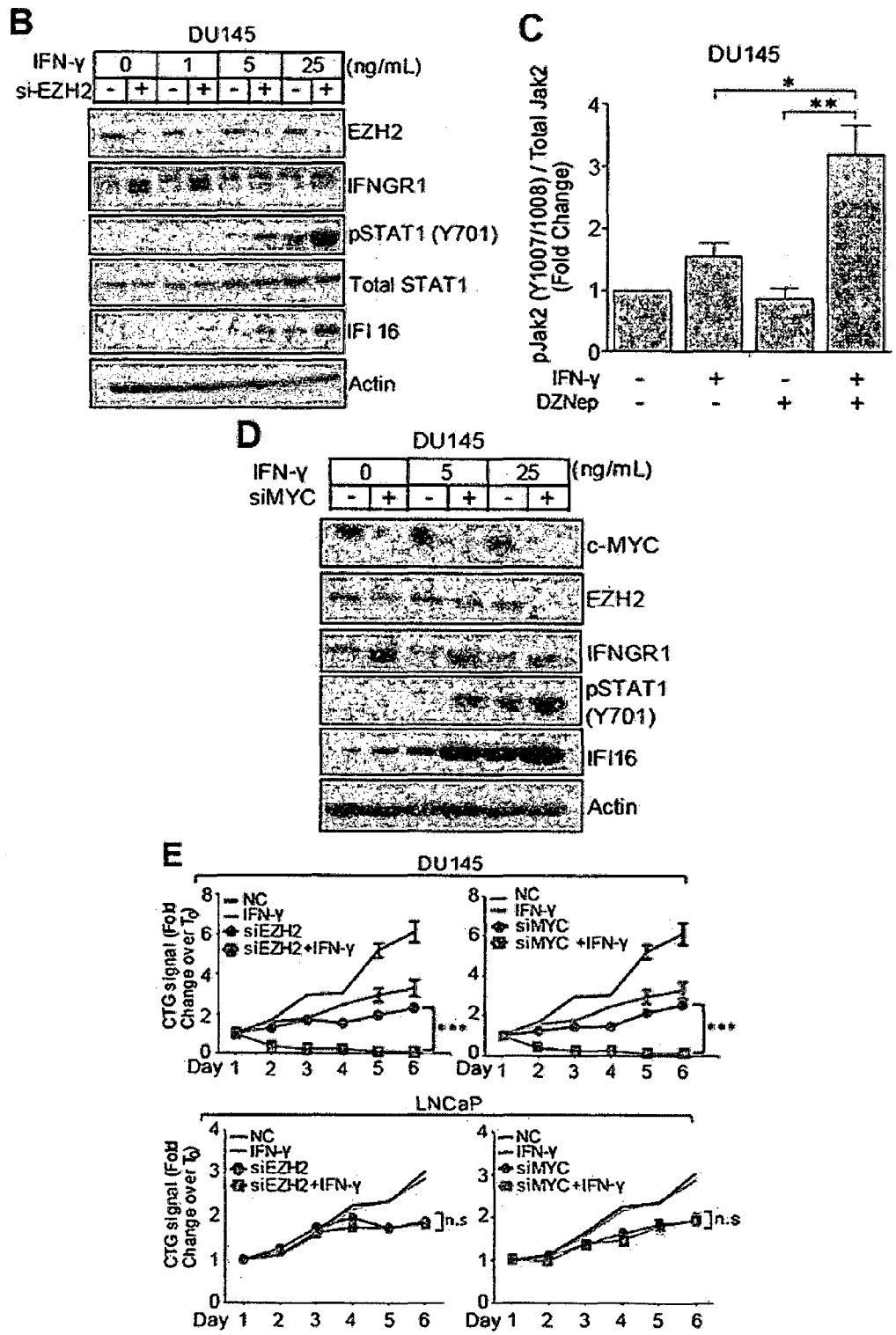
Figure 4:
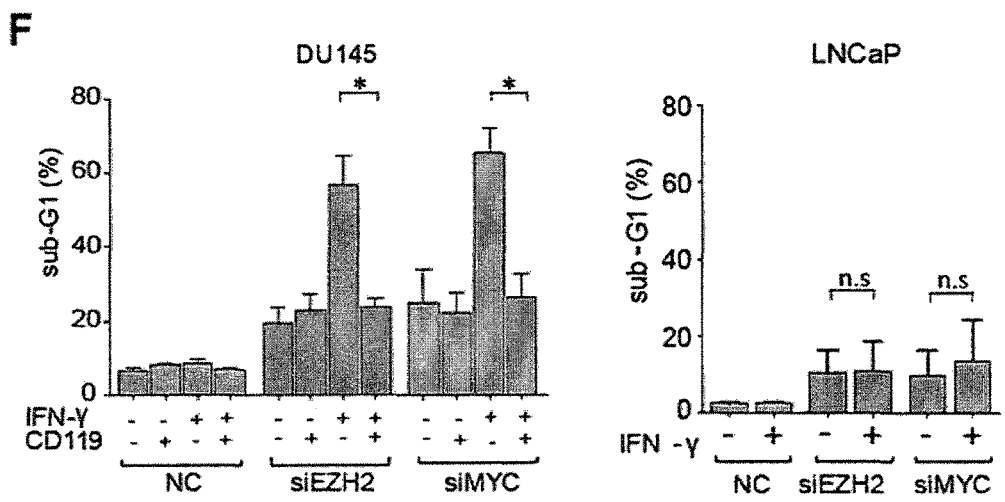
Figure 4:
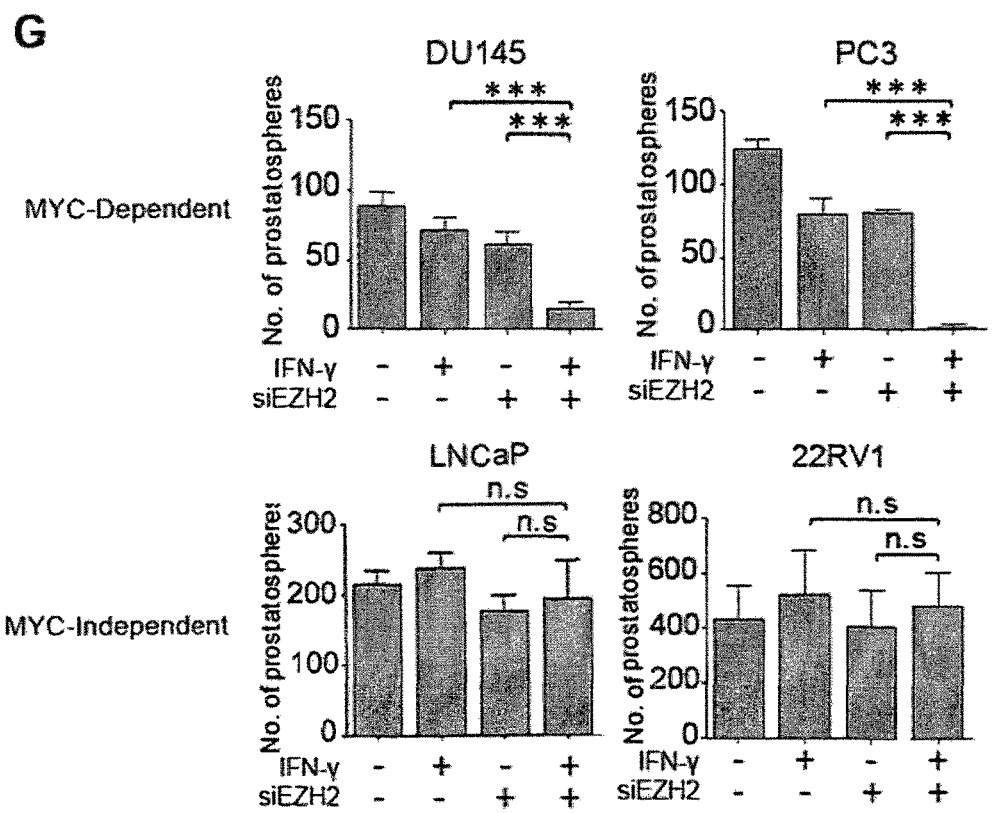
Figure 4:
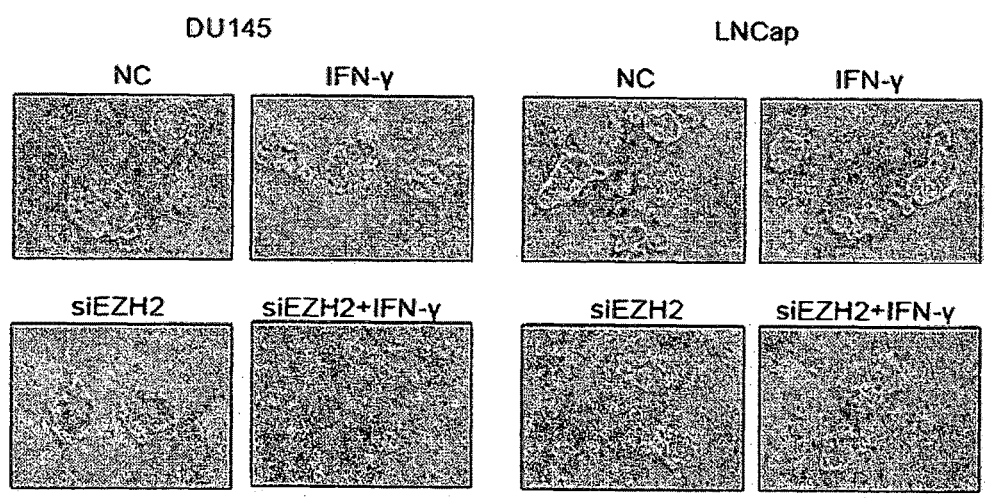

EZH2-Mediated Inactivation of IFN-γ-JAK-STAT1 Signaling Pathway Confers Growth and Survival Advantages in MYC-Dependent Prostate Cancer Cells Activation of IFN-γ-STAT1 signaling is known to be tumor suppressive through the induction a number of IFN responsive genes, including the apoptosis-promoting IRF1. Loss of IFNGR1 expression by EZH2 is expected to cause a reduced sensitivity to IFN-γ treatment, resulting in defective activation of JAK-STAT1 signaling and its downstream target genes. Consistent with this hypothesis, EZH2 knockdown in MYC-dependent DU145 and PC3 cells, but not in MYC-independent LNCaP and 22RV1 cells, resulted in robust activation of IFN genes in response to IFN-γ stimulation (FIG. 4A). Consistently, EZH2 knockdown in DU145 cells restored the IFNGR1 protein expression, enhanced the STAT1 phosphorylation and the expression of IFI6, a downstream target gene of STAT1 (FIG. 4B), as well as JAK2 phosphorylation in response to IFN-γ stimulation (FIG. 4C). Consistent with MYC being upstream of EZH2, MYC knockdown in DU145 cells resulted in decreased EZH2 expression, which gave rise to a similar increase in IFNGR1 expression and STAT1 activation in response to IFN-γ stimulation (FIG. 4D).

Phenotypically, we found that, either MYC or EZH2 knockdown, when combined with IFN-γ treatment, resulted in remarkable synergy in cell growth regression in MYC-dependent DU145 cells, indicating an induction of cell death (FIG. 4E, top). By contrast, no such an effect was seen in MYC-independent LNCaP cells (FIG. 4E, bottom). Further assessing cell death by sub-G1 DNA suggested an apoptosis induction following EZH2 or MYC knockdown, in combination with IFN-γ treatment, in DU145 but not in LNCaP cells (FIG. 4F). Crucially, the enhanced apoptosis induced by the combination conditions were IFNGR1-dependent, as the addition of a specific IFNGR1 neutralizing antibody CD119, which presumably blocks the binding of IFN-γ ligand to the IFNGR1, nearly completely abolished this apoptosis induction upon EZH2 or MYC knockdown (FIG. 4F).

As EZH2 has been linked to cancer stemness, the ability of EZH2 knockdown in tumorsphere formation in prostate cancer cells (prostatosphere), a growth feature associated with tumor initiating cells was further assessed. The cancer stem cell (CSC) hypothesis proposes that a population of tumor cells bearing stem cell properties is responsible for the origin and maintenance of tumors. Normal and cancer stem cells possess the ability to grow in vitro as self-renewing spheres, but the molecular basis of this phenotype remains largely unknown. A comprehensive culture system to grow prostatospheres (PSs) from both cancer cell lines and patient tumors has been established. Gene expression microarrays were then carried out to gain insight on the molecular pathways that sustain the PS tumor initiating cell (TIC) phenotype.

Prostatospheres are believed to be tumor-initiating cells that are responsible for tumor formation and prostatospheres appear in some examples to be resistant to chemotherapy. Hence, prostatospheres may contribute to chemo-resistance and disease progression/relapse post-treatment. Accordingly, it is an object of the invention to demonstrate the unexpected effect of the combination as described herein in the treatment of prostatospheres. In fact, the prostatospheres are highly sensitive to the combination as described herein and the use of said combination may represent an effective treatment strategy to completely eradicate the tumor cells including the tumor initiating cancer stem cells that show resistant to conventional chemotherapy.

As shown in FIG. 4G, EZH2 knockdown in combination with IFN-γ efficiently inhibited the tumorsphere formation in MYC-dependent DU145 and PC3 cells, but not in MYC-independent LNCaP and 22RV1 cells (FIG. 4G). Taken together, these findings support that MYC and EZH2 act concertedly in the same pathway to promote growth and survival advantages through inactivation of IFN-γ-STAT1 tumor suppressor pathway. Restoring the IFN-γ-STAT1 signaling following EZH2 knockdown is able to sensitize the IFN-γ treatment in MYC-dependent prostate cancer cells.

Example 5

Pharmacologic Depletion of EZH2 by DZNep Mimics EZH2 Knockdown to Restore IFNGR1 Expression and Sensitize IFN-γ Treatment The surprising and unexpected finding as described above lead the inventors to test pharmacologic approaches to restore IFN signaling. To this end, two exemplary types of pharmacologic agents were exploited: one is the histone methylation inhibitor deazaneplanocin A (DZNep), which though not being specific is nevertheless able to effectively deplete EZH2/PRC2, leading to activation of EZH2 target genes; the second is recently reported catalytic inhibitors of EZH2 that can specifically inhibit H3K27me3 but do not affect EZH2. The results show that pharmacological depletion of EZH2 by DZNep in DU145 cells was able to mimic the EZH2 knockdown and induced the expression of IFNGR1, which, when combined with IFN-γ, led to strong inductions of IFN genes (FIG. 5A), as well as STAT1 phosphorylation (FIG. 5B). Again, in agreement with the selective repression of IFNGR1 by EZH2, DZNep treatment did not change IFNAR1 expression (FIGS. 5A and 5B).

Like EZH2 knockdown, DZNep was able to induce a robust apoptosis when combined with increasing doses of IFN-γ in DU145 but not in LNCaP cells (FIG. 5C). Similarly, consistent with the MYC-dependency, such an induction of apoptosis was only seen in RWPE1-MYC cells, but not in RWPE1-PI3K or control RWPE cells (FIG. 10A). As a comparison, we also show that the other epigenetic compounds such as histone deacetylase inhibitors SAHA and TSA as well as DNA methylation inhibitor 5'Aza did not give rise to such a response (FIG. 10B), underscoring a unique ability of DZNep in this scenario. Again, the apoptosis induced by the drug combination was inhibited by the neutralizing antibody (CD119) of the IFN-γ receptor (FIG. 5D), which was accompanied by the abolished induction of STAT1 phosphorylation and PARP cleavage (FIG. 5E). We also show that Axon 1588, a small molecule inhibitor of JAK2, could similarly rescue DU145 cells from apoptosis (FIG. 10C). These findings, taken together, demonstrate that the apoptosis induced by the combination of DZNep and IFN-γ is largely mediated through the specific activation of IFN-γ-STAT1 signaling pathway.

Moreover, the co-treatment of DZNep and IFN-γ was also able to show a combinatorial effect in growth inhibition in MYC-dependent DU145 and PC3 cells but not in MYC-independent LNCaP and 22RV1 cells (FIG. 5F). Most strikingly, this combination nearly completely eliminated the formation of DU145 or PC3-derived prostatospheres but had no effect on LNCaP or 22RV1-derived prostatospheres (FIG. 5G). Consistently, we detected drastic increase in the expression of IFN genes in DU145 prostatospheres upon the combination treatment (FIG. 10D). These findings indicate that DZNep is able to recapitulate the EZH2 knockdown and synergize with IFN-γ to induce apoptosis, cell proliferation and tumorsphere inhibition in MYC-dependent prostate cancer cells.

Example 6

Therapeutic Effect of Combined DZNep and IFN-γ Treatment In Vivo

To confirm the above findings in vivo, we established the DU145 xenografts in athymic mice and treated them with vehicle, DZNep, IFN-γ, or both. Treatment with DZNep or IFN-γ alone slowed down the tumor growth, while the combination treatment resulted in a complete tumor growth arrest in average (p<0.01) (FIG. 6A) and a few of these tumors showed tumor repression (data not shown). Throughout the study, both single or combination treatment were well tolerated in mice without overt signs of toxicity or weight loss >10%, encouraging a potential future application of this treatment in the clinic (FIG. 6B). Immunohistochemistry (IHC) analyses of tumors resected from the mice confirmed the downregulation of EZH2 and upregulation of IFNGR1 within the tumors treated with DZNep or DZNep combined with IFN-γ (FIG. 6C). Thus, the combination of DZNep and IFN-γ is also effective in the xenograft tumor model and is able to induce the expected molecular changes within the tumors. Collectively, our data demonstrated a therapeutic approach that may provide benefit in advanced prostate cancers that undergo EZH2-mediated IFNGR1 silencing.

Example 7

Catalytic Inhibitors of EZH2 Fail to Recapitulate the EZH2 Knockdown Effects

Next, we wanted to test whether or not the catalytic EZH2 inhibitors, which have been recently developed to selectively inhibit EZH2-mediated H3K27me3 and kill non-Hodgkin's lymphomas harboring EZH2 activating mutations, are, able to mimic the EZH2 knockdown. As shown in FIG. 7A, DU145 cells treated with such an EZH2 inhibitor (GSK343) up to 2.5 µM for 3 days did not show an induction of IFNGR1, despite the efficient depletion of H3K27me3 at as low as 0.1 µM. Cells treated with another EZH2 inhibitor, GSK126, in higher doses (up to 10 µM) for 10 days only showed a modest induction of IFNGR1 (FIGS. 7A and 7B). In contrast, DZNep, which depleted EZH2, as well as the other two PRC2 proteins EED and SUZ12, induced a marked expression of IFNGR1, albeit at a much lower efficiency in depleting H3K27me3 (FIGS. 7A and 7B). At the IFNGR1 gene promoter level, we saw that DZNep treatment reduced both EZH2 and H3K27me3 enrichments, though GSK126 was more efficiently depleted H3K27me3 (FIG. 7C). Accordingly, unlike the DZNep/IFN-γ treatment, we failed to see an apoptotic effect of GSK343/GSK126 in combination with IFN-γ in DU145 cells, treated for either 3 days or 10 days (FIG. 7D). Moreover, GSK126/IFN-γ combination also had no effect on DU145 tumorsphere formation (FIG. 7E). Taken together, these findings suggest that although H3K27me3 is a repressive hallmark associated with PRC2 activity, simply inhibiting H3K27me3, without affecting PRC2, is insufficient to induce a robust IFNGR1 expression and thus unable to mimic EZH2 knockdown. Thus, additional mechanisms might be required to coordinate with H3K27me3 to implement PRC2-mediated IFNGR1 silencing in the absence of gain of function EZH2 mutations in epithelial tumors. This result is consistent with a very recent report showing that a peptide blocking EZH2-EED binding, which leads to EZH2 downregulation, is able to induce the loss of cell viability in solid tumor cells, while GSK126 is unable to do so though it has a much greater potency in inhibiting H3K27me3.

Example 8

EZH2-Mediated IFNGR1 Repression Occurs Widely in Human Cancers

Apart from advanced prostate cancer, Oncomine analysis also shows that the upregulation of EZH2 accompanied by the down regulation of IFNGR1 is commonly observed in many other cancer types (FIG. 11A). In particular, the reverse correlation of EZH2 with IFNGR1 is also clearly shown in MYC-driven Burkitt's lymphoma vs. other types of lymphomas (FIGS. 11B and C), indicating that EZH2-mediated IFNGR1 expression may also occur in other MYC-driven cancers.

As we have previously shown that EZH2 epigenetic gene silencing activity is more prevalent in ER positive breast cancer cells, we sought to further validate the EZH2-mediated IFNGR1 repression in breast cancer. Data extracted from Gene expression-based Outcome for Breast cancer Online (GOBO) (co.bmc.lu.se/gobo) shows the downregulation of IFNGR1 in luminal subtype of breast cancer in both cell lines and clinical samples (FIGS. 12A and B). Using both western blotting and immunohistochemistry (IHC) analyzes we confirmed the downregulation of IFNGR1 protein in both ER+luminal breast cancer cell lines (FIG. 12C) and ER+primary tumor specimen relative to the ER− counterparts (FIG. 12D).

IFNGR1 downregulation in ER+ tumors seems to be clinically significant as it is associated with a poorer distant metastasis free survival (DMFS) in ER+ tumors but not in ER− tumors (FIG. 11E). As expected, EZH2 knockdown or DZNep treatment in ER+ luminal MCF7 cells led to an induction of IFNGR1 at both mRNA and protein levels but this was not seen in ER− basal like MDA-MB-231 cells (MB231) (FIG. 11F). ChIP analysis showed the enrichments of EZH2 and H3K27me3 in the IFNGR1 promoter in MCF7 but not MB-231 cells (FIG. 11G). Finally, combination of DZNep and IFN-γ resulted in robust apoptosis in luminal MCF-7 and T47D cells, but not in basal-like cell lines (FIG. 11H). Consistently, in both MCF-7 and T47D cells, we see that DZNep treatment restored the IFNGR1 expression, increased STAT1 activation and PARP cleavage when co-treated with IFN-γ (FIG. 11I). Thus, EZH2 represses IFNGR1 expression in ER+ luminal breast cancer cells to render susceptibility to the combined treatment with DZNep and IFN-γ.

Immunohistochemistry (IHC) was used to validate the Oncomine observation in liver and lung and cancers. In liver cancer, EZH2 upregulation and IFNGR1 downregulation occur mainly in high-grade tumors (FIGS. 13A and B). In a series of liver cell lines showing various levels of IFNGR1 expression, DZNep/IFN-γ combination induced strong apoptosis in cell lines with lower level of IFNGR1 but not in the cell line with high IFNGR1 (FIG. 13C). In lung cancer, EZH2 upregulation and IFNGR1 downregulation occur mainly in SCLC and metastatic lung cancer as well as a subset of NSCLC (FIGS. 13A and B). Again, DZNep/ IFN-γ treatment was more effective in NSCLC lines showing the higher EZH2 and lower IFNGR1 (FIGS. 14D and F). Taken together, these findings suggest that EZH2-mediated IFNGR1 repression occurs in subsets of multiple human cancers and the expression levels of EZH2 and IFNGR1 might be used as a biomarker strategy to identify the cancer patients that may potentially benefit from EZH2 and IFN-γ-based therapies.

The inventors interestingly identified a common EZH2 target that may be of therapeutic importance in many cancers. By analyzing the MYC-mediated transcriptional alteration in prostate cancer cells, a defective IFN-JAK-STAT1 signaling pathway inactivated by EZH2 in a MYC-dependent manner was uncovered. In one example, it is shown that the direct silencing of IFNGR1 by EZH2 mediates the inactivation of this pathway, rendering the cancer cells insensitive to IFN γ treatment. As such, restoration of IFNGR1 expression by EZH2 inhibition, either through gene knockdown or pharmacologic depletion, sensitizes the ability of interferon γ to activate the downstream STAT1 tumor suppressor pathway, leading to robust apoptosis. In the present disclosure, the inventors show for the first time that this molecular mechanism is MYC-dependent, which is consistent with MYC being an upstream regulator of EZH2

Cell Culture and Treatments

Epithelial cell lines were obtained from the American Type Culture Collection and cultured them according to the recommended protocols. MB231, BT549, MCF7, T47D, BT474, MB361, MB415, MB436, Hs578T, MB157, PC3, DU145 cell lines were grown in Dulbecco's modified Eagle's medium (DMEM) supplemented with 10% fetal bovine serum (FBS). VCap cells were grown in the addition of 1% sodium pyruvate and 1% sodium bicarbonate. SKBR3 cells were maintained in McCoy's 5A medium. HCC1806, HCC1937, 22RV1, and LNCaP were maintained in RPMI medium supplemented with 10% FBS.

HMEC and MCF10A normal breast epithelial cell line was grown in DMEM/F12 supplemented with 5% horse serum, 20 ng/ml EGF, 0.5 mg/ml hydrocortisone, 100 ng/ml cholera toxin, 10 μg/ml insulin, and penicillin/streptoMY-Cin (Invitrogen). RWPE1 and all its derivative sub-lines were grown in K-SFM with 50 mg/ml BPE, 5 ng/ml EGF (Invitrogen). All media were supplemented with 5000 U/mL penicillin/streptomycin (Invitrogen).

All cells were maintained at 37° C. with 5% CO2. Cells were grown until they were 80% confluent before they are treated the respective drugs. For drug treatment, DZNep and GSK126 were purchased from Pharmaron Inc. (Beijing, China), GSK343 was kindly provided by Chemical Probes of University of Toronto, 5'Aza, TSA and human recombinant IFN-γ was purchased from Sigma. For rescue experiment using IFNGR1 blocking antibody, the neutralizing antibody that specifically targets IFNGR1 (anti-CD119, GIR-208, BD Pharmingen) was added to the medium 4 hour prior to the addition of DZNep or/and IFN-γ.

Small Interfering RNA and Plasmids siRNA transfections were conducted using Lipofectamine RNAiMax (Invitrogen). To generate stable over-expression cell lines, target genes from their respective transient expression plasmids were subcloned into the PMN retroviral expression vector. pBabe puro HA-PIK3CA (E545K) was purchased from Addgene and the coding region was subcloned into pMN GFP/IRES retroviral vector (a gift from Dr Linda Penn's lab). PMN-MYC plasmid was from the courtesy of Dr. Linda Penn. RWPE1 cells were infected with retrovirus packaged with PMN-MYC or PMN-PI3KCA (E545K) or the PMN empty vector for 48 hours and followed by GPF sorting.

Target-specific siRNA and non-targeting control siRNA were purchased from 1st Base Singapore and Integrated DNA technologies (IDT) with the following target sequences respectively: EZH2 siRNA: 5'-GACUCUGAAUGCAGUUGCU-3' (SEQ ID NO: 1); MYC siRNA: 5'-UCCUGAGACAGAUCAGCAACAACCG-3' (SEQ ID NO:2). All siRNA were designed by 1st Base Singapore and IDT respectively. For transfection, 30 nM siRNAs were used to transfect cells. 48 h after transfection cell pellets were collected and subjected indicated assays.

Microarray Gene Expression Analysis and Quantitative-PCR

Total RNA was isolated by using Trizol (Invitrogen) and purified with the RNeasy Mini Kit (Qiagen). The microarray hybridization was performed using the Illumina Gene Expression Sentrix BeadChip HumanRef-8_V3, and data analysis was performed by GeneSpring software from Agilent Technologies as described previously. The analyzed gene sets by GeneSpring were next subjected to Ingenuity Pathway Analysis (IPA) for gene ontology (GO) analysis. Reverse transcription and quantitative PCR assays were performed using High Capacity cDNA Archive kit and KAPA SyBr Fast qPCR kit (KAPA biosystems). For quantification of mRNA levels, 18S level was used as an internal control. All reactions were analyzed in an Applied Biosystems PRISM 7500 Fast Real-Time PCR system in 96-well plate format. The sequences of all primers are listed in Table 3.

TABLE 3

Sequences of primers used in microarray and qPCR.

| Gene | Forward Primer 5'-3' | SEQ ID NO: | Reverse Primer 5'-3' | SEQ ID NO: |
|---|---|---|---|---|
| Stat1 | GCCTGGAAGATTTACAAGATGAATATG | 3 | TTGGTCTCGTGTTCTCTGTTCTG | 4 |
| Stat2 | ATGAGTGTGGCCGTTGCA | 5 | TGGGAAAAGGGCTGAATGTC | 6 |
| Stat3 | TGTTCTCTATCAGCACAATCTACGAA | 7 | CAATCCGGGCAATCTCCAT | 8 |
| IRF1 | CATGGCTGGGACATCAACAA | 9 | TTGTATCGGCCTGTGTGAATG | 10 |
| TAP1 | GGGCCTTGTCCAGTTCCAA | 11 | GGTGAATGTCAGCCCCTGTAG | 12 |
| IFITM1 | GGCTTCATAGCATTCGCCTACT | 13 | TCACGTCGCCAACCATCTT | 14 |
| PSMB8 | GGAGGCGTTGTCAATATGTACCA | 15 | GTGCAGCAGGTCACTGACATCT | 16 |
| IRF9 | CCCGACCTCACCGATGAC | 17 | TCTCGCGAAGCTGGATGTC | 18 |
| OAS1 | AGCACTGGTACCAAAATTGTAAGAAG | 19 | CCTCGCTCCCAAGCATAGAC | 20 |
| MX1 | GACAGGACCATCGGAATCTTG | 21 | ACGTCCACAACCTTGTCTTCAGT | 22 |
| XAF1 | GATGTGTCAGCAGAGCATGCA | 23 | TGGCACTCATTGGCCTTATG | 24 |
| IFI16 | ACTGAGTACAACAAAGCCATTTGA | 25 | TTGTGACATTGTCCTGTCCCCAC | 26 |
| IFNGR1 | GTGTGAGCAGGGCTGAGAT | 27 | TCCCAATATACGATAGGGTTCA | 28 |
| IFNAR1 | ATGGGTGTTGTCCGCAG | 29 | CTCCTGTTCCACCTCAGGAT | 30 |
| EZH2 | AGTGTGACCCTGACCTCTGT | 31 | AGATGGTGCCAGCAATAGAT | 32 |
| 18S | CGAACGTCTGCCCTATCAACTT | 33 | ACCCGTGGTCACCATGGTA | 34 |

GEO Accession

Microarray data reported herein from the comparison against RWPE1-vector, RWPE1-MYC and RWPE1-PI3K transformed cells (FIG. 1A) have been deposited in Gene Expression Omnibus with the accession code GSE43686.

Dual Luciferase Reporter Assay

STAT1-specific reporter plasmid pSTAT1, its negative control pGL4 empty vector, and pRL-null were purchased from Signosis. During transfection, 500 ng pGL4/pSTAT1 and 20 ng pRL-null were diluted in 50 µl OPTI-MEM. After 5 minutes of incubation, 2.60 of FugeneHD was added and further incubated for 20 minutes. The transfection mixtures were then added into 400 µl of complete medium-containing 24-well plate, which was seeded with monolayer RWPE cells 18 hours prior transfection. The media of the transfected cells was changed with fresh complete media 24 hours post transfection. Cells were harvested 48 hours post transfection and luciferase activity was detected using the Dual Luciferase system (Promega) following manufacturer's protocol. To analyze luciferase activity, Firefly signals of pGL4/pSTAT1 were normalized to *Renilla* signals of pRL-null in respective samples. pSTAT1/pRL-null ratio were further normalized to pGL4/pRL-null ratio to obtain normalized values corrected for the changes of basic transcription activity for indicated treatment of the cells.

pJAK2 and Total JAK2 ELISA Assay pJAK2 levels were assessed using an ELISA assay kit (Tyr1007/1008, Life Technologies) and total JAK2 level with JAK2 (total) ELISA assay kit. Cells were first lysed with RIPA buffer and processed in the same way as western blot samples. pJAK2 and total JAK2 levels were determined by performing the ELISA assay on the processed cell lysates according to the manufacturer's protocol. The results were expressed as fold change after normalizing the pJAK2 (Tyr1007/1008) level to the total JAK2 level.

Western Blotting

Western Blotting was performed as described previously. Briefly, Cells were scraped, collected, and lysed in RIPA buffer. To release histones from chromatin, cell lysates were further sonicated for 15 sec using a XL2000 Microson Ultrasonic Processor (Misonix). Equal amounts of protein (30 µg) were separated on SDS-polyacrylamide gels and transferred to PVDF membranes. The blots were probed with antibodies against EED (07-368), SUZ12 (07-379), trimethylated H3-K27 (07-449), Acetyl-Histone H3 (06-599), which were purchased from Upstate Biotechnology. IFNGR1 (GIR-94) and anti-IFI16 (1G7) were purchased from Santa Cruz. EZH2 phospho S21 (00388) was purchased from Bethyl Laboratories. EZH2 (AC22), P110α PI3K, p-AKT (T308), p-AKT (S473), pSTAT1Y701, total STAT1, Histone H3 (3H1), Beclin-1 and cleaved PARP were purchased from Cell Signaling. Myc and Actin were purchased from Roche Applied Science and Sigma-Aldrich, respectively.

Chromatin Immunoprecipitation (ChIP) Assay

ChIP assays were performed as described previously. Briefly, pre-cleared chromatin from the cells was immunoprecipitated with antibodies against EZH2 (Active Motif), H3K27me3 (Millipore) or rabbit IgG (Santa Cruz Biotechnology) as a control. The immunoprecipitated DNA was quantified by quantitative real-time PCR using KAPA SyBr Fast qPCR kit (KAPA biosystems) with the specific ChIP primers as listed in the Table 4. Quantification of binding to the promoter was defined as the percentage of the whole cell lysate input DNA. The fold enrichment was derived by normalizing the specific antibody enriched against the IgG-enriched chromatin. CNR1 serves a positive control and Actin is a negative control. Significance of target genes was assessed relative to Actin level.

TABLE 4

Sequences of specific ChIP primers used

| Gene | Primer ID | Forward Primer 5'-3' | SEQ ID NO: | Reverse Primer 5'- 3' | SEQ ID NO: |
|---|---|---|---|---|---|
| IFNAR1 | | TTCGTTTGGAAGAGG GTGTTG | 35 | ACGCAAAAGGGAAG TTAGTTAAGC | 36 |
| CNR1 | | GCAGAGCTCTCCGTA GTCAG | 37 | AACAGGCTGGGGCC ATACAG | 38 |
| ACTIN | | AGTGTGGTCCTGCGA CTTCTAAG | 39 | CCTGGGCTTGAGAGG TAGAGTGT | 40 |
| IFNGR1 | P1 | TGGTGGGTGCTGTGA TTGTG | 41 | AACCCAGTCTTCTGT TCCTGAGA | 42 |
| | P2 | CTTCCTCCGCTCTGC TTCCT | 43 | GATTAGGGAGTGCTC TTGGAATAAA | 44 |
| | P3 | TCAAGACCCAACCTG AATTAGAACT | 45 | TTAGCTCAGTACTTC TCAAACTTCAACA | 46 |
| | P4 | CGCTGAAGGACTTAG CAATGTG | 47 | GGGTTTGTCTGTTAT TTTGCATCTC | 48 |
| | P5 | CCCCAGGAAACCGA AAAAA | 49 | CAACCTGGCACCCCA TTC | 50 |
| | P6 | GCAGCATGGCTCTCC TCTTT | 51 | CGCGGTGCCCATCTC A | 52 |
| | P7 | CGTCTTCTTACTGTA CCTTTTTTATGG | 53 | TGCAGGCAACCGTA GCATAC | 54 |

TABLE 4-continued

Sequences of specific ChIP primers used

| Gene | Primer ID | Forward Primer 5'-3' | SEQ ID NO: | Reverse Primer 5'-3' | SEQ ID NO: |
|---|---|---|---|---|---|
| | P8 | GGATTGCCGGCACTCACTA | 55 | CGAAGAACAAACCCGTACGAA | 56 |
| STAT1 | ChIP 0 | CTCGAGGATCCGATCATTTTAAA | 57 | GGCAGGCAAAGAGCTTGTG | 58 |
| | ChIP 0.5 | GGTGCCGTGGCATCTCTT | 59 | GCACATCTATTTGTTCTTCTTGTCACA | 60 |
| | ChIP 1 | CCAGCGAAGAGTTGGGTGAA | 61 | GGGACTTCTCACCCTGAGTTTG | 62 |
| | ChIP 1.5 | TTGTATGGAGAATGGATTAAAAGGTAGA | 63 | CTGCAGTAGATTCCCGAATGG | 64 |
| | ChIP 2 | GGAGAGGTGTGGACGGGATA | 65 | TCACCCACAGCTTCAGTTTCC | 66 |
| | ChIP 3 | CTGGATTCTCGGCGATGAA | 67 | TGTGTTTGCAGAAGCCCAAA | 68 |
| | ChIP 4 | GCCACCTGTTCTCGGAGATG | 69 | AGAGCACGACTGGCAAGGA | 70 |
| MX1 | ChIP-2 | GGTTGCCCAGCCCTAGGA | 71 | CAGCTCCCTGTGCTGAAATCT | 72 |
| | ChIP-1.5 | CCCGTGACAATTCTGAGGAAA | 73 | CCCTAGTCCAGCTTGGAGGAT | 74 |
| | ChIP-1 | TCCTTCCACACACCCGTTTC | 75 | TCCCTGGAGTCTGGCTCATC | 76 |
| | ChIP-0.5 | ATACGTGCAGGCTTGGATGAC | 77 | AGGCCCGTCTGAGGATCAA | 78 |
| | ChIP + 0.5 | GATGCTAACCGCGCCTCTAC | 79 | AGCCATTTTAGGAGCCCTTTG | 80 |
| IRF1 | ChIP-2 | TTTTTATAGTGTCCTGTTGCCTTCA | 81 | GAAGTTTGCATCTTTGTGGTCTGA | 82 |
| | ChIP-1.5 | GGTCACAGCACTCAGATTGCA | 83 | CCCTCCCGTAGAGGAAATGC | 84 |
| | ChIP-1 | CAGCCGTCTGGGCTTCTC | 85 | CCCCTGGCTGGCTTTAGG | 86 |
| | ChIP-0.5 | CCCTTCGCCGCTAGCTCTA | 87 | TGCGTGCCGTCATTTCG | 88 |
| | ChIP-0 | AAGGGTTAGCGTCCTGGTCTTAG | 89 | CCATTCTACGCCTTCCTGAC | 90 |
| OAS1 | ChIP-2 | CCACAAAAGAAAGATAGCTGGAAAA | 91 | TCTTCCTTGCCCCATGTGTT | 92 |
| | ChIP-1.5 | TCACATTCATACCCACTTTTAAATACG | 93 | CCAGTTACCACCCTTCTTCTAGAAA | 94 |
| | ChIP-1 | AAAAATGAGCTGGGTGCAGTAAC | 95 | GCCCCAGCCTCCTGAATAC | 96 |
| | ChIP-0.5 | AGAGGCAATTTTGTAGTGTTAGAATCAT | 97 | CACTGCAAAAGAAAAAAGTCAGAA | 98 |
| | ChIP + 0.5 | GCACCTGCTGGCTGCAA | 99 | TGAGGAAATTGGAACACAGAGTAGTT | 100 |

Immunohistochemistry-Tissue Microarray (IHC-TMA)

Tissue microarray slides (PR956, BR1503b, LC2083, and LV6161) were purchased from US Biomax. Staining and image analysis of tissue microarray were performed by Histopathology Department from Institute of Molecular and Cell Biology, Agency for Science, Technology, and Research (A*STAR), Singapore. Anti-EZH2 (D2C9 XP) antibody was purchased from Cell Signaling, anti-MYC (9E10) and anti-IFNGR1 antibody (GIR-94) was purchased from Santa Cruz Biotechnology. Briefly, five-micron paraffin-embedded tissue sections cut, deparaffinized, rehydrated, antigens were retrieved by Proteinase K solution; sections were then incubated in 3% H2O2 at room temperature to block endogenous peroxidase. Slides were incubated in primary antibody against EZH2 or IFNGR1 for 45 mins followed by 30 min incubation with anti-mouse Labelled Polymer (Dako, Calif.). Specificity of the immunostaining was determined by the inclusion of isotype-specific IgG as negative control. The detection system was DAB+ Substrate-Chromogen Solution (Dako). The sections were counterstained with hematoxyalin.

Slides were scanned at 20× using an Leica SCN400 slide scanner (Leica Microsystems, Germany). Images were exported to Slidepath Digital Image Hub (Leica Microsystems, Germany) for viewing. Tissue micro-array cores were analyzed using the Measure Stained. Cells algorithm of Slidepath Tissue IA software (Leica Microsystems, Germany). Data was collated using Microsoft Excel. Scanning and image analysis was performed by the Advanced Molecular Pathology Laboratory, IMCB, Singapore.

Cell Viability Assay

The optimal cell seeding was determined empirically for all cell lines by examining the growth of a wide range of seeding densities in a 96-well format to identify conditions that permitted proliferation for 6 days. Cells were then plated at the optimal seeding density 24 h before siRNA or drug treatment in triplicate. Plates were incubated for 6 days at 37° C. in 5% CO2. Cells were then lysed with CellTiter-Glo (CTG) (Promega) and chemiluminescent signal was detected with a microplate reader (TECAN). In addition, an untreated plate of cells was harvested at the time of drug or siRNA addition ($T_0$) to quantify the starting number of cells. CTG values obtained after the 6 day treatment were expressed as percentages of the $T_0$ value and plotted against time of treatment. Cells received 1-5 µM of DZNep, 25 ng/mL of IFN-γ and 0.1-2.5 µM of GSK343 unless stated otherwise for 72-96 h.

FACS Analysis

For the assessment of cell death, cells were harvested in 70% ethanol. Fixed cells were stained with Propidium Iodide (P.I) (50 µg/mL). The stained cells were analyzed for DNA content by FACS in a FACSCalibur (Becton Dickinson Instrument). % of cell death was defined as the sub-G1 population quantified using the CellQuest software (Becton Dickinson). The percentage of dead cells or sub-G1 cells was calculated by comparing the results of each experiment to the results from DMSO-treated cells. Each assay was repeated a minimum of three times, with results reported as means+s.e.m.

Prostatosphere Formation Assay

Prostatospheres were generated according to protocols known to the skilled person in the art. In order to obtain prostatospheres from either DU145 or LNCaP, exponentially growing cultures were dissociated to single cells by standard trypsinization, washed three times with PBS and plated at a density of $1\times10^4$ cells/well in 6-well ultra-low attachment plates (Corning) containing 3 ml of SCM medium (DMEM: F12 plus 10 ng/mL bFGF, 20 ng/mL EGF, 5 mg/mL insulin, and 0.4% BSA) supplemented with 1% KO serum replacement (Invitrogen/Gibco). The cells were treated with DZNep or IFN-γ as indicated the next day and cultured for 7 days. 7 days old prostatospheres formed were stained with 4 µg/ml p-Iodonitrotetrazolium Violet (INT) overnight and were counted and analyzed using a GelCount™ automatic plate scanner (Oxford Optronics) and GelCount Version 0.025.1 software (Oxford Optronics). Plates were scanned at 1200 dpi and the colony detection algorithm was optimized for each cell type and culture time.

Mouse Experiments

For in vivo evaluation of DZNep and IFN-γ treatment, the experiments were conducted in compliance with animal protocol approved by the ASTAR-Biopolis Institutional Animal Care and Use Committee (IACUC) of Singapore. DU145 cells were subcutaneously injected into 6-8 week male nude mice at $5\times10^6$ cells, followed by treatment with vehicle, IFN-γ ($1\times10^7$ IU/kg) alone, DZNep (1 mg/kg) alone or combined DZNep (1 mg/kg) with IFN-γ ($1\times10^7$IU/kg). IFN-γ was administered by intraperitoneal injection daily and DZNep by subcutaneous injection on every alternating day over a duration of 38 days after average tumor size reached around 150 mm$^3$. Tumors were measured by vernier calliper at least twice per week and tumors volume was calculated with formula: $V=W*W*L/2$. Each xenograft treatment arm comprised of 5-8 mice. Differences among groups and treatments were determined by ANOVA followed by t tests. (***$p<0.001$, n.s=not significant) Error bars represent means±s.e.m Statistical Analyses All in vitro experiments were repeated at least three times unless stated otherwise, and data are reported as means+s.e.m. Differences among groups and treatments were determined by Student's t test and $p\leq0.05$ was considered significant unless stated otherwise. Statistical test and graph construction was performed using Graphpad Prism software; version 5.

Methylation Specific PCR

Bisulfite modification of DNA was carried out by using the EZ DNA methylation-Gold kit (ZYMO Research) according the manufacturer's protocol. The CpG island DNA methylation status was determined by methylation specific PCR (MSP) as described in the art. MSP primers targeting the IFNGR1 promoter for methylated sets includes: Forward primer M, 5'-GTGTTTATTGTTGGGT-GTTGC-3' (SEQ ID NO: 101) and Reverse Primer M, 5'-GTCACCGAAATCTATACCGAC-3' (SEQ ID NO: 102). For unmethylated sets includes:

```
Forward Primer U,
                              (SEQ ID NO: 103)
5'-TGTTTATTGTTGGGTGTTGTGT-3'
and Reverse Primer U,
                              (SEQ ID NO: 104)
5'-TTCCATCACCAAAATCTATACCAA-3'.
```

Anchorage-Independent Colony Formation Assay

To assess anchorage-independent growth of RWPE1 transformed cells, 1×104 cells were suspended in K-SFM containing 0.3% agar, 10% fetal bovine serum, and layered on K-SFM containing 0.6% agar and 10% FBS in 6-well plate. After 3 weeks, colonies were stained 18-24 hours with iodonitrotetrozolium chloride (Sigma). Colonies from three replicate wells were quantified using GelCount colony counter (Oxford Optronix).

The invention claimed is:

1. A method of treating cancer in a patient comprising administration of a pharmaceutical composition, wherein the pharmaceutical composition comprises a histone-lysine N-methyltransferase EZH2 (enhancer of zeste homolog 2) inhibitor and an enhancer of interferon-gamma receptor activity, wherein the histone-lysine N-methyltransferase EZH2 (enhancer of zeste homolog 2) inhibitor and an enhancer of interferon-gamma receptor activity are to be administered in a therapeutically effective amount, wherein said patient is characterized by an increased level of EZH2 in a tumor sample and a decreased level of IFNGR1 in a tumor sample, wherein the levels of EZH2 and IFNGR1 in a tumor sample are determined for said patient and compared to the EZH2 and IFNGR1 levels in a non-tumor sample.

2. The method of claim 1, wherein the interferon-gamma receptor is an interferon-gamma receptor 1 (IFNGR1) gene encoding for interferon-gamma receptor (IFNGR1) subunit 1.

3. The method of claim 1, wherein the pharmaceutical composition further comprises one or more pharmaceutically acceptable excipients, vehicles or carriers.

4. The method of claim 1, wherein said inhibitor is selected from a group consisting of:
- (−)-1-[(1R,4R,5S)-3-(Hydroxymethyl)-4,5-dihydroxy-2-cyclopenten-1-yl]4-aminoimidazo[4,5-c]pyridine hydrochloride (DZNep; 3-deazaneplanocin A);
- 1-{[4-amino-5-(2,2-dimethylpropanoyl)-1,3-thiazol-2-yl]sulfanyl}-3,3-dimethylbutan-2-one;
- 4-[4-(4-methyl-1,3-thiazol-2-yl)phenyl]-1,2,3-thiadiazole;
- 2-{[(3,4-dichlorophenyl)carbamoyl]amino}benzoic acid;
- N-(2-methylquinolin-6-yl)quinoxaline-2-carboxamide;
- 2-[(4-tert-butylphenyl)carbonyl]-1H-imidazole;
- 1-(2-hydroxyphenyl)-3-[4-(methoxymethoxy)phenyl]propane-1,3-dione;
- N-(3-acetylphenyl)-8-methoxy-2-oxo-2H-chromene-3-carboxamide;
- 1-{3-[4-(2-phenylethynyl)phenyl]-1H-pyrazol-1-yl}ethan-1-one;
- 3-(thiophen-2-yl)benzoic acid;
- 5-(6-methoxynaphthalen-2-yl)-1H-pyrazole;
- 4-methyl-5-[3-(methylsulfanyl)-1H-pyrazol-5-yl]-2-(thiophen-2-yl)-1,3-thiazole;
- 2-{[(2-chloro-6-fluorophenyl)methyl]sulfanyl}-1-(2,3-dihydro-1,4-benzodioxin-6-yl)ethan-1-one;
- 3-(3-chlorophenyl)-5-(thiophen-3-yl)-1,2,4-oxadiazole;
- 2,3-dihydro-1-benzofuran-5-ylmethanimidamido thiophene-2-carboxylate;
- N-(2,3-dihydro-1,4-benzodioxin-6-yl)[(furan-2-ylmethyl)carbamothioyl]formamide;
- N-[4-(diethylamino)phenyl]-3-methylbenzamide;
- 3-[5-(1,2-oxazol-3-yl)thiophen-2-yl]-5-phenyl-1,2,4-oxadiazole;
- ethyl(2E)-2-cyano-3-{[(E)-{[4-dimethylamino)phenyl]methylidene}amino](methane) sulfinirnidamido}prop-2-enoate;
- (2Z)-2-(4-ethylphenyl)-3-(4-methoxyphenyl)prop-2-enenitrile;
- 5-tert-butyl-3-methyl-N-phenylthieno[3,2-b]thiophene-2-carboxamide;
- 5-(1-butyl-2-oxo-2,3-dihydro-1H-indol-3-ylidene)-2-(piperidin-1-yl)-4,5-dihydro-1,3-thiazol-4-one;
- (2E,6E)-2,6-bis(thiophen-2-ylmethylidene)cyclohexan-1-one;
- 2-[(E)-2-(3,4-dimethoxyphenyl)ethenyl]-1,3-benzothiazole;
- 2-chloro-N-[3-hydroxy-4-(5-methyl-1,3-benzoxazol-2-yl)phenyl]-5-nitrobenzamide;
- 6-chloro-2-phenyl-4H-thiochromen-4-one methyl 2-(3,4-dihydro-2H-1,5-benzodioxepine-7-amido)benzoate;
- 3-chloro-N,N-dimethyl-4-[(1E)-[2-(quinoxalin-2-yl)hydrazin-1-ylidene]methyl]aniline;
- (2E)-1-(2-methyl-1H-indol-3-yl)-3-(thiophen-2-yl)prop-2-en-1-one;
- N-(2,3-dihydro-1,4-benzodioxin-6-yl)-2-(thiophen-2-yl)-1,3-thiazole-4-carboxamide;
- 4-[(E)-2-(1-methyl-1H-1,3-benzodiazol-2-yl)ethenyl]-1,3-thiazole;
- 3-(4-bromophenyl)-3,4-dihydro-1,2,3-benzotriazin-4-one;
- N-(2,4-dichlorophenyl)-3,4-dihydro-2H-1-benzopyran-2-carboxamide;
- N,N-dimethyl-4-[(E)-2-phenylethenyl]aniline;
- 2-(3,4-dichlorophenyl)quinoxaline;
- N-(3-tert-butyl-1H-pyrazol-5-yl)-2,3-dihydro-1,4-benzodioxine-2-carboxamide;
- (2E)-2-(1,3-benzothiazol-2-yl)-3-(4-chlorophenyl)prop-2-enenitrile;
- (4-tert-butylphenyl)methanimidamido 2-(thiophen-2-yl)acetate;
- 5-[4-(3-methyl-1-benzothiophen-2-yl)-1,3-thiazol-2-yl]-1,2-oxazole;
- 1-(4-fluorophenyl)-3-(1-phenyl-5-propyl-1H-pyrazol-4-yl)urea;
- 2-[(2Z)-2-phenyl-2-[(2E)-2-(thiophen-2-ylmethylidene)hydrazin-1-ylidene]ethyl]-1H-1,3-benzodiazole;
- N-{7-oxo-8-oxa-4-thiatricyclo[7.4.0.0^{2,6}]trideca-1(9),2,5,10,12-pentaen-5-yl}thiophene-2-carboxamide;
- 2-(2-chlorophenyl)-1-[4-(dimethylamino)phenyl]ethan-1-one ethyl 4-cyano-1-(4-methylphenyl)-1H-pyrazole-3-carboxylate;
- 3-hydrazinylquinoxaline-2-thiol;
- 1-[(5-tert-butylthiophen-2-yl)carbonyl]piperidine;
- 3-[5-(2-phenylethynyl)thiophen-2-yl]-1-(thiophen-2-ylcarbonyl)-1H-pyrazole;
- 2,5-dichloro-N-(2,3-dihydro-1,4-benzodioxin-2-ylmethyl)thiophene-3-carboxamide;
- 1-tert-butyl-N-(2,3-dihydro-1,4-benzodioxin-6-yl)-5-methyl-1H-pyrazole-3-carboxamide;
- 4-(5-propylpyridin-2-yl)benzonitrile;
- 5-(4-chlorophenyl)-3-(2,2-dichloroacetamido)thiophene-2-carboxamide;
- (4-methanesulfonamidophenyl)methanimidamido thiophene-2-carboxylate;
- ethyl 7-methyl-2-phenylpyrazolo[1,5-a]pyrimidine-6-carboxylate;
- 6-(4-chlorophenyl)-3-phenylthieno[2,3-e][1,2,4]triazine;
- 1-{1-phenyl-1H-pyrazolo[3,4-d]pyrimidin-4-yl}-2,3-dihydro-1H-indole;
- 5-(4-chlorophenyl)-2-(4-methylphenyl)-2H-1,2,3,4-tetrazole;
- 4-[(1E)-[2-(3,5-dichloropyridin-4-yl)hydrazin-1-ylidene]methyl]-N,N-dimethylaniline;
- 3-(5-tert-butyl-1,2-oxazol-3-yl)-1-phenylurea;
- (4-chlorophenyl)methanimidamido 3-chlorothiophene-2-carboxylate;
- N-{4-[(E)-2-phenyldiazen-1-yl]phenyl}acetamide;
- methyl 4-[(pyrimidin-2-ylsulfanyl)methyl]benzoate;
- 2-phenylimidazo[1,2-a]pyridine;
- 6-chloro-2-phenyl-4H-thiochromen-4-one;
- 2-{[(4-methylphenyl)methyl]sulfanyl}-5-(pyrazin-2-yl)-1,3,4-thiadiazole;
- 5,7-dihydroxy-2-(4-hydroxyphenyl)-4H-chromen-4-one;
- (E)-[I-(1H-pyrrol-2-yl)ethylidene]amino N-(4-chlorophenyl)carbamate;
- 1-benzoyl-3-2,3-dihydro-1H-inden-5-ylthiourea;
- 1-{1-phenyl-1H-pyrazolo[3,4-d]pyrimidin-4-yl}-2,3-dihydro-1H-indole;
- N,5-diphenyl-1,3,4-oxadiazole-2-carboxamide;
- (3Z)-3-(2,3-dihydro-1-benzofuran-5-ylmethylidene)-2,3-dihydro-1H-indol-2-one;
- [(3-methylbutyl)sulfanyl]-N-phenylformamide;
- 2,4-dihydroxy-5,7-diphenylpyrano[2,3-d]pyrimidin-8-ium perchlorate;
- ethyl 7-hydroxy-9-oxo-9H-xanthene-2-carboxylate;
- [({[3,5-Dimethyl-1-(2-methyl-2-propanyl)-1H-pyrazol-4-yl]methylene}amino)oxy]{[3-(trifluoromethyl)phenyl]amino}methanone;
- 5-[(4-iodophenyl)amino]-3-phenyl-1,3-thiazolidine-2,4-dione;

N-(furan-2-ylmethyl)-2-[methane(4-phenoxyphenyl)sulfonamido]acetamide N-(3-methoxyphenyl)-6-phenylpyridazin-3-amine;
ethyl (2E)-3-[(2-chlorophenyl)amino]-2-cyanoprop-2-enoate;
1-[3-chloro-1-benzothiophen-2-yl)carbonyl]-1H, 2H,3H, 4H,6H, 10bH-pyrimido[2,1-a]isoindol-6-one;
2-(4-chlorophenyl)-5-[(cyclopropylmethyl)sulfanyl]-1,3,4-oxadiazole;
1-[6-(benzyloxy)-3-tert-butyl-2-hydroxyphenyl]ethan-1-one;
3-[(1E)-1-[(2,2-dichloroethenyl)imino]-2,2-dimethylpropyl]-1-(4-methylphenyl)thiourea;
6,7-dimethyl-2-phenylquinoxaline;
5-(2,3-dihydro-1-benzofuran-5-yl)-3-(4-fluorophenyl)-1,2,4-oxadiazole;
2-{4-[(4-methylphenyl)methoxy]phenyl}acetonitrile;
5-(1,2,3-thiadiazol-4-yl)-3-[4-(trifluoromethyl)phenyl]-1,2,4-oxadiazole;
N-(2-methylquinolin-6-yl)-2-phenylacetamide;
3-(piperidin-1-ylcarbonyl)-5-(thiophen-2-yl)-1, 2-oxazole;
N-(3,4-dimethylphenyl)[(E)-N'-(thiophen-2-yl methylidene)hydrazinecarbonyl]formamide;
2-(2,3-dimethoxyphenyl)-2,3-dihydro-1,3-benzothiazole;
2-methyl-5-(naphthalen-2-yl)-1,3-thiazole hydrobromide;
(cyclohexylcarbamothioyl)-N-(4-fluorophenyl)formamide;
4-(1,3-benzothiazol-2-yl)-1-methyl-1H-pyrazol-3-amine;
(4-tert-butylphenyl)methanimidamido 5-methyl-1,2-oxazole-3-carboxylate;
N-[2-(methylsulfanyl)-1,3-benzothiazol-6-yl]thiophene-2-carboxamide;
N-(5-cyclopropyl-1,3,4-thiadiazol-2-yl)-2H-1,3-benzodioxole-5-carboxamide;
(2E)-3-(2-chlorophenyl)-N-(2-methylbut-3-yn-2-yl)prop-2-enamide;
3-methyl-N-phenyl-1-benzothiophene-2-carbothioamide;
5-(2,5-dichlorophenyl)-N-[2-(trifluoromethyl)phenyl]furan-2-carboxamide;
3-(5-methyl-1,2-oxazol-3-yl)-5-(thiophen-2-yl)-1,2,4-oxadiazole;
N-(1H-indazol-3-yl)-3-methoxybenzamide;
2-(4-tert-butylphenyl)-5-[(propane-1-sulfonyl)methyl]-1,3,4-oxadiazole;
1-[2-(4-chlorophenoxymethyl)-4-methyl-1,3-thiazol-5-yl]ethan-1-one;
(4-methanesulfonamidophenyl)methanimidamido N-(4-methylphenyl)carbamate;
N-phenyl-4,5,6,7-tetrahydro-1,3-benzothiazol-2-amine hydrochloride;
7-nitro-N-(2-phenylethyl)-1H-indole-2-carboxamide;
2-{[(2E)-4-(pyridin-2-ylsulfanyl)but-2-en-1-yl]sulfanyl}pyridine;
4-[(E)-2-(3-methylthiophen-2-yl)ethenyl]-2-[(3-nitropyridin-2-yl)sulfanyl]pyrimidine;
4-(4-chlorophenyl)-2-[(4-methoxyphenyl)methyl]-1,3-thiazole;
(3Z)-3-{[5-(thiophen-2-yl)thiophen-2-yl]methylidene}-2,3-dihydro-1H-indol-2-one;
N-(4-bromo-2, 5-difluorophenyl)-2,3-dimethylbenzamide;
sodium N-phenyl(phenylamino)carboximidate;
2-(benzylsulfanyl)-N-(2,3-dihydro-1H-inden-2-yl)acetamide;
(5Z)-5-[(5-methylfuran-2-yl)methylidene]-3-phenyl-1,3-thiazolidine-2,4-dione;
N-{4-[(3-chlorophenyl)carbamoyl]phenyl}thiophene-2-carboxamide;
N-[(3-chlorophenyl)methyl]-5-(methylsulfanyl)-1,3,4-thiadiazol-2-amine;
(E)-2-(phenylamino)-3-(phenylimino)guanidine;
(2Z)-3-methyl-2-[2-(3-methyl-2,3-dihydro-1,3-benzoxazol-2-ylidene)hydrazin-1-ylidene]-2,3-dihydro-1,3-benzoxazole;
3-[2-(2H-1,4-benzothiazin-3-yl)hydrazin-1-yl]-2H-1,4-benzothiazine;
3-(3,4-dimethyl-1,2-oxazol-5-yl)-1-[4-(dimethylamino)-3,5-difluorophenyl]carbonylurea;
(3Z)-3-[2-(2,5-difluorophenyl)hydrazin-1-ylidene]piperidin-2-one;
N'-[(E)-[1-(1-benzofuran-2-yl)ethylidene]amino](methylsulfanyl)methanimidamide;
(2Z)-3-(9H-fluoren-2-ylcarbamoyl)prop-2-enoic acid;
4-[2-(2,3-dihydro-1,4-benzodioxin-6-yl)diazen-1-yl]-N,N-diethylaniline;
4,5-dichloro-N-(3-chloro-4-fluorophenyl)-1, 2-thiazole-3-carboxamide;
5-[4-(4-methoxyphenoxy)phenyl]-1H-pyrazole;
1-cyclohexyl-3-[(Z)-(1H-pyrazol-3-ylmethylidene)amino]thiourea;
[5-(4-chlorophenyl)-3-methyl-2-sulfanylidene-1,3,4-thiadiazinan-6-ylidene]amino 5-tert-butylthiophene-2-carboxylate;
N-(2-phenylethyl)benzenecarbothioamide;
5-amino-3-methyl-2-N-phenylthiophene-2,4-dicarboxamide;
3-amino-5-(thiophen-3-yl)thiophene-2-carboxamide;
(2E)-2-{[4-(trifluoromethoxy)phenyl]imino}-3,4-dihydro-2H-1,3-benzoxazin-4-one;
3-hydroxy-9H-xanthen-9-one;
4-[(E)-2-(3,5-dihydroxyphenyl)ethenyl]benzene-1,2-diol;
(3-chlorophenyl)methanimidamido 6-(2,2,2-trifluoroethoxy)pyridine-3-carboxylate;
5-phenyl-3-(pyrrolidin-1-yl)-1,2-thiazole-4-carbonitrile,
7-hydroxy-3-(4-hydroxyphenyl)-4H-chromen-4-one;
2-(4-fluorophenyl)-2H,3H,5H,6H,7H,8H-[1,2,4]triazolo[4,3-a]pyrimidin-3-one;
(4-chlorophenyl)methanimidamido 2,6-difluorobenzoate;
2-(2-amino-3-methoxyphenyl)-4H-chromen-4-one;
6,7-dimethoxy-2-phenylquinoxaline;
6-methoxy-3-phenyl-[1,2,4]triazolo[4,3-a]pyridazine;
5-[4-(furan-2-ylcarbonyl)piperazin-1-yl]-3-(thiophen-2-yl)-1,2,4-thiadiazole;
(E)-{1-[2-(4-chlorophenoxymethyl)-1,3-thiazol-4-yl]ethylidene}amino benzoate;
N-[(2-chloro-6-fluorophenyl)carbonyl]-N'-(4-methylpyridin-2-yl)ethanediamide;
(E)-hydroxy[1-(2-phenyl-1,3-thiazol-4-yl)ethylidene]amine;
ethyl 1-{[4-(trifluoromethoxy)phenyl]carbamoyl}piperidine-4-carboxylate;
3-(3-methyl-1H-indol-1-yl)-N-[4-(morpholin-4-yl)phenyl]propanamide;
6,8-dimethyl-1-methylidene-2-(4-methylphenyl)-1,4-dihydronaphthalene;
N'-[(2-methyl-1,3-thiazol-4-yl)methoxy]-4-(trifluoromethyl)benzene-1-carboximidamide;
1-[4-(benzyloxy)phenyl]-3-[(3-cyanopyridin-2-yl)amino]urea;
2-phenylimidazo[1,2-a]pyridine;
3-(morpholin-4-yl)-5-[4-(trifluoromethyl)phenyl]-1,2-thiazole-4-carbonitrile;

N-(2-chlorophenyl)-2-[(3-cyano-6-acetylpyridin-2-yl)sulfanyl]acetamide;
3-[4-(4-methoxyphenyl)-1,3-thiazol-2-yl]-5-methyl-1,2-oxazole;
N-(3-bromo-5-methylpyridin-2-yl)-4-ethylbenzamide;
2-(5-methyl-1,2-oxazol-3-yl)-5-[3-(trifluoromethyl)phenyl]-1,3,4-oxadiazole;
(E)-[1-(3-methyl-1-benzothiophen-2-yl)ethylidene]amino N-phenylcarbamate;
N-(2,3-dihydro-1H-inden-2-yl)-3-(3-methyl-1H-indol-1-yl)propanamide;
1,3-dimethanesulfonyl-2,3-dihydro-1H-1,3-benzodiazole;
methyl 2-[5-methyl-2-(thiophen-2-amido)-1,3-thiazol-4-yl]acetate;
4-[(5-{[(4-chlorophenyl)sulfanyl]methyl}furan-2-yl)carbonyl]morpholine;
2-oxo-2-phenylethyl 2,3-dimethoxybenzoate;
N-(4-chlorophenyl)-4-hydroxy-2-oxo-1,2-dihydroquinoline-3-carboxamide;
(2,4-dichlorophenyl)methyl N-[(2-fluorophenyl)carbonyl]carbamate;
2-[(4-chlorophenyl)carbonyl]-1-benzofuran;
4-chlorophenyl 2,3-dihydro-1-benzofuran-5-carboxylate;
2-[4-(dimethylamino)phenyl]-1,2,3,4-tetrahydroquinolin-4-one;
[6-(ethylsulfanyl)pyridin-3-yl]methanimidamido thiophene-2-carboxylate;
N-[(6-methyl-2-oxo-4-propyl-1,2-dihydropyridin-3-yl)methyl]-6-[2-(4-methylpiperazin-1-yl)pyridin-4-yl]-1-(propan-2-yl)-1H-indazole-4-carboxamide (GSK343);
N-[(4,6-dimethyl-2-oxo-1,2-dihydro-3-pyridinyl)methyl]-3-methyl-1-((1 S)-1-methylpropyl)-6-[6-(1-piperazinyl)-3-pyridinyl]-1H-indole-4-carboxamide (GSK126); and
N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-indazole-4-carboxamide (GSK926).

5. The method of claim 1, wherein said inhibitor is (−)-1-[(1R,4R,5S)-3-(hydroxymethyl)-4,5-dihydroxy-2-cyclopenten-1-yl]4-aminoimidazo[4,5-c]pyridine hydrochloride (DZNep: 3-deazaneplanocin A).

6. The method of claim 1, wherein said inhibitor is an EZH2-binding antibody or antigen-binding fragment thereof.

7. The method of claim 1, wherein said inhibitor is a nucleic acid molecule or conjugate thereof.

8. The method of claim 7, wherein said nucleic acid molecule is a small interfering RNA.

9. The method of claim 1, wherein said enhancer is interferon-gamma (IFN-γ).

10. The method of claim 1, wherein said inhibitor is DZNep and said enhancer is IFN-γ.

11. The method according to claim 1 wherein said inhibitor is present in an amount of 1 mg/kg or less.

12. The method according to claim 1, wherein said enhancer is present in an amount of less than $5\times10^6$ IU/kg.

13. The method according to claim 1, wherein said cancer is a metastatic cancer.

14. The method according to claim 13, wherein said metastatic cancer is a prostate cancer.

15. The method according to claim 1, wherein cancer is selected from a group consisting of liver, ovarian, lung, acute lymphoblastic leukemia, breast, bladder, and lymphoma mantle-cell cancer.

16. The method of claim 15, wherein the breast cancer is luminal B breast cancer.

17. A method for treating cancer in a patient with a difference in the level of EZH2 mRNA, and/or EZH2 cDNA, and/or EZH2 protein and IFNGR1 mRNA, and/or IFNGR1 cDNA, and/or IFNGR1 protein in a tumor sample, and the level of EZH2 mRNA, and/or EZH2 cDNA, and/or EZH2 protein and IFNGR1 mRNA, and/or IFNGR1 cDNA, and/or IFNGR1 protein from a non-tumor sample, wherein the level of EZH2 mRNA, and/or EZH2 cDNA, and/or EZH2 protein are at least 2-fold higher in the tumor sample and the IFNGR1 mRNA, and/or IFNGR1 cDNA, and/or IFNGR1 protein level is at least 2-fold lower in the tumor sample, wherein the method comprises determining said differences in the level of EZH2 and/or IFNGER1 in a patient and administration of a pharmaceutical composition as defined in claim 1.

* * * * *

SEQUENCE LISTING

<160> NUMBER OF SEQ ID NOS: 104

<210> SEQ ID NO 1
<211> LENGTH: 19
<212> TYPE: RNA
<213> ORGANISM: Artificial Sequence
<220> FEATURE:
<223> OTHER INFORMATION: siRNA sequence binding to EZH2 mRNA

<400> SEQUENCE: 1
gacucugaau gcaguugcu                                             19

<210> SEQ ID NO 2
<211> LENGTH: 25
<212> TYPE: RNA
<213> ORGANISM: Artificial Sequence
<220> FEATURE:
<223> OTHER INFORMATION: siRNA sequence binding to MYC mRNA

<400> SEQUENCE: 2
uccugagaca gaucagcaac aaccg                                      25

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
gcctggaaga tttacaagat gaatatg                                    27

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ttggtctcgt gttctctgtt ctg                                        23

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
atgagtgtgg ccgttgca                                              18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tgggaaaagg gctgaatgtc                                            20

<210> SEQ ID NO 7
<211> LENGTH: 26
<212> TYPE: DNA
<213> ORGANISM: Artificial Sequence -continued

```
<220> FEATURE:
<223> OTHER INFORMATION: Primer

<400> SEQUENCE: 7
tgttctctat cagcacaatc tacgaa                                          26

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
caatccgggc aatctccat                                                  19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
catggctggg acatcaacaa                                                 20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ttgtatcggc ctgtgtgaat g                                               21

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
gggccttgtc cagttccaa                                                  19

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggtgaatgtc agcccctgta g                                               21

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ggcttcatag cattcgccta ct                                              22
```

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
tcacgtcgcc aaccatctt                                                    19

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
ggaggcgttg tcaatatgta cca                                               23

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gtgcagcagg tcactgacat ct                                                22

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
cccgacctca ccgatgac                                                     18

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
tctcgcgaag ctggatgtc                                                    19

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
agcactggta ccaaaattgt aagaag                                            26

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cctcgctccc aagcatagac    20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gacaggacca tcggaatctt g    21

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
acgtccacaa ccttgtcttc agt    23

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
gatgtgtcag cagagcatgc a    21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
tggcactcat tggcctttatg    20

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
actgagtaca acaaagccat ttga    24

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
ttgtgacatt gtcctgtccc cac    23

<210> SEQ ID NO 27

-continued

```
<211> LENGTH: 19
<212> TYPE: DNA
<213> ORGANISM: Artificial Sequence
<220> FEATURE:
<223> OTHER INFORMATION: Primer

<400> SEQUENCE: 27
gtgtgagcag ggctgagat                                                    19

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
tcccaatata cgatagggtt ca                                                22

<210> SEQ ID NO 29
<211> LENGTH: 17
<212> TYPE: DNA
<213> ORGANISM: Artificial Sequence
<220> FEATURE:
<223> OTHER INFORMATION: Primer

<400> SEQUENCE: 29
atgggtgttg tccgcag                                                      17

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ctcctgttcc acctcaggat                                                   20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
agtgtgaccc tgacctctgt                                                   20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
agatggtgcc agcaatagat                                                   20

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
```

```
cgaacgtctg ccctatcaac tt                                              22

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
acccgtggtc accatggta                                                  19

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
ttcgtttgga agagggtgtt g                                               21

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
acgcaaaagg gaagttagtt aagc                                            24

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gcagagctct ccgtagtcag                                                 20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aacaggctgg ggccatacag                                                 20

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
agtgtggtcc tgcgacttct aag                                             23

<210> SEQ ID NO 40
<211> LENGTH: 23
<212> TYPE: DNA
```

```
<213> ORGANISM: Artificial Sequence
<220> FEATURE:
<223> OTHER INFORMATION: Primer

<400> SEQUENCE: 40
cctgggcttg agaggtagag tgt                                              23

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
tggtgggtgc tgtgattgtg                                                  20

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
aacccagtct tctgttcctg aga                                              23

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
cttcctccgc tctgcttcct                                                  20

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
gattagggag tgctcttgga ataaa                                            25

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
tcaagaccca acctgaatta gaact                                            25

<210> SEQ ID NO 46
<211> LENGTH: 28
<212> TYPE: DNA
<213> ORGANISM: Artificial Sequence
<220> FEATURE:
<223> OTHER INFORMATION: Primer

<400> SEQUENCE: 46
ttagctcagt acttctcaaa cttcaaca                                         28
```

```
<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
cgctgaagga cttagcaatg tg                                              22

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
gggtttgtct gttattttgc atctc                                           25

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
ccccaggaaa ccgaaaaaa                                                  19

<210> SEQ ID NO 50
<211> LENGTH: 18
<212> TYPE: DNA
<213> ORGANISM: Artificial Sequence
<220> FEATURE:
<223> OTHER INFORMATION: Primer

<400> SEQUENCE: 50
caacctggca ccccattc                                                   18

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
gcagcatggc tctcctcttt                                                 20

<210> SEQ ID NO 52
<211> LENGTH: 16
<212> TYPE: DNA
<213> ORGANISM: Artificial Sequence
<220> FEATURE:
<223> OTHER INFORMATION: Primer

<400> SEQUENCE: 52
cgcggtgccc atctca                                                     16

<210> SEQ ID NO 53
<211> LENGTH: 28
<212> TYPE: DNA
<213> ORGANISM: Artificial Sequence
<220> FEATURE:
```

```
<223> OTHER INFORMATION: Primer

<400> SEQUENCE: 53
cgtcttctta ctgtaccttt ttttatgg                                              28

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
tgcaggcaac cgtagcatac                                                       20

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
ggattgccgg cactcacta                                                        19

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56
cgaagaacaa acccgtacga a                                                     21

<210> SEQ ID NO 57
<211> LENGTH: 23
<212> TYPE: DNA
<213> ORGANISM: Artificial Sequence
<220> FEATURE:
<223> OTHER INFORMATION: Primer

<400> SEQUENCE: 57
ctcgaggatc cgatcatttt aaa                                                   23

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
ggcaggcaaa gagcttgtg                                                        19

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
ggtgccgtgg catctctt                                                         18
```

```
<210> SEQ ID NO 60
<211> LENGTH: 27
<212> TYPE: DNA
<213> ORGANISM: Artificial Sequence
<220> FEATURE:
<223> OTHER INFORMATION: Primer

<400> SEQUENCE: 60
gcacatctat tgttcttct tgtcaca                                    27

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
ccagcgaaga gttgggtgaa                                           20

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
gggacttctc accctgagtt tg                                        22

<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
ttgtatggag aatggattaa aaggtaga                                  28

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
ctgcagtaga ttcccgaatg g                                         21

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
ggagaggtgt ggacgggata                                           20

<210> SEQ ID NO 66
<211> LENGTH: 21
<212> TYPE: DNA
<213> ORGANISM: Artificial Sequence
<220> FEATURE:
<223> OTHER INFORMATION: Primer
```

<400> SEQUENCE: 66
tcacccacag cttcagtttc c                                              21

<210> SEQ ID NO 67
<211> LENGTH: 19
<212> TYPE: DNA
<213> ORGANISM: Artificial Sequence
<220> FEATURE:
<223> OTHER INFORMATION: Primer

<400> SEQUENCE: 67
ctggattctc ggcgatgaa                                                 19

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tgtgtttgca gaagcccaaa                                                20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
gccacctgtt ctcggagatg                                                20

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
agagcacgac tggcaagga                                                 19

<210> SEQ ID NO 71
<211> LENGTH: 18
<212> TYPE: DNA
<213> ORGANISM: Artificial Sequence
<220> FEATURE:
<223> OTHER INFORMATION: Primer

<400> SEQUENCE: 71
ggttgcccag ccctagga                                                  18

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
cagctccctg tgctgaaatc t                                              21

<210> SEQ ID NO 73
<211> LENGTH: 21

```
<212> TYPE: DNA
<213> ORGANISM: Artificial Sequence
<220> FEATURE:
<223> OTHER INFORMATION: Primer

<400> SEQUENCE: 73
cccgtgacaa ttctgaggaa a                                              21

<210> SEQ ID NO 74
<211> LENGTH: 21
<212> TYPE: DNA
<213> ORGANISM: Artificial Sequence
<220> FEATURE:
<223> OTHER INFORMATION: Primer

<400> SEQUENCE: 74
ccctagtcca gcttggagga t                                              21

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
tccttccaca cacccgtttc                                                20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
tccctggagt ctggctcatc                                                20

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
atacgtgcag gcttggatga c                                              21

<210> SEQ ID NO 78
<211> LENGTH: 19
<212> TYPE: DNA
<213> ORGANISM: Artificial Sequence
<220> FEATURE:
<223> OTHER INFORMATION: Primer

<400> SEQUENCE: 78
aggcccgtct gaggatcaa                                                 19

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
```
gatgctaacc gcgcctctac                                               20

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
agccatttta ggagcccttt g                                             21

<210> SEQ ID NO 81
<211> LENGTH: 25
<212> TYPE: DNA
<213> ORGANISM: Artificial Sequence
<220> FEATURE:
<223> OTHER INFORMATION: Primer

<400> SEQUENCE: 81
tttttatagt gtcctgttgc cttca                                         25

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
gaagtttgca tctttgtggt ctga                                          24

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
ggtcacagca ctcagattgc a                                             21

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
ccctcccgta gaggaaatgc                                               20

<210> SEQ ID NO 85
<211> LENGTH: 18
<212> TYPE: DNA
<213> ORGANISM: Artificial Sequence
<220> FEATURE:
<223> OTHER INFORMATION: Primer

<400> SEQUENCE: 85
cagccgtctg ggcttctc                                                 18

<210> SEQ ID NO 86
<211> LENGTH: 18
<212> TYPE: DNA
<213> ORGANISM: Artificial Sequence

```
<220> FEATURE:
<223> OTHER INFORMATION: Primer

<400> SEQUENCE: 86
cccctggctg gctttagg                                                          18

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
cccttcgccg ctagctcta                                                         19

<210> SEQ ID NO 88
<211> LENGTH: 17
<212> TYPE: DNA
<213> ORGANISM: Artificial Sequence
<220> FEATURE:
<223> OTHER INFORMATION: Primer

<400> SEQUENCE: 88
tgcgtgccgt catttcg                                                           17

<210> SEQ ID NO 89
<211> LENGTH: 23
<212> TYPE: DNA
<213> ORGANISM: Artificial Sequence
<220> FEATURE:
<223> OTHER INFORMATION: Primer

<400> SEQUENCE: 89
aagggttagc gtcctggtct tag                                                    23

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
ccattctacg ccttcctgac                                                        20

<210> SEQ ID NO 91
<211> LENGTH: 25
<212> TYPE: DNA
<213> ORGANISM: Artificial Sequence
<220> FEATURE:
<223> OTHER INFORMATION: Primer

<400> SEQUENCE: 91
ccacaaaaga aagatagctg gaaaa                                                  25

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
tcttccttgc cccatgtgtt                                                        20
```

```
<210> SEQ ID NO 93
<211> LENGTH: 27
<212> TYPE: DNA
<213> ORGANISM: Artificial Sequence
<220> FEATURE:
<223> OTHER INFORMATION: Primer

<400> SEQUENCE: 93
tcacattcat acccactttt aaatacg                                            27

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94
ccagttacca cccttcttct agaaa                                              25

<210> SEQ ID NO 95
<211> LENGTH: 23
<212> TYPE: DNA
<213> ORGANISM: Artificial Sequence
<220> FEATURE:
<223> OTHER INFORMATION: Primer

<400> SEQUENCE: 95
aaaaatgagc tgggtgcagt aac                                                23

<210> SEQ ID NO 96
<211> LENGTH: 19
<212> TYPE: DNA
<213> ORGANISM: Artificial Sequence
<220> FEATURE:
<223> OTHER INFORMATION: Primer

<400> SEQUENCE: 96
gccccagcct cctgaatac                                                     19

<210> SEQ ID NO 97
<211> LENGTH: 28
<212> TYPE: DNA
<213> ORGANISM: Artificial Sequence
<220> FEATURE:
<223> OTHER INFORMATION: Primer

<400> SEQUENCE: 97
agaggcaatt ttgtagtgtt agaatcat                                           28

<210> SEQ ID NO 98
<211> LENGTH: 26
<212> TYPE: DNA
<213> ORGANISM: Artificial Sequence
<220> FEATURE:
<223> OTHER INFORMATION: Primer

<400> SEQUENCE: 98
cactgcaaaa agaaaaaaag tcagaa                                             26

<210> SEQ ID NO 99
<211> LENGTH: 17
<212> TYPE: DNA
<213> ORGANISM: Artificial Sequence
<220> FEATURE:
<223> OTHER INFORMATION: Primer
```

```
<400> SEQUENCE: 99
gcacctgctg gctgcaa                                              17

<210> SEQ ID NO 100
<211> LENGTH: 26
<212> TYPE: DNA
<213> ORGANISM: Artificial Sequence
<220> FEATURE:
<223> OTHER INFORMATION: Primer

<400> SEQUENCE: 100
tgaggaaatt ggaacacaga gtagtt                                    26

<210> SEQ ID NO 101
<211> LENGTH: 21
<212> TYPE: DNA
<213> ORGANISM: Artificial Sequence
<220> FEATURE:
<223> OTHER INFORMATION: Primer

<400> SEQUENCE: 101
gtgtttattg ttgggtgttg c                                         21

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
gtcaccgaaa tctataccga c                                         21

<210> SEQ ID NO 103
<211> LENGTH: 22
<212> TYPE: DNA
<213> ORGANISM: Artificial Sequence
<220> FEATURE:
<223> OTHER INFORMATION: Primer

<400> SEQUENCE: 103
tgtttattgt tgggtgttgt gt                                        22

<210> SEQ ID NO 104
<211> LENGTH: 24
<212> TYPE: DNA
<213> ORGANISM: Artificial Sequence
<220> FEATURE:
<223> OTHER INFORMATION: Primer

<400> SEQUENCE: 104
ttccatcacc aaaatctata ccaa                                      24
```